(12) United States Patent
Lee et al.

(10) Patent No.: US 8,546,576 B2
(45) Date of Patent: Oct. 1, 2013

(54) 3 OR 4-SUBSTITUTED PIPERIDINE COMPOUNDS

(75) Inventors: Ki-Ho Lee, Daejeon (KR); Chun-Eung Park, Seoul (KR); Kyung-Hyun Min, Daejeon (KR); Yong-Je Shin, Daejeon (KR); Yu-Jin Shin, Daejeon (KR); Hae-Jeong Yoon, Daejeon (KR); Won Kim, Daejeon (KR); Eun-Ju Ryu, Daejeon (KR)

(73) Assignee: SK Biopharmaceuticals Co., Ltd., Seoul (KR)

( * ) Notice: Subject to any disclaimer, the term of this patent is extended or adjusted under 35 U.S.C. 154(b) by 620 days.

(21) Appl. No.: 12/477,369

(22) Filed: Jun. 3, 2009

(65) Prior Publication Data
US 2009/0306140 A1   Dec. 10, 2009

Related U.S. Application Data

(60) Provisional application No. 61/059,289, filed on Jun. 6, 2008.

(51) Int. Cl.
C07D 405/00 (2006.01)
A01N 43/40 (2006.01)

(52) U.S. Cl.
USPC .......................................... 546/210; 514/326

(58) Field of Classification Search
USPC .......................................... 546/210; 514/326
See application file for complete search history.

(56) References Cited

U.S. PATENT DOCUMENTS

| 6,936,626 | B2 * | 8/2005 | Mabire et al. | 514/357 |
| 2007/0010516 | A1 | 1/2007 | Aissaoui et al. | |
| 2007/0167487 | A1 | 7/2007 | Peters et al. | |

FOREIGN PATENT DOCUMENTS

| WO | WO 02/051837 | 7/2002 |
| WO | WO2004072071 | 8/2004 |
| WO | 2005118539 | 12/2005 |
| WO | 2007020213 A2 | 7/2007 |

OTHER PUBLICATIONS

Pharmaceutical Salts, J. Pharm. Sci., 1977; 66(1): 1-19.
Gu H. et al., J. Biol Chem., 1994, 269, p. 7124-7130.
Galli A. et al., J Exp Biol., 1995, 198, p. 2197-2212.
The International Search Report by the International Searching Authority, issued on Jan. 14, 2010, in the PCT application No. PCT/KR2009/003042.
Dziadulewicz et al, "Naphthalen-1-yl-(4 pentyloxynaphthalen-1-yl)methanone: A Potent, Orally Bioavailable Human CB1/CB2 Dual Agonist with Antihyperalgesic Properties and Restricted Central Nervous System Penetration,"J. Med. Chem., 2007, 50 (16), pp. 3851-3856.
The extended European Search Report by the European Patent Office, issued on Mar. 22, 2012, in the corresponding European patent application No. 09758544.2.

* cited by examiner

Primary Examiner — Nizal Chandrakumar
(74) Attorney, Agent, or Firm — Harness, Dickey & Pierce, P.L.C.; J. Timothy Keane; Kisuk Lee

(57) ABSTRACT

There are disclosed racemic or enantiomerically enriched 3- or 4-substituted piperidine compounds represented by the following structural formula (I):

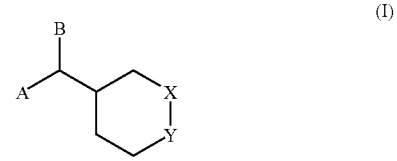

(I)

or any of their isomers, or pharmaceutically acceptable salts thereof. Also disclosed are pharmaceutical compositions containing the subject compounds. The subject compounds are useful for the treatment of diseases of the central nervous system, particularly depression, anxiety and pain disorder.

20 Claims, No Drawings

3 OR 4-SUBSTITUTED PIPERIDINE COMPOUNDS

RELATED APPLICATIONS

This application claims priority from U.S. Provisional Application Ser. No. 61/059,289, filed Jun. 6, 2008, the disclosure of which is incorporated herein in its entirety.

FIELD OF THE INVENTION

The present invention relates, in general, to racemic or enantiomerically enriched novel 3 or 4-substituted piperidine derivatives and pharmaceutically useful salts thereof, a pharmaceutical composition comprising an effective amount of racemic or enantiomerically enriched novel 3 or 4-substituted piperidine derivatives as monoamine neurotransmitter re-uptake inhibitors to treat central nervous system diseases and a method of treating central nervous system diseases in a mammal. More particularly, the present invention relates to racemic or enantiomerically enriched novel 3-substituted piperidine derivatives having various azole moieties and pharmaceutically useful salts thereof, useful to treat the diseases of the central nervous system such as depression, anxiety and pain disorder.

BACKGROUND OF THE INVENTION

The three biogenic amines, serotonin, norepinephrine and dopamine are most closely linked to CNS disorders such as depression. The majority of antidepressants in current use selectively inhibit the reuptake of serotonin and/or norepinephrine. Although a strong dopamine re-uptake inhibiting activity is considered with the risk of undesirable central stimulation effects, many reports have disclosed that the triple monoamine neurotransmitter, i.e serotonin, norepinephrine and dopamine re-uptake inhibitors are useful for the treatment of CNS disorders such as depression, anxiety, attention deficit hyperactivity disorder, obesity, drug addiction and pain disorder. For example, International Patent Application No. WO 2004/072071 discloses the novel 8-aza-bicyclo[3,2,1]octane derivatives useful as monoamine neurotransmitter re-uptake inhibitors.

3-Substituted piperidine compounds are effectively used for controlling various central nervous system (CNS) disorders. For example, International Patent Application No. WO 02/51837 discloses 3-substituted piperidine derivatives that are suitable for treating anxiety, depression, sleep disorder. Active research and development efforts have continued to be directed to the application of 3-substituted piperidine compounds for the treatment of CNS disorders.

SUMMARY OF THE INVENTION

A principal object of the present invention is to provide 3 or 4-substituted piperidine derivatives, represented by the following structural formula (I):

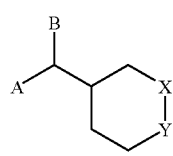
(I)

or any of its isomers or pharmaceutically acceptable salts thereof wherein

A is selected from the group consisting of phenyl, naphthyl, benzothiophenyl, pyridyl, quinolyl and isoquinolyl which may be substituted with one or more identical or different substituents selected from the group consisting of hydrogen, halogen, straight- or branched-chain $C_{1-4}$ alkyl, straight- or branched-chain $C_{1-3}$ alkoxy, nitro, cyano, trifluoromethyl, trifluoromethoxy, methanesulfonyl, phenyloxy, phenyl and thienyl;

B is an azole selected from the group consisting of imidazole, pyrazole, triazole, benzotriazole, tetrazole, 5-methyl tetrazole and 5-phenyl tetrazole which are linked by nitrogen as represented by the following structural formulae (II):

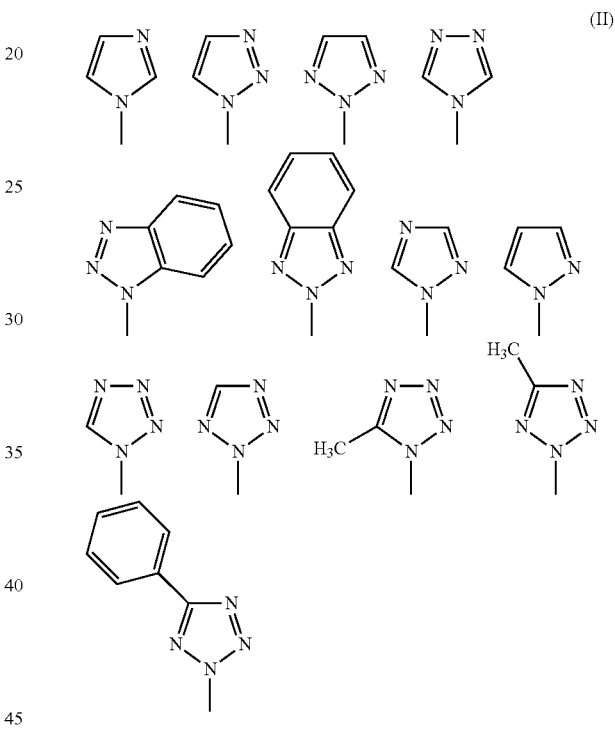
(II)

one of X and Y is carbon and the other is N—R wherein R is hydrogen or a $C_{1-4}$ alkyl group.

More specifically, the present 3 or 4-substituted piperidine compounds represented by the above formula (I) comprises any of its isomers or any mixture of its isomers represented by the following structural formulae (III) and (IV):

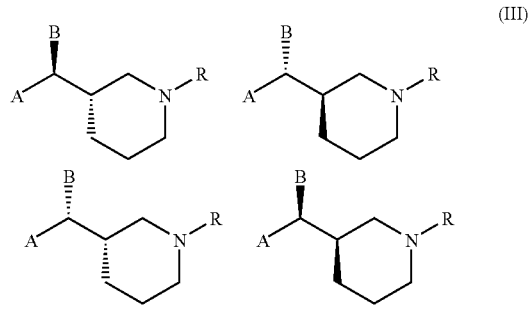
(III)

3
-continued

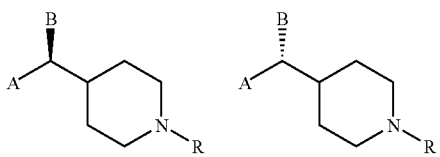
(IV)

wherein A, B and R are as defined above.

It is another object of the present invention to provide a pharmaceutical composition comprising an effective amount of racemic or enantiomerically enriched 3 or 4-substituted piperidine compounds represented by the above structural formula (I), in particular, the compounds represented by the above structural formulae (III) and (IV) for treating disorders of central nervous system such as depression, anxiety and pain disorder.

It is still another object of the present invention to provide a method of treating disorders of central nervous system such as depression, anxiety and pain disorder in a mammal in need of such treatment by administering an effective amount of racemic or enantiomerically enriched 3 or 4-substituted piperidine compounds represented by the above structural formula (I), in particular, the compounds represented by the above structural formulae (III), (IV) and a pharmaceutical acceptable carrier.

DETAILED DESCRIPTION OF THE INVENTION

In accordance with the present invention, the compound represented by the structural formula (I) and pharmaceutical acceptable salts thereof can be prepared by techniques and procedures readily available to one of ordinary skill in the art, for example by following the procedures as set forth in the following schemes. These schemes are not intended to limit the scope of the invention in any way. All substituents, unless otherwise indicated, are previously defined. The reagents and starting materials are readily available to one of ordinary skill in the art.

In accordance with the present invention, the compound represented by the structural formulae (III) and pharmaceutical acceptable salts thereof can be prepared by the following steps starting from tert-butyl 3-[methoxy(methyl)carbamoyl]piperidine-1-carboxylate represented by the following general structural formula (V):

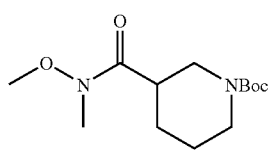
(V)

It should be noted that the stereochemistry of piperidine 3-position of the general structural formulae (III) depends solely on that of the starting material (V); a starting material (V) with an (S)-enantiomer yields only a product with (3S)-enantiomer and a starting material (V) with a (R)-enantiomer yields only a product with (3R)-enantiomer.

An example of the method for preparing the general formulae (III) in which R is hydrogen, will be described below in detail.

Initially, tert-butyl 3-[methoxy(methyl)carbamoyl]piperidine-1-carboxylate is reacted with substituted phenyl or naphthyl magnesium bromide represented by the following structural formula (VI), (VII) or (VIII):

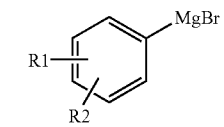
(VI)

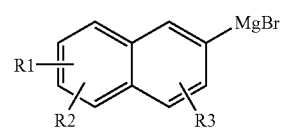
(VII)

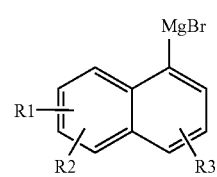
(VIII)

wherein

R1, R2, R3 is one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl, phenyloxy, phenyl and thienyl; to synthesize the Boc-protected amino ketone compounds represented by the structural formula (IX).

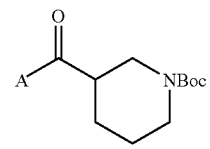
(IX)

wherein

A is selected from the group consisting of phenyl, naphthyl, benzothiophenyl, pyridyl, quinolyl and isoquinolyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl, phenyloxy, phenyl and thienyl.

It is considered that the Boc-protected amino ketone compounds represented by the structural formula (IX) wherein A is benzothiophenyl; pyridyl; quinolyl or isoquinolyl can be prepared through similar methods.

The compound of formula (IX) is treated with (R)-2-methyl-CBS-oxazaborolidine or (S)-2-methyl-CBS-oxazaborolidine followed by Borane-THF complex to synthesize enantiomerically enriched alcohol compounds represented by the structural formula (X).

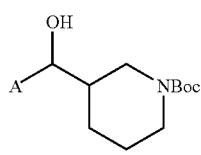

The compound of formula (X) is reacted with triphenylphosphine, diisopropyl azodicarboxylate and azole compounds such as imidazole, pyrazole, triazole, tetrazole, 5-methyltetrazole, 5-phenyltetrazole, benzotriazole represented by the structural formula (II) to synthesize the Boc-protected amino azole compounds represented by the structural formula (XI)

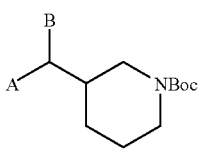

wherein

A is selected from the group consisting of phenyl, naphthyl, benzothiophenyl, pyridyl, quinolyl and isoquinolyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl, phenyloxy, phenyl and thienyl;

B is selected from the azole group such as imidazole, pyrazole, triazole, benzotriazole, tetrazole, 5-methyl tetrazole and 5-phenyl tetrazole which are linked by nitrogen and represented by the following structural formula (II):

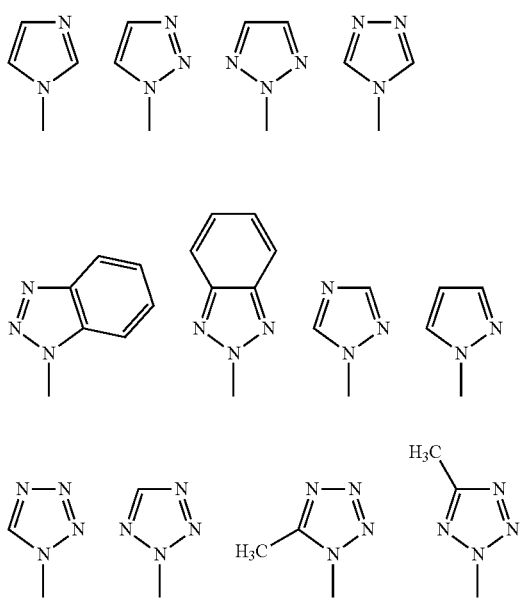

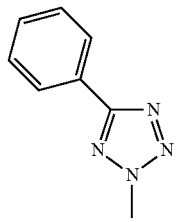

This intermediate is deprotected by methanolic hydrochloric acid solution resulting in the 3-substituted piperidine derivatives represented by the general formula (XII).

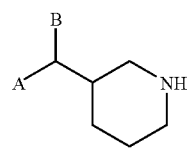

The compound of formula (XII) may be converted into pharmaceutically acceptable salts (XIII) by treating with an acid capable of forming a pharmacologically useful salt.

This procedure is summarized as set forth in Reaction Scheme I below.

Reaction Scheme 1

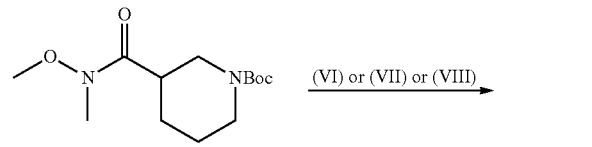

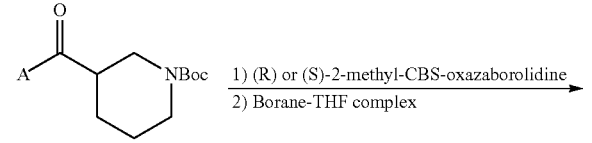

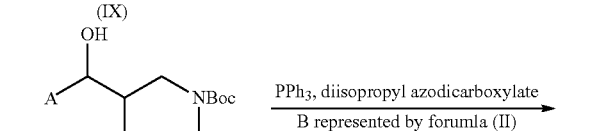

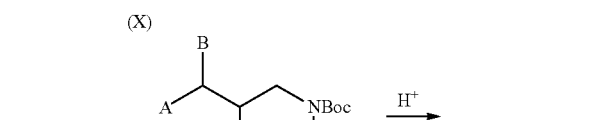

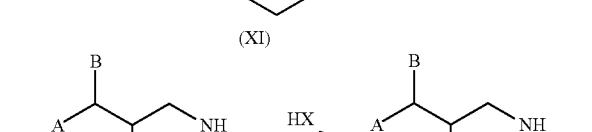

Details of the reaction conditions described in Reaction Scheme I are as follows. For the conversion of the compounds (V) to the compound (IX), it is preferred that the concentration of the starting material (V) is about 0.005 to 0.1 moles with phenyl or naphthyl magnesium bromide ranging from about 2.0 to 3.0 equivalents. This reaction is preferably carried out at a temperature of 10 to 30° C. The resulting ketone compound is treated with 0.5 to 1.0 equivalents of (R) or (S)-2-methyl-CBS-oxazaborolidine at a temperature of −78° C. followed by addition of borane-THF complex ranging from 1.0 to 3.0 equivalents to give the enatiomerically enriched alcohol compound of the formula (X). The resulting alcohol compound is treated with triphenylphosphine, diisopropyl azodicarboxylate and azole compounds raging from 1.0 to 2.5 equivalent, preferably carried out at a temperature of about 0 to 30° C. For this reaction, an ethereal solvent such as diethyl ether and tetrahydrofuran or aromatic hydrocarbons such as benzene, toluene and zylene may be used. Compound (XI) is treated with methanolic 6% hydrochloric acid at a temperature of about −10 to 30° C., followed by neutralization to yield the compound of the formula (XII).

In Reaction Scheme I, HX represents an acid capable of forming a pharmacologically useful salt with the basic nitrogen atom. Specific examples of the anhydrous acid used for the preparation of the compound (XIII) from the compound (XII) include hydrochloric acid, hydrobromic acid, sulfuric acid, phosphoric acid, acetic acid, benzoic acid, carbonic acid, citric acid, malonic acid, salicylic acid, malic acid, fumaric acid, oxalic acid, succinic acid, tartaric acid, lactic acid, gluconic acid, ascorbic acid, maleic acid, aspartic acid, Camphorsulfonic acid, p-toluenesulfonic acid, benzene sulfonic acid, methane sulfonic acid, ethane sulfonic acid, hydroxymethane sulfonic acid and hydroxyethane sulfonic acid and the like. Additional acids can refer to "Pharmaceutical Salts", *J. Pharm. Sci.*, 1977; 66 (1): 1-19. This preparation is executed in a reaction media which can be exemplified by an ethereal solvent such as tetrahydrofuran, an alcoholic solvent such as methanol, an ester solvent such as ethyl acetate, a halogenated hydrocarbon solvent, and the mixtures thereof. An ethereal solvent is recommended as an addition solution, including ethyl ether, propyl ether, isopropyl ether, butyl ether, isobutyl ether. The concentration of the compound (XII) is on the order of about 0.01 to 5 moles.

The method for preparing the general formulae (III) in which R is not hydrogen will be described below in detail.

Initially, the prepared amine compounds (XII) is reacted with triethylamine and an appropriate alkylhalide in dichloromethane at 0° C. to yield the alkylated amine compound represented by the general formulae (III) in which R is not hydrogen.

The compound of formulae (III) in which R is not hydrogen, may be converted into pharmaceutically acceptable salts (XIV) as described above.

This procedure is summarized as set forth in Reaction Scheme II below.

Reaction Scheme II

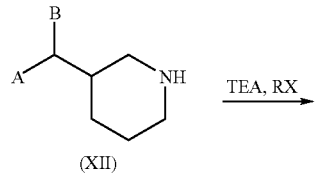

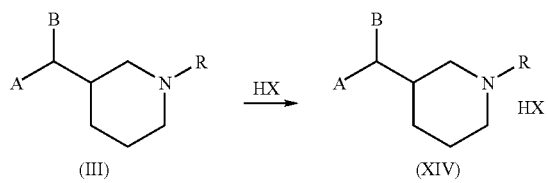

Details of the reaction conditions described in Reaction Scheme II are as follows. For the conversion of the compounds (XII) to the compound (III), the concentration of the starting material (XII) is about 0.005 to 0.1 moles with triethylamine ranging from about 2.0 to 3.0 equivalents and alkylhalide ranging from about 1.5 to 3 equivalents. This reaction is preferably carried out at a temperature of 0 to 30° C. For this alkylation, an ethereal solvent such as diethyl ether and tetrahydrofuran, a halogenated hydrocarbon solvent such as dichloromethane and chloroform, an alcohol solvent such as methanol, ethanol and propanol, or the mixture thereof may be used.

In Reaction Scheme II, HX represents an acid capable of forming a pharmacologically useful salt with the basic nitrogen atone as described above.

In accordance with the present invention, the compound represented by the structural formula (IV) and pharmaceutical acceptable salts thereof can be prepared by the following steps starting from tert-butyl 4-[methoxy(methyl)carbamoyl]piperidine-1-carboxylate represented by the following general structural formula (XV):

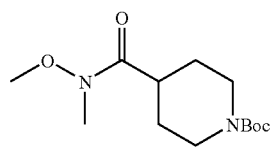

An example of the method for preparing the general formula (IV) in which R is hydrogen, will be described below in detail.

Initially, tert-butyl 4-[methoxy(methyl)carbamoyl]piperidine-1-carboxylate is reacted with substituted phenyl or naphthyl magnesium bromide represented by the following structural formula (VI), (VII) or (VIII):

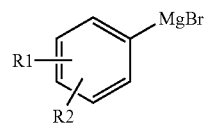

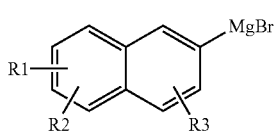

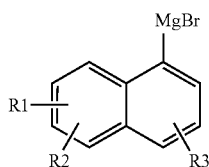
(VIII)

wherein

R1, R2 or R3 is one or more identical or different substituents selected from the group consisting of hydrogen, halogen, straight- or branched-chain alkyl of from 1 to 4 carbon atoms, straight or branched chain alkoxy of from 1 to 3 carbon atoms, nitro, cyano, trifluoromethyl, trifluoromethoxy, methanesulfonyl, phenyloxy, phenyl and thienyl;

to synthesize the Boc-protected amino ketone compounds represented by the structural formula (XVI).

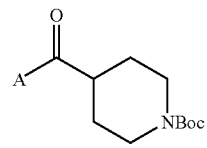
(XVI)

wherein

A is selected from the group consisting of phenyl, naphthyl benzothiophenyl, pyridyl, quinolyl and isoquinolyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl, phenyloxy, phenyl and thienyl;

It is considered that the Boc-protected amino ketone compounds represented by the structural formula (IX) wherein A is benzothiophenyl, pyridyl, quinolyl or isoquinolyl can be prepared through similar method.

The compound of formula (XVI) is treated with (R)-2-methyl-CBS-oxazaborolidine or (S)-2-methyl-CBS-oxazaborolidine followed by Borane-THF complex to synthesize enantiomerically enriched alcohol compounds represented by the structural formula (XVII).

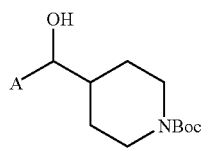
(XVII)

The compound of formula (XVII) is reacted with triphenylphosphine, diisopropyl azodicarboxylate and azole compounds such as imidazole, pyrazole, triazole, tetrazole, 5-methyltetrazole, 5-phenyltetrazole, benzotriazole represented by the structural formula (II) to synthesize the Boc-protected amino azole compounds represented by the structural formula (XVIII)

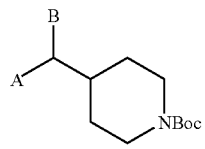
(XVIII)

wherein

A is selected from the group consisting of phenyl, naphthyl, benzothiophenyl, pyridyl, quinolyl and isoquinolyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl, phenyloxy, phenyl and thienyl;

B is selected from the azole group such as imidazole, pyrzole, triazole, benzotriazole, tetrazole, 5-methyl tetrazole or 5-phenyl tetrazole which are linked by nitrogen and represented by the following structural formulae (II):

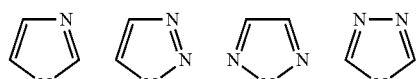
(II)

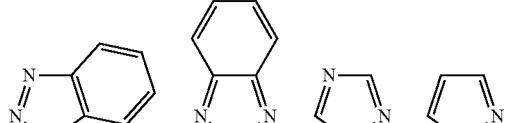

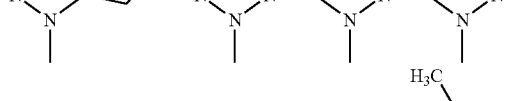

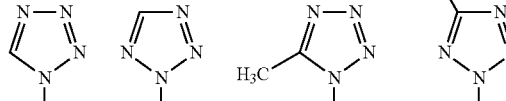

This intermediate is deprotected by methanolic hydrochloric acid solution resulting in the 4-substituted piperidine derivatives represented by the general formula (XIX).

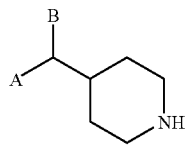
(XIX)

The enantiomeric mixture (XIX) is dissolved in a small amount of isopropylalcohol and separated by chiral preparative Liquid Chromatography. Separation is performed by using a CHIRALPACK OD-H column (manufactured by Daicel Chemical Industries, Ltd.) as the Prep-LC column, at a column temperature of 25° C., with n-hexane/isopropylalcohol including 0.1% triethylamine (90:10) as the eluent to get pure enantiomers.

The enantiomeric pure compound of formula (XIX) may be converted into pharmaceutically acceptable salts (XX) as described above.

This procedure is summarized as set forth in Reaction Scheme III below.

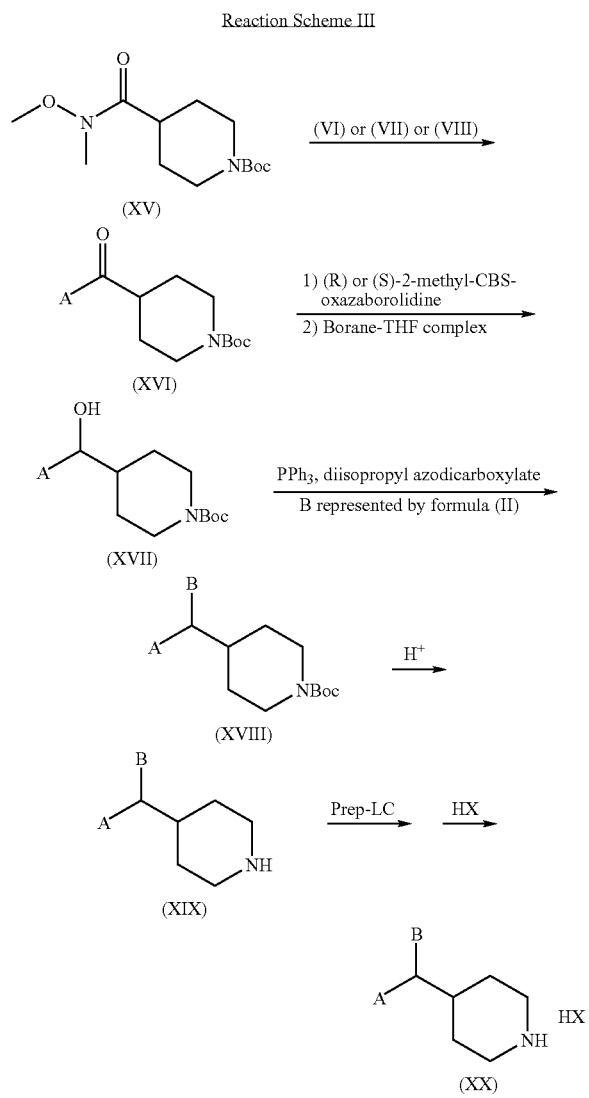

Details of the reaction conditions described in Reaction Scheme III are as follows. For the conversion of the compounds (XV) to the compound (XVI), it is preferred that the concentration of the starting material (XV) is about 0.005 to 0.1 moles with phenyl or naphthyl magnesium bromide ranging from about 2.0 to 3.0 equivalents. This reaction is preferably carried out at a temperature of 10 to 30° C. The resulting ketone compound is treated with 0.5 to 1.0 equivalents of (R) or (S)-2-methyl-CBS-oxazaborolidine at a temperature of −78° C. followed by addition of borane-THF complex ranging from 1.0 to 3.0 equivalents to give the enatiomerically enriched alcohol compound of the formula (XVII). The resulting alcohol compound is treated with triphenylphosphine, diisopropyl azodicarboxylate and azole compounds raging from 1.0 to 2.5 equivalents, preferably carried out at a temperature of about 0 to 30° C. For this reaction, an ethereal solvent such as diethyl ether and tetrahydrofuran or aromatic hydrocarbons such as benzene, toluene and zylene may be used. Compound (XVIII) is treated with methanolic 6% hydrochloric acid at a temperature of about −10 to 30° C., followed by neutralization to yield the compound of the formula (XIX).

In Reaction Scheme III, HX represents an acid capable of forming a pharmacologically useful salt with the basic nitrogen atom as described above.

The method for preparing the general formula (IV) in which R is not hydrogen, will be described below in detail.

Initially, the prepared amine compounds (XIX) is reacted with triethylamine and an appropriate alkylhalide in dichloromethane at 0° C. to yield the alkylated amine compound represented by the general formula (IV) in which R is not hydrogen.

The compound of formula (IV) in which R is not hydrogen, may be converted into pharmaceutically acceptable salts (XXI) as described above.

This procedure is summarized as set forth in Reaction Scheme IV below.

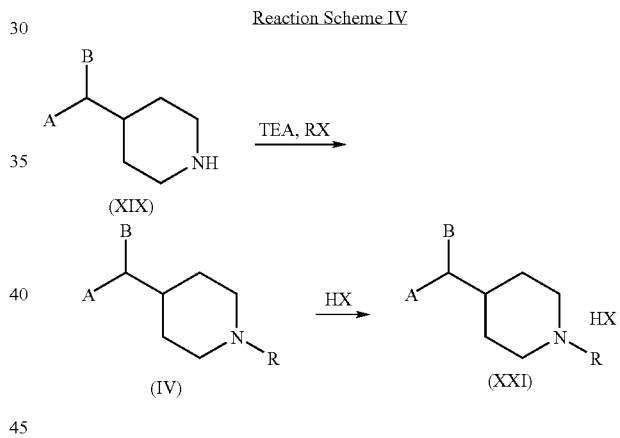

Details of the reaction conditions described in Reaction Scheme IV are as follows. For the conversion of the compounds (XIX) to the compound (IV), the concentration of the starting material (XIX) is about 0.005 to 0.1 moles with triethylamine ranging from about 2.0 to 3.0 equivalents and alkylhalide ranging from about 1.5 to 3 equivalents. This reaction is preferably carried out at a temperature of 0 to 30° C. For this alkylation, an ethereal solvent such as diethyl ether and tetrahydrofuran, a halogenated hydrocarbon solvent such as dichloromethane and chloroform, an alcohol solvent such as methanol, ethanol and propanol, or the mixture thereof may be used.

In Reaction Scheme IV, HX represents an acid capable of forming a pharmacologically useful salt with the basic nitrogen atom as described above.

Representative examples of the compounds (I), (III) and (IV) from scheme I, II, III and IV include the following compounds:
(3R)-3-[(R)-naphthalen-2-yl(2H-tetrazol-2-yl)methyl]piperidine
(3S)-3-[(S)-naphthalen-2-yl(2H-tetrazol-2-yl)methyl]piperidine (3R)-3-[(S)-naphthalen-2-yl(2H-tetrazol-2-yl)methyl]piperidine
(3S)-3-[(R)-naphthalen-2-yl(2H-tetrazol-2-yl)methyl]piperidine
(3R)-3-[(R)-naphthalen-2-yl(1H-tetrazol-1-yl)methyl]piperidine
(3S)-3-[(S)-naphthalen-2-yl(1H-tetrazol-1-yl)methyl]piperidine
(3R)-3-[(S)-naphthalen-2-yl(1H-tetrazol-1-yl)methyl]piperidine
(3S)-3-[(R)-naphthalen-2-yl(1H-tetrazol-1-yl)methyl]piperidine
(3S)-3-[(R)-(5-methyl-2H-tetrazol-2-yl)(naphthalen-2-yl)methyl]piperidine
(3S)-3-[(S)-(5-methyl-2H-tetrazol-2-yl)(naphthalen-2-yl)methyl]piperidine
(3R)-3-[(S)-(5-methyl-2H-tetrazol-2-yl)(naphthalen-2-yl)methyl]piperidine
(3R)-3-[(R)-(5-methyl-2H-tetrazol-2-yl)(naphthalen-2-yl)methyl]piperidine
(3R)-3-[(R)-naphthalen-2-yl(2H-1,2,3-triazol-2-yl)methyl]piperidine
(3S)-3-[(S)-naphthalen-2-yl(2H-1,2,3-triazol-2-yl)methyl]piperidine
(3R)-3-[(R)-(3,4-dichlorophenyl)(2H-tetrazol-2-yl)methyl]piperidine
(3S)-3-[(S)-(3,4-dichlorophenyl)(2H-tetrazol-2-yl)methyl]piperidine
(3R)-3-[(R)-(4-chlorophenyl)(2H-tetrazol-2-yl)methyl]piperidine
(3S)-3-[(S)-(4-chlorophenyl)(2H-tetrazol-2-yl)methyl]piperidine
(3R)-3-[(S)-(4-chlorophenyl)(2H-tetrazol-2-yl)methyl]piperidine
(3S)-3-[(R)-(4-chlorophenyl)(2H-tetrazol-2-yl)methyl]piperidine
(3R)-3-[(R)-naphthalen-1-yl)(2H-tetrazol-2-yl)methyl]piperidine
(3S)-3-[(S)-naphthalen-1-yl)(2H-tetrazol-2-yl)methyl]piperidine
(3R)-3-[(R)-(4-isopropylphenyl)(2H-tetrazol-2-yl)methyl]piperidine
(3S)-3-[(S)-(4-isopropylphenyl)(2H-tetrazol-2-yl)methyl]piperidine
(3R)-3-[(S)-(4-isopropylphenyl)(2H-tetrazol-2-yl)methyl]piperidine
(3S)-3-[(R)-(4-isopropylphenyl)(2H-tetrazol-2-yl)methyl]piperidine
(3S)-3-[(S)-(3,4-dimethoxyphenyl)(2H-tetrazol-2-yl)methyl]piperidine
(3S)-3-[(R)-(3,4-dimethoxyphenyl)(2H-tetrazol-2-yl)methyl]piperidine
(3S)-3-[(S)-(3,4-dimethoxyphenyl)(1H-tetrazol-1-yl)methyl]piperidine
(3S)-3-[(R)-(3,4-dimethoxyphenyl)(1H-tetrazol-1-yl)methyl]piperidine
(3S)-3-[(S)-phenyl(2H-tetrazol-2-yl)methyl]piperidine
(3S)-3-[(R)-phenyl(2H-tetrazol-2-yl)methyl]piperidine
(3S)-3-{(S)-2H-tetrazol-2-yl[4-(trifluoromethyl)phenyl]methyl}piperidine
(3S)-3-{(R)-2H-tetrazol-2-yl[4-(trifluoromethyl)phenyl]methyl}piperidine
(3S)-3-[(S)-(6-methoxynaphthalen-2-yl)(2H-tetrazol-2-yl)methyl]piperidine
(3S)-3-[(R)-(6-methoxynaphthalen-2-yl)(2H-tetrazol-2-yl)methyl]piperidine
(3S)-3-[(S)-(4-methylphenyl)(2H-tetrazol-2-yl)methyl]piperidine
(3S)-3-[(R)-(4-methylphenyl)(2H-tetrazol-2-yl)methyl]piperidine
(3S)-3-[(S)-(3-chlorophenyl)(2H-tetrazol-2-yl)methyl]piperidine
(3S)-3-[(R)-(3-chlorophenyl)(2H-tetrazol-2-yl)methyl]piperidine
(3S)-3-[(S)-(2,4-difluorophenyl)(2H-tetrazol-2-yl)methyl]piperidine
(3S)-3-[(R)-(2,4-difluorophenyl)(2H-tetrazol-2-yl)methyl]piperidine
(3S)-3-[(S)-(4-methoxyphenyl)(2H-tetrazol-2-yl)methyl]piperidine
(3S)-3-[(R)-(4-methoxyphenyl)(2H-tetrazol-2-yl)methyl]piperidine
(3S)-3-[(S)-(4-methoxyphenyl)(1H-tetrazol-1-yl)methyl]piperidine
(3S)-3-[(R)-(4-methoxyphenyl)(1H-tetrazol-1-yl)methyl]piperidine
(3S)-3-[(S)-(4-phenoxyphenyl)(2H-tetrazol-2-yl)methyl]piperidine
(3S)-3-[(R)-(4-phenoxyphenyl)(2H-tetrazol-2-yl)methyl]piperidine
(3S)-3-[(S)-(4-phenoxyphenyl)(1H-tetrazol-1-yl)methyl]piperidine
(3S)-3-[(R)-(4-phenoxyphenyl)(1H-tetrazol-1-yl)methyl]piperidine
(3S)-3-[(S)-(4-fluorophenyl)(2H-tetrazol-2-yl)methyl]piperidine
(3S)-3-[(R)-(4-fluorophenyl)(2H-tetrazol-2-yl)methyl]piperidine
(3S)-3-[(S)-biphenyl-4-yl(2H-tetrazol-2-yl)methyl]piperidine
(3S)-3-[(R)-biphenyl-4-yl(2H-tetrazol-2-yl)methyl]piperidine
(3S)-3-{(S)-2H-tetrazol-2-yl[3-(trifluoromethyl)phenyl]methyl}piperidine
(3S)-3-{(R)-2H-tetrazol-2-yl[3-(trifluoromethyl)phenyl]methyl}piperidine
(3S)-3-[(S)-(4-propylphenyl)(2H-tetrazol-2-yl)methyl]piperidine
(3S)-3-[(R)-(4-propylphenyl)(2H-tetrazol-2-yl)methyl]piperidine
(3S)-3-[(S)-(4-methoxynaphthalen-1-yl)(2H-tetrazol-2-yl)methyl]piperidine
(3S)-3-[(R)-(4-methylnaphthalen-1-yl)(2H-tetrazol-2-yl)methyl]piperidine
(3S)-3-[(S)-(3-methylphenyl)(2H-tetrazol-2-yl)-methyl]piperidine
(3S)-3-[(R)-(3-methylphenyl)(2H-tetrazol-2-yl)-methyl]piperidine
(3R)-3-[(R)-(3-methoxyphenyl)(2H-tetrazol-2-yl)methyl]piperidine
(3S)-3-[(R)-(3-methoxyphenyl)(2H-tetrazol-2-yl)methyl]piperidine
(3S)-3-[(S)-1-benzothiophen-5-yl(2H-tetrazol-2-yl)methyl]piperidine
(3S)-3-[(R)-1-benzothiophen-5-yl(2H-tetrazol-2-yl)methyl]piperidine
(3R)-3-[(R)-(6-chloronaphthalen-2-yl)(2H-tetrazol-2-yl)methyl]piperidine
(3S)-3-[(S)-(6-chloronaphthalen-2-yl)(2H-tetrazol-2-yl)methyl]piperidine
(3R)-3-[(S)-(6-chloronaphthalen-2-yl)(2H-tetrazol-2-yl)methyl]piperidine (3S)-3-[(R)-(6-chloronaphthalen-2-yl)(2H-tetrazol-2-yl)methyl]piperidine
(3S)-3-[(S)-(6-fluoronaphthalen-2-yl)(2H-tetrazol-2-yl)methyl]piperidine
(3S)-3-[(R)-(6-fluoronaphthalen-2-yl)(2H-tetrazol-2-yl)methyl]piperidine
(3S)-1-ethyl-3-[(S)-naphthalen-2-yl(2H-tetrazol-2-yl)methyl]piperidine
(3R)-3-[(R)-naphthalen-2-yl(5-phenyl-tetrazol-2-yl)methyl]piperidine
(3S)-3-[(S)-naphthalen-2-yl(5-phenyl-tetrazol-2-yl)methyl]piperidine
(3R)-3-[(S)-naphthalen-2-yl(5-phenyl-tetrazol-2-yl)methyl]piperidine
(3S)-3-[(B)-naphthalen-2-yl(5-phenyl-tetrazol-2-yl)methyl]piperidine
1-{(S)-naphthalen-2-yl[(3S)-piperidin-3-yl]methyl}-1H-benzotriazole
1-{(R)-naphthalen-2-yl[(3S)-piperidin-3-yl]methyl}-1H-benzotriazole
2-{(S)-naphthalen-2-yl[(3S)-piperidin-3-yl]methyl}-2H-benzotriazole
2-{(R)-naphthalen-2-yl[(3S)-piperidin-3-yl]methyl}-2H-benzotriazole
(3S)-3-[(R)-1-benzothiophen-3-yl(2H-tetrazol-2-yl)methyl]piperidine
(3R)-3-[(R)-(6-fluoronaphthalen-2-yl)(2H-tetrazol-2-yl)methyl]piperidine
(3R)-3-[(S)-(6-fluoronaphthalen-2-yl)(2H-tetrazol-2-yl)methyl]piperidine
(3S)-3-[(S)-(6-methylnaphthalen-2-yl)(2H-tetrazol-2-yl)methyl]piperidine
(3S)-3-[(R)-(6-methylnaphthalen-2-yl)(2H-tetrazol-2-yl)methyl]piperidine
(3S)-3-[(S)-(4-fluoronaphthalen-1-yl)(2H-tetrazol-2-yl)methyl]piperidine
(3S)-3-[(R)-(4-fluoronaphthalen-1-yl)(2H-tetrazol-2t-yl)methyl]piperidine
(3S)-3-[(R)-naphthalen-2-yl(4H-1,2,4-triazol-4-yl)methyl]piperidine
(3S)-3-[(S)-naphthalen-2-yl(1H-1,2,4-triazol-1-yl)methyl]piperidine
(3S)-3-[(R)-naphthalen-2-yl(1H-1,2,4-triazol-1-yl)methyl]piperidine
(3S)-3-[(R)-naphthalen-2-yl(1H-pyrazol-1-yl)methyl]piperidine
(3S)-3-[(S)-1-benzothiophen-2-yl(2H-tetrazol-2-yl)methyl]piperidine
(3S)-3-[(R)-1-benzothiophen-2-yl(2H-tetrazol-2-yl)methyl]piperidine
(3S)-3-[(S)-(3,4-difluorophenyl)(2H-tetrazol-2-yl)methyl]piperidine
(3S)-3-[(R)-(3,4-difluorophenyl)(2H-tetrazol-2-yl)methyl]piperidine
(3S)-3-[(S)-(2,3-dichlorophenyl)(2H-tetrazol-2-yl)methyl]piperidine
(3S)-3-[(R)-(2,3-dichlorophenyl)(2H-tetrazol-2-yl)methyl]piperidine
(3R)-3-[(R)-(1-fluoronaphthalen-2-yl)(2H-tetrazol-2-yl)methyl]piperidine
(3S)-3-[(S)-(1-fluoronaphthalen-2-yl)(2H-tetrazol-2-yl)methyl]piperidine
(3R)-3-[(S)-(1-fluoronaphthalen-2-yl)(2H-tetrazol-2-yl)methyl]piperidine
(3S)-3-[(R)-(1-fluoronaphthalen-2-yl)(2H-tetrazol-2-yl)methyl]piperidine
(3R)-3-[(R)-(1-fluoronaphthalen-2-yl)(5-methyl-2H-tetrazol-2-yl)methyl]piperidine
(3S)-3-[(S)-(1-fluoronaphthalen-2-yl)(5-methyl-2H-tetrazol-2-yl)methyl]piperidine
(3R)-3-[(S)-(1-fluoronaphthalen-2-yl)(5-methyl-2H-tetrazol-2-yl)methyl]piperidine
(3S)-3-[(R)-(1-fluoronaphthalen-2-yl)(5-methyl-2H-tetrazol-2-yl)methyl]piperidine
(3R)-3-[(R)-(1-fluoronaphthalen-2-yl)(5-phenyl-2H-tetrazol-2-yl)methyl]piperidine
(3S)-3-[(S)-(1-fluoronaphthalen-2-yl)(5-phenyl-2H-tetrazol-2-yl)methyl]piperidine
(3R)-3-[(S)-(1-fluoronaphthalen-2-yl)(5-phenyl-2H-tetrazol-2-yl)methyl]piperidine
(3S)-3-[(R)-(1-fluoronaphthalen-2-yl)(5-phenyl-2H-tetrazol-2-yl)methyl]piperidine
(3R)-3-[(R)-(6-fluoronaphthalen-2-yl)(5-methyl-2H-tetrazol-2-yl)methyl]piperidine
(3S)-1-butyl-3-[naphthalen-2-yl(2H-tetrazol-2-yl)methyl]piperidine
4-[(S)-naphthalen-2-yl(2H-tetrazol-2-yl)methyl]piperidine
4-[(R)-naphthalen-2-yl(2H-tetrazol-2-yl)methyl]piperidine
4-[(S)-naphthalen-2-yl(1H-tetrazol-2-yl)methyl]piperidine
4-[(R)-naphthalen-2-yl(1H-tetrazol-2-yl)methyl]piperidine
4-[(S)-(4-methylphenyl)(2H-tetrazol-2-yl)methyl]piperidine
4-[(R)-(4-methylphenyl)(2H-tetrazol-2-yl)methyl]piperidine
4-[(S)-(4-methylphenyl)(1H-tetrazol-2-yl)methyl]piperidine
4-[(R)-(4-methylphenyl)(1H-tetrazol-2-yl)methyl]piperidine
4-[(S)-naphthalen-2-yl(2H-1,2,3-triazol-2-yl)methyl]piperidine
4-[(R)-naphthalen-2-yl(2H-1,2,3-triazol-2-yl)methyl]piperidine
4-[(S)-naphthalen-2-yl(1H-1,2,3-triazol-2-yl)methyl]piperidine
4-[(R)-naphthalen-2-yl(1H-1,2,3-triazol-2-yl)methyl]piperidine
4-[(S)-(3,4-dichlorophenyl)(2H-tetrazol-2-yl)methyl]piperidine
4-[(R)-(3,4-dichlorophenyl)(2H-tetrazol-2-yl)methyl]piperidine A better understanding of the present invention may be obtained in light of following examples which are set forth to illustrate, but are not to be construed to limit, the present invention.

EXAMPLE 1

(3R)-3-[(R)-naphthalen-2-yl(2H-tetrazol-2-yl)methyl]piperidine

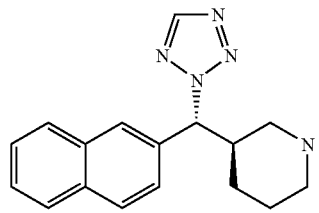 [SMILES: c1ccc2cc([C@@H]([C@@H]3CCCNC3)n3ncnn3)ccc2c1]

A mixture of 2-bromonaphthalene (4.59 mmol) and magnesium (5.508 mmol) was stirred vigorously in anhydrous THF (10 ml) under nitrogen atmosphere for 1 h to prepare naphthalen-2-ylmagnesium bromide solution. To this resulting solution was added tert-butyl(3R)-3-[methoxy(methyl)carbamoyl]piperidine-1-carboxylate (1.836 mmol) slowly at 0° C. After 10 min. the reaction mixture was warmed up to room temperature slowly and stirred for 2 hours. This solution was then quenched with aqueous $NH_4Cl$ (10 ml) and ethyl acetate (15 ml) was added. Organic layer was separated from aqueous layer, washed with brine. The combined organic layer was dried over anhydrous $MgSO_4$ and concentrated in vacuo.

The crude product was dissolved in anhydrous THF. To this solution was slowly added (S)-2-methyl-CBS-oxazaborolidine (1.0M in toluene, 0.5 equiv) at −78° C. After 5 min, borane-THF complex (3 equiv) was added slowly. The reaction mixture was then transferred into the freezer and left overnight. Chiral LC showed 9:1 ratio of the S to R isomer. The mixture was cooled to 0° C. and water was added dropwise to quench the reaction. The reaction mixture was diluted with ethyl acetate, washed with 5% aq NaOH, water, brine, and dried over $MgSO_4$. After concentration, the crude product was purified by flash column chromatography with a 4-35% ethyl acetate in hexanes gradient to afford (R)-tert-butyl 3-((S)-hydroxy(naphthyl)methyl)piperidine-1-carboxylate.

To a stirred solution of triphenylphosphine (2.754 mmol) and 1H-tetrazole (2.754 mmol) in THF (6 ml) was added previously prepared product (1.836 mmol) in THF (2 ml) at room temperature. The reaction mixture was stirred for 15 minutes, followed by the dropwise addition of diisopropyl azodicarboxylate (3.672 mmol) at 0° C. The solution was further stirred for 1 hour at room temperature. When the reaction was complete, the crude mixture was purified with silica gel chromatography (ethyl acetate:hexane=1:6).

The resulting product was dissolved in 6% HCl-MeOH solution and allowed to stir for 6 h. The solvent was removed under reduced pressure and basified with 1N NaOH to afford (3R)-3-[(R)-naphthalen-2-yl(2H-tetrazol-2-yl)methyl]piperidine.

1H-NMR (CDCl$_3$, 200 MHz), d8.5 (s, 1H), 8.0 (s, 1H), 7.8 (m, 4H), 7.5 (m, 2H), 6.0 (d, 1H), 3.0 (br, 2H), 2.5 (br, 3H), 1.5 (br, 3H), 1.2 (m, 2H)

EXAMPLE 2

(3S)-3-[(S)-naphthalen-2-yl(2H-tetrazol-2-yl)methyl]piperidine

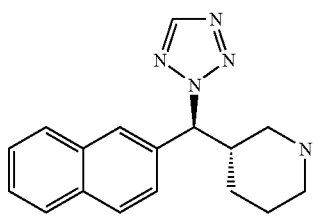 [SMILES: c1ccc2cc([C@H]([C@H]3CCCNC3)n3ncnn3)ccc2c1]

The procedure given in Example 1 was followed using tert-butyl(3S)-3-[methoxy(methyl)carbamoyl]piperidine-1-carboxylate as a reactant, instead of tert-butyl(3R)-3-[methoxy(methyl)carbamoyl]piperidine-1-carboxylate. As a reducing agent, (R)-2-methyl-CBS-oxazaborolidine was used instead of (S)-2-methyl-CBS-oxazaborolidine, to give (3S)-3-[(S)-naphthalen-2-yl(2H-tetrazol-2-yl)methyl]piperidine.

1H-NMR (CDCl$_3$, 200 MHz), d8.5 (s, 1H), 8.0 (s, 1H), 7.8 (m, 3H), 7.7 (m, 1H), 7.5 (m, 2H), 6.0 (d, 1H), 3.0 (br, 2H), 2.5 (br, 3H), 1.5 (br, 3H), 1.2 (m, 2H)

EXAMPLE 3

(3R)-3-[(S)-naphthalen-2-yl(2H-tetrazol-2-yl)methyl]piperidine

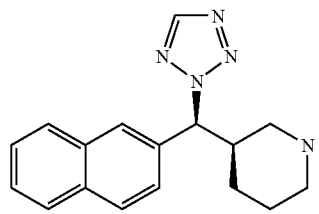 [SMILES: c1ccc2cc([C@H]([C@@H]3CCCNC3)n3ncnn3)ccc2c1]

The procedure given in Example 1 was followed using (R)-2-methyl-CBS-oxazaborolidine as a reducing agent, instead of (S)-2-methyl-CBS-oxazaborolidine, to give (3R)-3-[(S)-naphthalen-2-yl(2H-tetrazol-2-yl)methyl]piperidine hydrochloride.

1H-NMR (DMSO, 200 MHz), d9.1 (br, 1H), 8.2 (s, 1H), 8.0 (m, 3H), 7.7 (d, 1H), 7.6 (m, 2H), 6.2 (d, 1H), 2.8 (br, 2H), 2.5 (br, 3H), 1.6 (br, 2H), 1.3 (br, 3H)

EXAMPLE 4

(3S)-3-[(R)-naphthalen-2-yl(2H-tetrazol-2-yl)methyl]piperidine

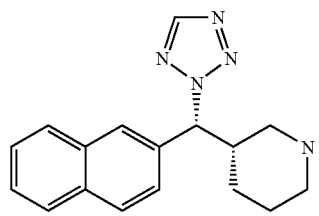 [SMILES: c1ccc2cc([C@@H]([C@H]3CCCNC3)n3ncnn3)ccc2c1]

The procedure given in Example 1 was followed using tert-butyl (3S)-3-[methoxy(methyl)carbamoyl]piperidine-1-carboxylate as a reactant, instead of tert-butyl(3R)-3-[methoxy(methyl)carbamoyl]piperidine-1-carboxylate, to give (3S)-3-[(R)-naphthalen-2-yl(2H-tetrazol-2-yl)methyl]piperidine hydrochloride.

1H-NMR (DMSO, 20 MHz), d9.1 (br, 1H), 8.2 (s, 1H), 8.0 (m, 3H), 7.7 (d, 1H), 7.6 (m, 2H), 6.2 (d, 1H), 2.8 (br, 2H), 2.5 (br, 3H), 1.6 (br, 2H), 1.3 (br, 3H)

EXAMPLE 5

(3R)-3-[(R)-naphthalen-2-yl(1H-tetrazol-1-yl)methyl]piperidine

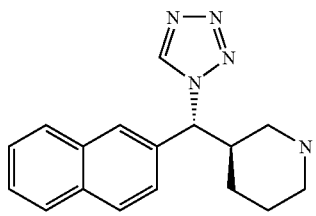 [SMILES: c1ccc2cc([C@@H]([C@@H]3CCCNC3)n3cnnn3)ccc2c1]

The procedure was given in Example 1 to give (3R)-3-[(R)-naphthalen-2-yl(1H-tetrazol-1-yl)methyl]piperidine.
1H-NMR (CDCl₃, 200 MHz), d9.0 (s, 1H), 7.8 (m, 4H), 7.5 (m, 3H), 5.8 (d, 1H), 4.8 (br, 1H), 3.0 (br, 4H), 2.5 (br, 1H), 1.6 (br, 3H)

EXAMPLE 6

(3S)-3-[(S)-naphthalen-2-yl(1H-tetrazol-1-yl)methyl]piperidine

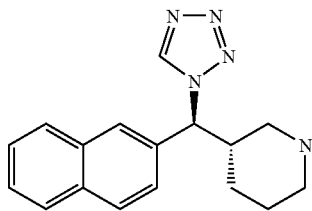 [SMILES: c1ccc2cc([C@H]([C@H]3CCCNC3)n3cnnn3)ccc2c1]

The procedure was given in Example 2 to give (3S)-3-[(S)-naphthalen-2-yl(1H-tetrazol-1-yl)methyl]piperidine.
1H-NMR (CDCl₃, 200 MHz), d9.0 (s, 1H), 7.8 (m, 4H), 7.5 (m, 3H), 5.8 (d, 1H), 4.8 (br, 1H), 3.0 (br, 4H), 2.5 (br, 1H), 1.6 (br, 3H)

EXAMPLE 7

(3R)-3-[(S)-naphthalen-2-yl(1H-tetrazol-1-yl)methyl]piperidine

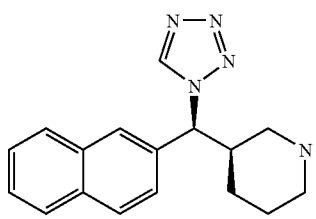 [SMILES: c1ccc2cc([C@H]([C@@H]3CCCNC3)n3cnnn3)ccc2c1]

The procedure was given in Example 3 to give (3R)-3-[(S)-naphthalen-2-yl(1H-tetrazol-1-yl)methyl]piperidine hydrochloride.
1H-NMR (DMSO, 200 MHz), d9.8 (s, 1H), 8.0 (m, 4H), 7.6 (m, 3H), 6.0 (d, 1H), 2.8 (br, 2H), 2.5 (br, 2H), 2.3 (m, 1H), 1.6 (br, 2H), 1.3 (br, 3H)

EXAMPLE 8

(3S)-3-[(R)-naphthalen-2-yl(1H-tetrazol-1-yl)methyl]piperidine

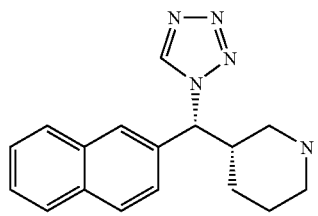 [SMILES: c1ccc2cc([C@@H]([C@H]3CCCNC3)n3cnnn3)ccc2c1]

The procedure was given in Example 4 to give (3S)-3-[(R)-naphthalen-2-yl(1H-tetrazol-1-yl)methyl]piperidine hydrochloride.
1H-NMR (DMSO, 200 MHz), d9.8 (s, 1H), 8.0 (m, 4H), 7.6 (m, 3H), 6.0 (d, 1H), 2.8 (br, 2H), 2.5 (br, 2H), 2.3 (m, 1H), 1.6 (br, 2H), 1.3 (br, 3H)

EXAMPLE 9

(3S)-3-[(R)-(5-methyl-2H-tetrazol-2-yl)(naphthalen-2-yl)methyl]piperidine

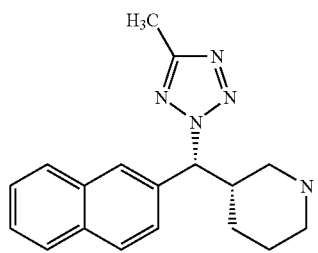 [SMILES: Cc1nnn([C@@H](c2ccc3ccccc3c2)[C@H]2CCCNC2)n1]

The procedure given in Example 1 was followed using, 5-methyl-1H-tetrazole as a reactant, instead of 1H-tetrazole. Also, as a reactant, tert-butyl(3S)-3-[methoxy(methyl)carbamoyl]piperidine-1-carboxylate was used instead of tert-butyl(3R)-3-[methoxy(methyl)carbamoyl]piperidine-1-carboxylate to give (3S)-3-[(R)-(5-methyl-2H-tetrazol-2-yl)(naphthalen-2-yl)methyl]piperidine.

1H-NMR (CDCl₃, 200 MHz), d8.0 (m, 1H), 7.8 (br, 3H), 7.7 (m, 1H), 7.5 (m, 2H), 5.8 (d, 1H), 2.9 (br, 2H), 2.8 (br, 2H), 2.5 (d, 3H), 2.4 (m, 1H), 1.7 (br, 1H), 1.5 (br, 2H), 1.2 (br, 2H)

EXAMPLE 10

(3S)-3-[(S)-(5-methyl-2H-tetrazol-2-yl)(naphthalen-2-yl)methyl]piperidine

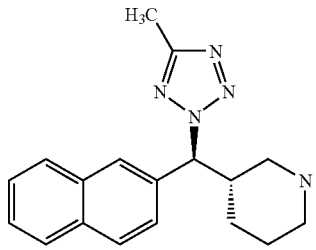 [SMILES: Cc1nnn([C@H](c2ccc3ccccc3c2)[C@H]2CCCNC2)n1]

The procedure given in Example 1 was followed using tert-butyl (3S)-3-[methoxy(methyl)carbamoyl]piperidine-1-carboxylate was used instead of tert-butyl(3R)-3-[methoxy(methyl)carbamoyl]piperidine-1-carboxylate. As a reducing agent, (R)-2-methyl-CBS-oxazaborolidine was used instead of (S)-2-methyl-CBS-oxazaborolidine. And 5-methyl-1H-tetrazole was used as a reactant, instead of 1H-tetrazole, to give (3S)-3-[(S)-(5-methyl-2H-tetrazol-2-yl)(naphthalen-2-yl)methyl]piperidine.

1H-NMR (CDCl₃, 200 MHz), d7.9 (br, 4H), 7.7 (m, 1H), 7.5 (m, 2H), 5.8 (d, 1H)

EXAMPLE 11

(3R-3-[(S)-(5-methyl-2H-tetrazol-2-yl)(naphthalen-2-yl)methyl]piperidine

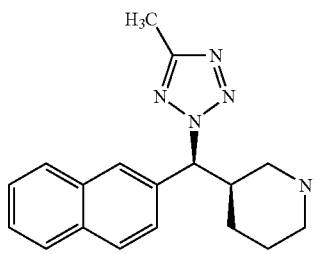 [SMILES: Cc1nnn([C@H](c2ccc3ccccc3c2)[C@@H]2CCCNC2)n1]

The procedure given in Example 1 was followed using 5-methyl-1H-tetrazole as a reactant, instead of 1H-tetrazole. Also, as a reducing agent, (R)-2-methyl-CBS-oxazaborolidine was used instead of (S)-2-methyl-CBS-oxazaborolidine, to give (3R)-3-[(S)-(5-methyl-2H-tetrazol-2-yl)(naphthalen-2-yl)methyl]piperidine.

1H-NMR (CDCl₃, 200 MHz), d8.0 (s, 1H), 7.8 (br, 3H), 7.7 (d, 1H), 7.5 (m, 2H), 5.8 (d, 1H), 2.9 (br, 2H), 2.6 (br, 2H), 2.5 (d, 3H), 2.4 (m, 1H), 1.5 (m, 3H), 1.2 (m, 2H)

EXAMPLE 12

(3R)-3-[(R)-(5-methyl-2H-tetrazol-2-yl)(naphthalen-2-yl)methyl]piperidine

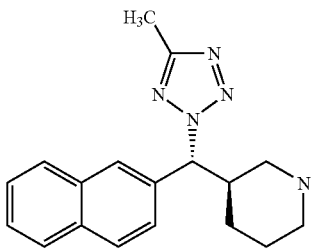 [SMILES: Cc1nnn([C@@H](c2ccc3ccccc3c2)[C@@H]2CCCNC2)n1]

The procedure given in Example 1 was followed using 5-methyl-1H-tetrazole as a reactant instead of 1H-tetrazole to give (3R)-3-[(R)-(5-methyl-2H-tetrazol-2-yl)(naphthalen-2-yl)methyl]piperidine.

1H-NMR (CDCl₃, 200 MHz), d7.9 (m, 5H), 7.7 (d, 1H), 7.5 (m, 2H), 5.8 (d, 1H), 3.0 (m, 3H), 2.6 (m, 1H), 2.5 (s, 3H), 2.4 (m, 1H), 1.5 (br, 5H)

EXAMPLE 13

(3R)-3-[(R)-naphthalen-2-yl(2H-1,2,3-triazol-2-yl)methyl]piperidine

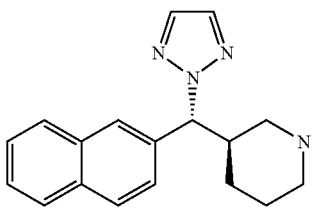 [SMILES: c1ccc2cc([C@@H]([C@@H]3CCCNC3)n3nccn3)ccc2c1]

The procedure given in Example 1 was followed using 1H-[1,2,3]-triazole as a reactant, instead of 1H-tetrazole to give (3R)-3-[(R)-naphthalen-2-yl(2H-1,2,3-triazol-2-yl)methyl]piperidine.

1H-NMR (CDCl₃, 200 MHz), d8.0 (s, 1H), 7.8 (d, 3H), 7.7 (d, 1H), 7.6 (s, 1H), 7.5 (m, 2H), 5.6 (d, 1H), 3.0 (m, 2H), 2.5 (m, 3H), 1.5 (br, 3H), 1.2 (m, 2H)

EXAMPLE 14

(3)-3-[(S)-naphthalen-2-yl(2H-1,2,3-triazol-2-yl)methyl]piperidine

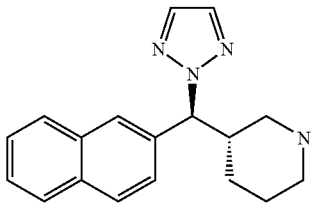

The procedure given in Example 1 was followed using tert-butyl(3S)-3-[methoxy(methyl)carbamoyl]piperidine-1-carboxylate was used instead of tert-butyl(3R)-3-[methoxy(methyl)carbamoyl]piperidine-1-carboxylate. As a reducing agent, (R)-2-methyl-CBS-oxazaborolidine was used instead of (S)-2-methyl-CBS-oxazaborolidine. And 1H-[1,2,3]-triazole was used as a reactant, instead of 1H-tetrazole, to give (3S)-3-[(S)-naphthalen-2-yl(2H-1,2,3-triazol-2-yl)methyl]piperidine.

1H-NMR (CDCl$_3$, 200 MHz), d8.0 (s, 1H), 7.8 (d, 3H), 7.7 (d, 1H), 7.6 (s, 1H), 7.5 (m, 2H), 5.6 (d, 1H), 3.0 (m, 2H), 2.5 (m, 3H), 1.5 (br, 3H), 1.2 (m, 2H)

EXAMPLE 15

(3R)-3-[(R)-(3,4-dichlorophenyl)(2H-tetrazol-2-yl)methyl]piperidine

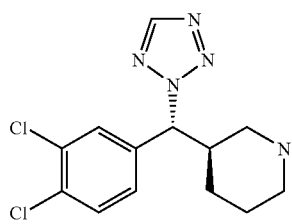 [SMILES: Clc1ccc([C@@H]([C@@H]2CCCNC2)n2ncnn2)cc1Cl]

The procedure given in Example 1 was followed using 4-bromo-1,2-diclorobenzene as a reactant, instead of 2-bromonaphthalene to give (3R)-3-[(R)-(3,4-dichlorophenyl)(2H-tetrazol-2-yl)methyl]piperidine.

1H-NMR (CDCl$_3$, 200 MHz), d8.5 (s, 1H), 7.6 (s, 1H), 7.4 (m, 2H), 5.8 (d, 1H), 3.0 (br, 1H), 2.6 (br, 3H), 2.3 (br, 1H), 1.6 (br, 3H), 1.2 (m, 2H)

EXAMPLE 16

(3S)-3-[(S)-(3,4-dichlorophenyl)(2H-tetrazol-2-yl)methyl]piperidine

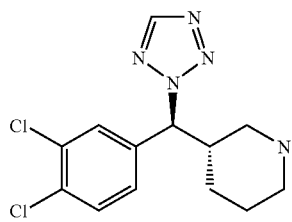

The procedure given in Example 2 was followed using 4-bromo-1,2-dichlorobenzene as a reactant, instead of 2-bromonaphthalene to give (3S)-3-[(S)-(3,4-dichlorophenyl)(2H-tetrazol-2-yl)methyl]piperidine.

1H-NMR (CDCl$_3$, 200 MHz), d8.5 (s, 1R), 7.6 (s, 1H), 7.4 (m, 2H), 5.8 (d, 1H), 3.0 (br, 1H), 2.6 (r, 3H), 2.3 (br, 1H), 1.6 (br, 3H), 1.2 (m, 2H)

EXAMPLE 17

(3R)-3-[(R)-(4-chlorophenyl)(2H-tetrazol-2-yl)methyl]piperidine

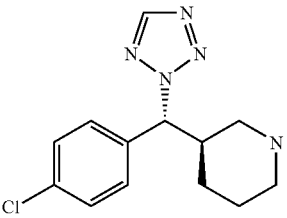 [SMILES: Clc1ccc([C@@H]([C@@H]2CCCNC2)n2ncnn2)cc1]

The procedure given in Example 1 was followed using 1-bromo-4-chlorobenzene as a reactant, instead of 2-bromonaphthalene to give (3R)-3-[(R)-(4-chlorophenyl)(2H-tetrazol-2-yl)methyl]piperidine.

1H-NMR (CDCl$_3$, 500 MHz), d8.5 (s, 1H), 7.6 (m, 2H), 7.4 (m, 2H), 5.8 (d, 1H), 3.0 (br, 1H), 2.8 (br, 2H), 2.7 (br, 1H), 2.4 (br, 1H), 1.7 (br, 1H), 1.6 (br, 1H), 1.5 (br, 1H), 1.4 (br, 1H), 1.2 (m, 1H)

EXAMPLE 18

(3S)-3-[(S)-(4-chlorophenyl)(2H-tetrazol-2-yl)methyl]piperidine

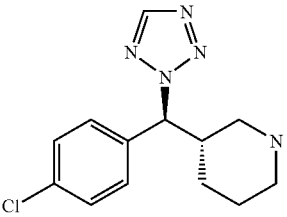 [SMILES: Clc1ccc([C@H]([C@H]2CCCNC2)n2ncnn2)cc1]

The procedure given in Example 2 was followed using 1-bromo-4-chlorobenzene as a reactant, instead of 2-bromonaphthalene to give (3S)-3-[(S)-(4-chlorophenyl)(2H-tetrazol-2-yl)methyl]piperidine.

1H-NMR (CDCl$_3$, 500 MHz), d8.5 (s, 1H), 7.6 (m, 2H), 7.4 (m, 2H), 5.8 (d, 1H), 3.0 (br, 1H), 2.8 (br, 2H), 2.7 (br, 1H), 2.4 (br, 1H), 1.7 (br, 1H), 1.6 (br, 1H), 1.5 (br, 1H), 1.4 (br, 1H), 1.2 (m, 1H)

EXAMPLE 19

(3R)-3-[(S)-(4-chlorophenyl)(2H-tetrazol-2-yl)methyl]piperidine

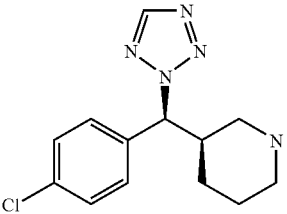 [SMILES: Clc1ccc([C@H]([C@@H]2CCCNC2)n2ncnn2)cc1]

The procedure given in Example 3 was followed using 1-bromo-4-chlorobenzene as a reactant, instead of 2-bromonaphthalene to give (3R)-3-[(S)-(4-chlorophenyl)(2H-tetrazol-2-yl)methyl]piperidine.

1H-NMR (CDCl₃, 500 MHz), d8.5 (s, 1H), 7.6 (m, 2H), 7.4 (m, 2H), 5.8 (d, 1H), 3.0 (br, 1H), 2.8 (br, 2H), 2.7 (br, 1H), 2.4 (br, 1H), 1.7 (br, 1H), 1.6 (br, 1H), 1.5 (br, 1H), 1.4 (br, 1H), 1.2 (m, 1H)

EXAMPLE 20

(3S)-3-[(R)-(4-chlorophenyl)(2H-tetrazol-2-yl)methyl]piperidine

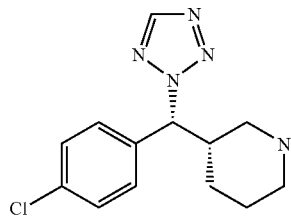 [SMILES: Clc1ccc([C@@H]([C@H]2CCCNC2)n2ncnn2)cc1]

The procedure given in Example 4 was followed using 1-bromo-4-chlorobenzene as a reactant, instead of 2-bromonaphthalene to give (3S)-3-[(R)-(4-chlorophenyl(2H-tetrazol-2-yl)methyl]piperidine.

1H-NMR (CDCl₃, 500 MHz), d8.5 (s, 1H), 7.6 (m, 2H), 7.4 (m, 2H), 5.8 (d, 1H), 3.0 (br, 1H), 2.8 (br, 2H), 2.7 (br, 1H), 2.4 (br, 1H), 1.7 (br, 1H), 1.6 (br, 1R), 1.5 (br, 1H), 1.4 (br, 1H), 1.2 (m, 1H)

EXAMPLE 21

(3R)-3-[(R)-naphthalen-1-yl(2H-tetrazol-2-yl)methyl]piperidine

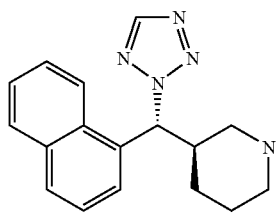 [SMILES: c1ccc2c([C@@H]([C@@H]3CCCNC3)n3ncnn3)cccc2c1]

The procedure given in Example 1 was followed using 1-bromonaphthalene as a reactant, instead of 2-bromonaphthalene, to give (3R)-3-[(R)-naphthalen-1-yl(2H-tetrazol-2-yl)methyl]piperidine.

1H-NMR (CDCl₃, 200 MHz), d8.5 (s, 1H), 8.4 (d, 1H), 8.0 (d, 1H), 7.9 (m, 2H), 7.6 (m, 3H), 6.8 (d, 1H), 3.2 (br, 3H), 2.6 (br, 2H), 1.6 (br, 3H), 1.2 (br, 2H)

EXAMPLE 22

(3S)-3-[(S)-naphthalen-1-yl(2H-tetrazol-2-yl)methyl]piperidine

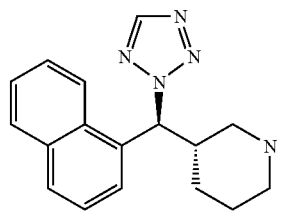 [SMILES: c1ccc2c([C@H]([C@H]3CCCNC3)n3ncnn3)cccc2c1]

The procedure given in Example 2 was followed using 1-bromonaphthalene as a reactant, instead of 2-bromonaphthalene, to give (3S)-3-[(S)-naphthalen-1-yl(2H-tetrazol-2-yl)methyl]piperidine.

1H-NMR (CDCl₃, 200 MHz), d8.5 (s, 1H), 8.4 (d, 1H), 8.0 (d, 1H), 7.9 (m, 2H), 7.6 (m, 3H), 6.8 (d, 1H), 3.2 (br, 3H), 2.6 (br, 2H), 1.6 (br, 3H), 1.2 (br, 2H)

EXAMPLE 23

(3R)-3-[(R)-(4-isopropylphenyl)(2H-tetrazol-2-yl)methyl]piperidine

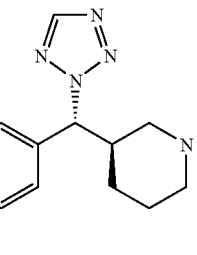

The procedure given in Example 1 was followed using 1-bromo-4-isopropylbenzene as a reactant, instead of 2-bromonaphthalene to give (3R)-3-[(R)-(4-isopropylphenyl)(2H-tetrazol-2-yl)methyl]piperidine.

1H-NMR (CDCl₃, 500 MHz), d8.5 (s, 1H), 7.4 (d, 2H), 7.2 (d, 2H), 5.7 (d, 1H), 3.2 (br, 1H), 3.0 (br, 1H), 2.9 (m, 2H), 2.6 (br, 2H), 1.7 (br, 3H), 1.2 (d, 6H), 1.1 (m, 1H)

EXAMPLE 24

(3S)-3-[(S)-(4-isopropylphenyl)(2H-tetrazol-2-yl)methyl]piperidine

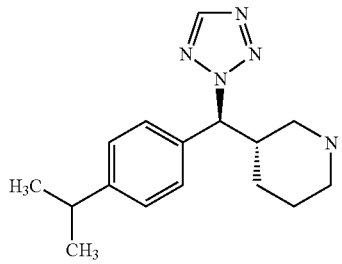 [SMILES: CC(C)c1ccc([C@H]([C@H]2CCCNC2)n2ncnn2)cc1]

The procedure given in Example 2 was followed using 1-bromo-4-isopropylbenzene as a reactant, instead of 2-bromonaphthalene to give (3S)-3-[(S)-(4-isopropylphenyl)(2H-tetrazol-2-yl)methyl]piperidine.

1H-NMR (CDCl$_3$, 500 MHz), d8.5 (s, 1H), 7.4 (d, 2H), 7.2 (d, 2H), 5.7 (d, 1H), 3.2 (br, 1H), 3.0 (br, 1H), 2.9 (m, 2H), 2.6 (br, 2H), 1.7 (br, 3H), 1.2 (d, 6H), 1.1 (m, 1H)

EXAMPLE 25

(3R)-3-[(S)-(4-isopropylphenyl)(2H-tetrazol-2-yl)methyl]piperidine

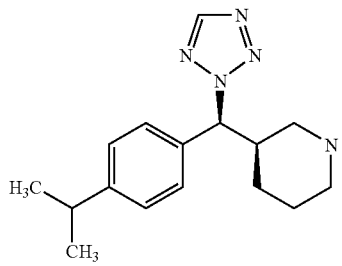 [SMILES: CC(C)c1ccc([C@H]([C@@H]2CCCNC2)n2ncnn2)cc1]

The procedure given in Example 3 was followed using 1-bromo-4-isopropylbenzene as a reactant, instead of 2-bromonaphthalene to give (3R)-3-[(S)-(4-isopropylphenyl)(2H-tetrazol-2-yl)methyl]piperidine.

1H-NMR (CDCl$_3$, 500 MHz), d8.5 (s, 1H), 7.5 (d, 2H), 7.2 (d, 2H), 5.7 (d, 1H), 4.0 (br, 1H), 3.0 (br, 1H), 2.8 (m, 3H), 2.6 (br, 1H), 2.4 (br, 1H), 1.7 (br, 1H), 1.5 (br, 1H), 1.3 (m, 2H), 1.2 (d, 6H), 1.1 (m, 1H)

EXAMPLE 26

(3S)-3-[(R)-(4-isopropylphenyl)(2H-tetrazol-2-yl)methyl]piperidine

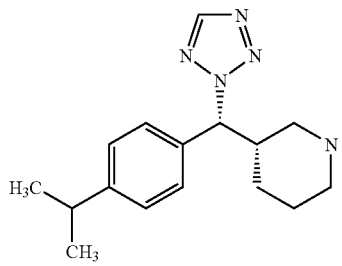 [SMILES: CC(C)c1ccc([C@@H]([C@H]2CCCNC2)n2ncnn2)cc1]

The procedure given in Example 4 was followed using 1-bromo-4-isopropylbenzene as a reactant, instead of 2-bromonaphthalene to give (3S)-3-[(R)-(4-isopropylphenyl)(2H-tetrazol-2-yl)methyl]piperidine.

1H-NMR (CDCl$_3$, 500 MHz), d8.5 (s, 1H), 7.5 (d, 2H), 7.2 (d, 2H), 5.7 (d, 1H), 4.0 (br, 1H), 3.0 (br, 1H), 2.8 (m, 3H), 2.6 (br, 1H), 2.4 (br, 1H), 1.7 (br, 1H), 1.5 (br, 1H), 1.3 (m, 2H), 1.2 (d, 6H), 1.1 (m, 1H)

EXAMPLE 27

(3S)-3-[(S)-(3,4-dimethoxyphenyl)(2H-tetrazol-2-yl)methyl]piperidine

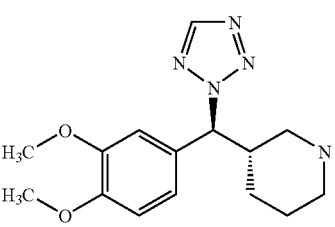 [SMILES: COc1ccc([C@H]([C@H]2CCCNC2)n2ncnn2)cc1OC]

The procedure given in Example 2 was followed using 4-bromo-1,2-dimethoxybenzene as a reactant instead of 2-bromonaphthalene to give (3S)-3-[(S)-(3,4-dimethoxyphenyl)(2H-tetrazol-2-yl)methyl]piperidine.

1H-NMR (CDCl$_3$, 200 MHz), d8.5 (s, 1H), 7.1 (d, 2H), 6.8 (d, 1H), 5.8 (d, 1H), 3.9 (d, 6H), 2.5 (br, 5H), 1.6 (br, 3H), 1.2 (br, 2H)

EXAMPLE 28

(3S)-3-[(R)-(3,4-dimethoxyphenyl)(2H-tetrazol-2-yl)methyl]piperidine

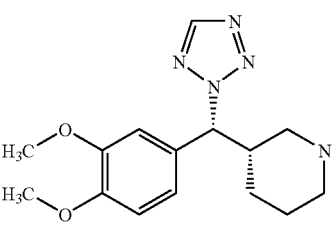 [SMILES: COc1ccc([C@@H]([C@H]2CCCNC2)n2ncnn2)cc1OC]

The procedure given in Example 4 was followed using 4-bromo-1,2-dimethoxybenzene as a reactant, instead of 2-bromonaphthalene to give (3S)-3-[(R)-(3,4-dimethoxyphenyl)(2H)-tetrazol-2-yl)methyl]piperidine.

1H-NMR (CDCl$_3$, 200 MHz), d8.5 (s, 1H), 7.1 (m, 2H), 6.8 (d, 1H), 5.7 (d, 1H), 3.9 (d, 1H), 2.8 (m, 4H), 2.4 (m, 1H), 1.5 (br, 3H), 1.2 (br, 2H)

EXAMPLE 29

(3S)-3-[(S)-(3,4-dimethoxyphenyl)(1H-tetrazol-1-yl)methyl]piperidine

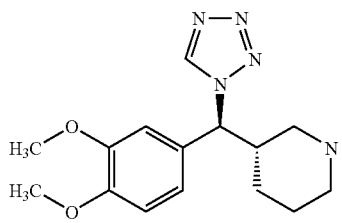 [SMILES: COc1ccc([C@H]([C@H]2CCCNC2)n2cnnn2)cc1OC]

The procedure was given in Example 27 to give (3S)-3-[(S)-(3,4-dimethoxyphenyl)(1H-tetrazol-1-yl)methyl]piperidine.

1H-NMR (CDCl₃, 200 MHz), d8.7 (s, 1H), 7.0 (br, 2H), 6.9 (d, 1H), 5.6 (d, 1H), 3.9 (d, 6H), 2.8 (br, 4H), 2.4 (br, 1H), 1.6 (br, 4H), 1.2 (br, 1H)

EXAMPLE 30

(3S)-3-[(R)-(3,4-dimethoxyphenyl)(1H-tetrazol-1-yl)methyl]piperidine

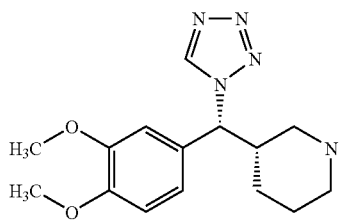 [SMILES: COc1ccc([C@@H]([C@H]2CCCNC2)n2cnnn2)cc1OC]

The procedure was given in Example 28 to give (3S)-3-[(R)-(3,4-dimethoxyphenyl)(1H-tetrazol-1-yl)methyl]piperidine.

1H-NMR (CDCl₃, 200 MHz), d8.6 (s, 1H), 7.0 (d, 2H), 6.8 (d, 2H), 5.4 (d, 1H), 3.9 (d, 6H), 2.8 (m, 4H), 2.4 (m, 1H), 1.6 (br, 4H), 1.1 (m, 1H)

EXAMPLE 31

(3S)-3-[(S)-phenyl(2H-tetrazol-2-yl)methyl]piperidine

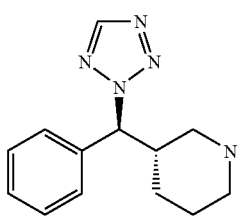 [SMILES: c1ccc([C@H]([C@H]2CCCNC2)n2ncnn2)cc1]

The procedure given in Example 2 was followed using bromobenzene as a reactant, instead of 2-bromonaphthalene to give (3S)-3-[(S)-phenyl(2H-tetrazol-2-yl)methyl]piperidine.

1H-NMR (CDCl₃, 200 MHz), d8.5 (s, 1N), 7.6 (m, 2H), 7.4 (m, 3H), 5.8 (d, 1H), 3.0 (m, 1H), 2.8 (m, 1H), 2.6 (m, 2H), 2.4 (m, 1H), 1.6 (br, 3H), 1.2 (m, 2H)

EXAMPLE 32

(3S)-3-[(R)-phenyl(2H-tetrazol-2-yl)methyl]piperidine

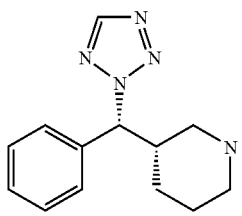 [SMILES: c1ccc([C@@H]([C@H]2CCCNC2)n2ncnn2)cc1]

The procedure given in Example 4 was followed using bromobenzene as a reactant, instead of 2-bromonaphthalene to give (3S)-3-[(R)-phenyl(2H-tetrazol-2-yl)methyl]piperidine.

1H-NMR (CDCl₃, 200 MHz), d8.5 (s, 1H), 7.6 (m, 2H), 7.4 (m, 3H), 5.8 (d, 1H), 3.0 (m, 1H), 2.8 (d, 2H), 2.6 (m, 1H), 2.4 (m, 1H), 1.7 (br, 1H), 1.5 (br, 1H), 1.3 (br, 2H), 1.2 (m, 1H)

EXAMPLE 33

(3S)-3-{(S)-2H-tetrazol-2-yl[4-(trifluoromethyl)phenyl]methyl}piperidine

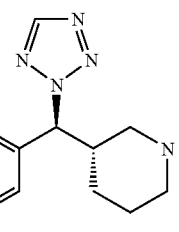

The procedure given in Example 2 was followed using 1-bromo-4-(trifluoromethyl)benzene as a reactant, instead of 2-bromonaphthalene to give (3S)-3-{(S)-2H-tetrazol-2-yl[4-(trifluoromethyl)phenyl]methyl}piperidine.

1H-NMR (CDCl₃, 200 MHz), d8.6 (s, 1H), 7.7 (m, 4H), 5.9 (d, 1H), 3.0 (br, 1R), 2.8 (br, 1H), 2.6 (br, 2H), 2.4 (br, 1H), 1.5 (br, 3H), 1.2 (br, 2H)

EXAMPLE 34

(3S)-3-{(R)-2H-tetrazol-2-yl[4-(trifluoromethyl)phenyl]methyl}piperidine

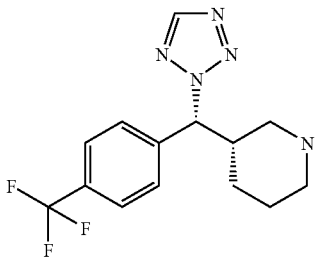 [SMILES: FC(F)(F)c1ccc([C@@H]([C@H]2CCCNC2)n2ncnn2)cc1]

The procedure given in Example 4 was followed using 1-bromo-4-(trifluoromethyl)benzene as a reactant, instead of 2-bromonaphthalene to give (3S)-3-{(R)-2H-tetrazol-2-yl[4-(trifluoromethyl)phenyl]methyl}piperidine.

1H-NMR (CDCl$_3$, 200 MHz), d8.5 (s, 1H), 7.7 (m, 4H), 5.9 (d, 1H), 3.0 (br, 1H), 2.8 (br, 3H), 2.4 (br, 1H), 1.7 (br, 2H), 1.4 (br, 2H), 1.2 (br, 1H)

EXAMPLE 35

(3S)-3-[(S)-(6-methoxynaphthalen-2-yl)(2H-tetrazol-2-yl)methyl]piperidine

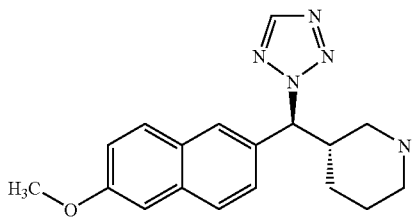 [SMILES: COc1ccc2cc([C@H]([C@H]3CCCNC3)n3ncnn3)ccc2c1]

The procedure given in Example 2 was followed using 2-bromo-6-methoxynaphthalene as a reactant, instead of 2-bromonaphthalene to give (3S)-3-[(E)-(6-methoxynaphthalen-2-yl)(2H-tetrazol-2-yl)methyl]piperidine.

1H-NMR (CDCl$_3$, 200 MHz), d8.5 (s, 1H), 7.9 (br, 1H), 7.7 (m, 3H), 7.2 (m, 2H), 5.9 (d, 1H), 3.9 (s, 1H), 3.0 (br, 2H), 2.6 (br, 3H), 1.6 (br, 3H), 1.2 (br, 2H)

EXAMPLE 36

(3S)-3-[(R)-(6-methoxynaphthalen-2-yl)(2H-tetrazol-2-yl)methyl]piperidine

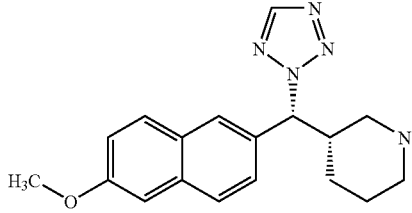 [SMILES: COc1ccc2cc([C@@H]([C@H]3CCCNC3)n3ncnn3)ccc2c1]

The procedure given in Example 4 was followed using 2-bromo-6-methoxynaphthalene as a reactant, instead of 2-bromonaphthalene to give (3S)-3-[(R)-(6-methoxynaphthalen-2-yl)(2H-tetrazol-2-yl)methyl]piperidine.

1H-NMR (CDCl$_3$, 200 MHz), d8.5 (s, 1H), 7.9 (s, 1H), 7.7 (m, 3H), 7.2 (m, 2H), 5.9 (d, 1H), 3.9 (s, 1H), 3.0 (br, 2H), 2.5 (br, 3H), 1.4 (br, 5H)

EXAMPLE 37

(3S)-3-[(S)-(4-methylphenyl)(2H-tetrazol-2-yl)methyl]piperidine

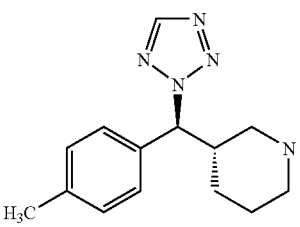 [SMILES: Cc1ccc([C@H]([C@H]2CCCNC2)n2ncnn2)cc1]

The procedure given in Example 2 was followed using 1-bromo-4-methylbenzene as a reactant, instead of 2-bromonaphthalene to give (3S)-3-[(S)-(4-methylphenyl)(2H-tetrazol-2-yl)methyl]piperidine.

1H-NMR (CDCl$_3$, 200 MHz), d8.5 (s, 1H), 7.4 (d, 2H), 7.2 (d, 2H), 5.7 (d, 1H), 3.0 (br, 1H), 2.8 (br, 1H), 2.6 (br, 3H), 2.3 (s, 3H), 1.6 (br, 3H), 1.2 (br, 2H)

EXAMPLE 38

(3S)-3-[(R)-(4-methylphenyl)(2H-tetrazol-2-yl)methyl]piperidine

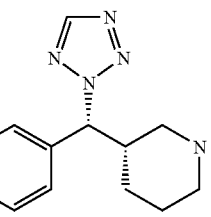

The procedure given in Example 4 was followed using 1-bromo-4-methylbenzene as a reactant, instead of 2-bromonaphthalene to give (3S)-3-[(R)-(4-methylphenyl)(2H-tetrazol-2-yl)methyl]piperidine.

1H-NMR (CDCl$_3$, 200 MHz), d8.5 (s, 1H), 7.4 (d, 2H), 7.2 (d, 2H), 5.7 (d, 1H), 3.0 (br, 1H), 2.7 (br, 4H), 2.3 (s, 3H), 1.6 (br, 2H), 1.4 (br, 1H), 1.2 (br, 2H)

EXAMPLE 39

(3S)-3-[(S)-(3-chlorophenyl)(2H-tetrazol-2-yl)methyl]piperidine

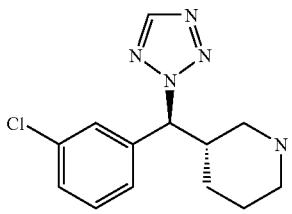 [SMILES: Clc1cccc([C@H]([C@H]2CCCNC2)n2ncnn2)c1]

The procedure given in Example 2 was followed using 1-bromo-3-chlorobenzene as a reactant, instead of 2-bromonaphthalene to give (3S)-3-[(S)-(3-chlorophenyl)(2H-tetrazol-2-yl)methyl]piperidine.

1H-NMR (CDCl$_3$, 200 MHz), d8.5 (s, 1H), 7.6 (s, 1H), 7.4 (m, 1H), 7.3 (m, 2H), 5.8 (d, 1H), 3.0 (br, 1H), 2.7 (m, 3H), 2.4 (m, 1H), 2.2 (br, 1H), 1.6 (br, 3H), 1.2 (m, 1H)

EXAMPLE 40

(3S)-3-[(R)-(3-chlorophenyl)(2H-tetrazol-2-yl)methyl]piperidine

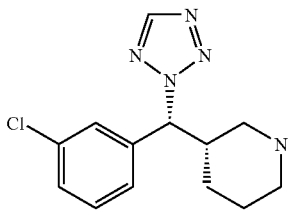 [SMILES: Clc1cccc([C@@H]([C@H]2CCCNC2)n2ncnn2)c1]

The procedure given in Example 4 was followed using 1-bromo-3-chlorobenzene as a reactant, instead of 2-bromonaphthalene to give (3S)-3-[(R)-(3-chlorophenyl)(2H-tetrazol-2-yl)methyl]piperidine.

1H-NMR (CDCl$_3$, 200 MHz), d8.5 (s, 1H), 7.6 (s, 1H), 7.4 (m, 1H), 7.3 (m, 2H), 5.8 (d, 1H), 3.0 (m, 1H), 2.7 (m, 3H), 2.4 (m, 1H), 1.7 (br, 2H), 1.4 (m, 2H), 1.2 (m, 1H)

EXAMPLE 41

(3S)-3-[(S)-(2,4-difluorophenyl)(2H-tetrazol-2-yl)methyl]piperidine

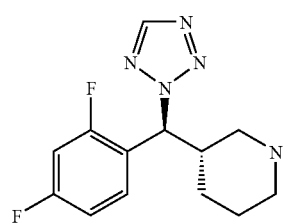 [SMILES: Fc1ccc([C@H]([C@H]2CCCNC2)n2ncnn2)c(F)c1]

The procedure given in Example 2 was followed using 1-bromo-2,4-difluorobenzene as a reactant, instead of 2-bromonaphthalene to give (3S)-3-[(S)-(2,4-difluorophenyl)(2H-tetrazol-2-yl)methyl]piperidine.

1H-NMR (CDCl$_3$, 200 MHz), d8.5 (s, 1H), 7.7 (m, 1H), 6.9 (m, 2H), 6.2 (d, 1H), 3.0 (br, 1H), 2.5 (br, 4H), 1.7 (br, 3H), 1.4 (br, 1H), 1.2 (br, 1H)

EXAMPLE 42

(3S)-3-[(R)-(2,4-difluorophenyl)(2H-tetrazol-2-yl)methyl]piperidine

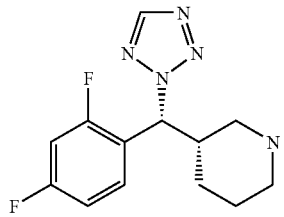 [SMILES: Fc1ccc([C@@H]([C@H]2CCCNC2)n2ncnn2)c(F)c1]

The procedure given in Example 4 was followed using 1-bromo-2,4-difluorobenzene as a reactant, instead of 2-bromonaphthalene to give (3S)-3-[(R)-(2,4-difluorophenyl)(2H-tetrazol-2-yl)methyl]piperidine.

1H-NMR (CDCl$_3$, 200 MHz), d8.5 (s, 1H), 7.8 (m, 1H), 6.9 (m, 2H), 6.2 (d, 1H), 3.0 (m, 1H), 2.7 (m, 3H), 2.4 (m, 1H), 2.0 (br, 1H), 1.7 (br, 1H), 1.5 (br, 1H), 1.2 (m, 2H)

EXAMPLE 43

(3S)-3-[(S)-(4-methoxyphenyl)(2H-tetrazol-2-yl)methyl]piperidine

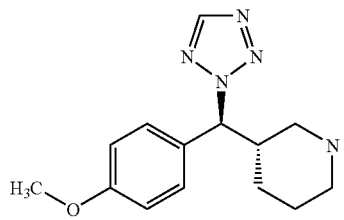 [SMILES: COc1ccc([C@H]([C@H]2CCCNC2)n2ncnn2)cc1]

The procedure given in Example 2 was followed using 1-bromo-4-methoxybenzene as a reactant, instead of 2-bromonaphthalene to give (3S)-3-[(S)-(4-methoxyphenyl)(2H-tetrazol-2-yl)methyl]piperidine.

1H-NMR (CDCl$_3$, 200 MHz), d8.5 (s, 1H), 7.5 (d, 2H), 6.9 (d, 2H), 5.7 (d, 1H), 3.8 (s, 3H), 3.0 (br, 1H), 2.6 (br, 4H), 1.6 (br, 4H), 1.2 (br, 1H)

EXAMPLE 44

(3S)-3-[(R)-(4-methoxyphenyl)(2H-tetrazol-2-yl)methyl]piperidine

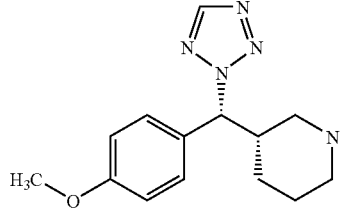 [SMILES: COc1ccc([C@@H]([C@H]2CCCNC2)n2ncnn2)cc1]

The procedure given in Example 4 was followed using 1-bromo-4-methoxybenzene as a reactant, instead of 2-bromonaphthalene to give (3S)-3-[(R)-(4-methoxyphenyl)(2H-tetrazol-2-yl)methyl]piperidine.

1H-NMR (CDCl₃, 200 MHz), d8.5 (s, 1H), 7.5 (d, 2H), 6.9 (d, 2H), 5.7 (d, 1H), 3.8 (s, 3H), 2.8 (br, 4H), 2.3 (br, 1H), 1.8 (br, 2H), 1.3 (br, 3H)

EXAMPLE 45

(3S)-3-[(S)-(4-methoxyphenyl)(1H-tetrazol-1-yl)methyl]piperidine

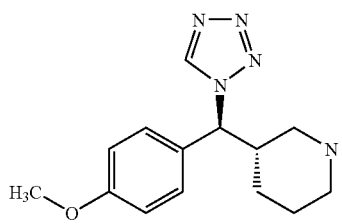 [SMILES: COc1ccc([C@H]([C@H]2CCCNC2)n2cnnn2)cc1]

The procedure was given in Example 43 to give (3S)-3-[(S)-(4-methoxyphenyl)(1H-tetrazol-1-yl)methyl]piperidine.

1H-NMR (CDCl₃, 200 MHz), δ8.5 (s, 1H), 7.4 (d, 2H), 6.9 (d, 2H), 5.5 (d, 1H), 3.8 (s, 3H), 2.9 (br, 1H), 2.7 (br, 3H), 2.3 (br, 1H), 1.6 (br, 4H), 1.2 (br, 1H)

EXAMPLE 46

(3S)-3-[(R)-(4-methoxyphenyl)(1H-tetrazol-1-yl)methyl]piperidine

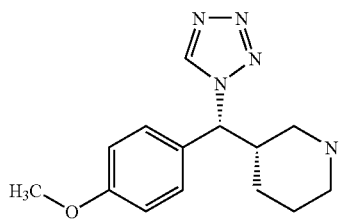 [SMILES: COc1ccc([C@@H]([C@H]2CCCNC2)n2cnnn2)cc1]

The procedure was given in Example 44 to give (3S)-3-[(R)-(4-methoxyphenyl)(1H-tetrazol-1-yl)methyl]piperidine.

1H-NMR (CDCl₃, 200 MHz), δ8.6 (s, 1H), 7.4 (d, 2H), 6.9 (d, 2H), 5.4 (d, 1H), 3.8 (s, 3H), 2.8 (br, 4H), 2.4 (br, 1H), 1.8 (br, 2H), 1.5 (br, 2H), 1.1 (br, 1H)

EXAMPLE 47

(3S)-3-[(S)-(4-phenoxyphenyl)(2H-tetrazol-2-yl)methyl]piperidine

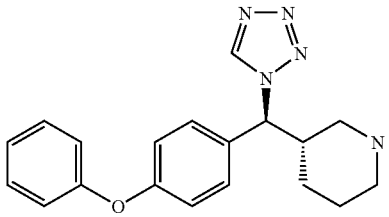 [SMILES: c1ccc(Oc2ccc([C@H]([C@H]3CCCNC3)n3cnnn3)cc2)cc1]

The procedure given in Example 2 was followed using 1-bromo-4-phenoxybenzene as a reactant, instead of 2-bromonaphthalene to give (3S)-3-[(S)-(4-phenoxyphenyl)(9H-tetrazol-2-yl)methyl]piperidine.

1H-NMR (CDCl₃, 500 MHz), δ8.6 (s, 1H), 7.5 (d, 2H), 7.4 (m, 3H), 7.2 (m, 1), 7.0 (m, 5H), 5.8 (d, 1H), 3.0 (br, 1H), 2.8 (br, 1H), 2.6 (br, 1H), 2.5 (br, 1H), 2.4 (br, 1H), 1.6 (br, 3H), 1.5 (br, 1H), 1.2 (m, 1H)

EXAMPLE 48

(3S)-3-[(R)-(4-phenoxyphenyl)(2H-tetrazol-2-yl)methyl]piperidine

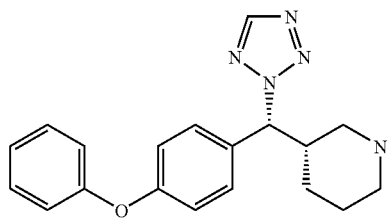 [SMILES: c1ccc(Oc2ccc([C@@H]([C@H]3CCCNC3)n3ncnn3)cc2)cc1]

The procedure given in Example 4 was followed using 1-bromo-4-phenoxybenzene as a reactant, instead of 2-bromonaphthalene to give (3S)-3-[(R)-(4-phenoxyphenyl)(2H-tetrazol-2-yl)methyl]piperidine.

1H-NMR (CDCl₃, 500 MHz), δ8.5 (s, 1H), 7.6 (d, 2H), 7.4 (m, 3H), 7.1 (m, 1H), 7.0 (m, 5H), 5.8 (d, 1H), 3.0 (br, 1H), 2.9 (d, 1H), 2.8 (d, 1H), 2.7 (br, 1H), 2.4 (br, 1H), 1.7 (br, 2H), 1.5 (br, 1H), 1.3 (br, 1H), 1.1 (m, 1H)

EXAMPLE 49

(3S)-3-[(S)-(4-phenoxyphenyl)(1H-tetrazol-1-yl)methyl]piperidine

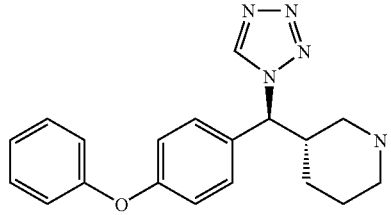 [SMILES: c1ccc(Oc2ccc([C@H]([C@H]3CCCNC3)n3cnnn3)cc2)cc1]

The procedure was given in Example 47 to give (3S)-3-[(S)-(4-phenoxyphenyl)(1H-tetrazol-1-yl)methyl]piperidine.

1H-NMR (CDCl₃, 500 MHz), δ8.7 (s, 1H), 7.4 (m, 5H), 7.2 (m, 1H), 7.0 (m, 5H), 5.6 (d, 1H), 2.9 (br, 1H), 2.8 (br, 3H), 2.4 (br, 1H), 1.7 (br, 2H), 1.5 (br, 2H), 1.2 (br, 1H)

EXAMPLE 50

(3S)-3-[(R)-(4-phenoxyphenyl)(1H-tetrazol-1-yl)methyl]piperidine

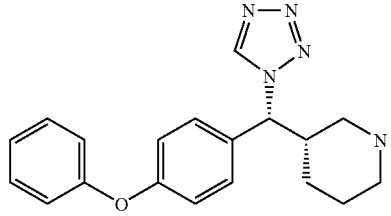 [SMILES: c1ccc(Oc2ccc([C@@H]([C@H]3CCCNC3)n3cnnn3)cc2)cc1]

The procedure was given in Example 48 to give (3S)-3-[(R)-(4-phenoxyphenyl)(1H-tetrazol-1-yl)methyl]piperidine.

1H-NMR (CDCl₃, 500 MHz), δ8.6 (s, 1H), 7.4 (m, 5H), 7.2 (m, 1H), 7.0 (m, 5H), 5.4 (d, 1H), 3.0 (br, 1H), 2.9 (br, 1H), 2.7 (br, 2H), 2.4 (br, 1H), 1.7 (br, 2H), 1.5 (br, 2H), 1.2 (br, 1H)

EXAMPLE 51

(3S)-3-[(S)-(4-fluorophenyl)(2H-tetrazol-2-yl)methyl]piperidine

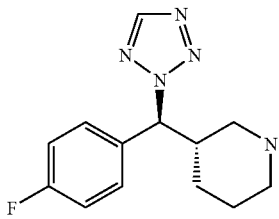 [SMILES: Fc1ccc([C@H]([C@H]2CCCNC2)n2ncnn2)cc1]

The procedure given in Example 2 was followed using 1-bromo-4-fluorobenzene as a reactant, instead of 2-bromonaphthalene to give (3S)-3-[(S)-(4-fluorophenyl)(2H-tetrazol-2-yl)methyl]piperidine.

1H-NMR (CDCl₃, 200 MHz), δ8.5 (s, 1H), 7.6 (m, 2H), 7.0 (t, 2H), 5.8 (d, 1H), 2.9 (br, 1H), 2.5 (br, 4H), 1.6 (br, 4H), 1.2 (br, 1H)

EXAMPLE 52

(3S)-3-[(R)-(4-fluorophenyl)(2H-tetrazol-2-yl)methyl]piperidine

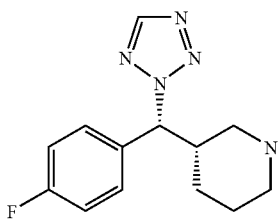 [SMILES: Fc1ccc([C@@H]([C@H]2CCCNC2)n2ncnn2)cc1]

The procedure given in Example 4 was followed using 1-bromo-4-fluorobenzene as a reactant, instead of 2-bromonaphthalene to give (3S)-3-[(R)-(4-fluorophenyl)(2H-tetrazol-2-yl)methyl]piperidine.

1H-NMR (CDCl₃, 200 MHz), δ8.5 (s, 1H), 7.6 (m, 2H), 7.0 (t, 2H), 5.8 (d, 1H), 2.9 (br, 1H 2.7 (br, 3H), 2.4 (br, 1H), 1.7 (br, 2H), 1.3 (br, 3H)

EXAMPLE 53

(3S)-3-[(S)-biphenyl-4-yl(2H-tetrazol-2-yl)methyl]piperidine

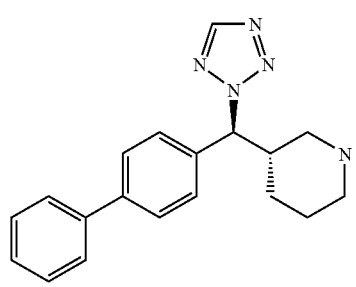 [SMILES: c1ccc(-c2ccc([C@H]([C@H]3CCCNC3)n3ncnn3)cc2)cc1]

The procedure given in Example 2 was followed using 4-bromobiphenyl as a reactant, instead of 2-bromonaphthalene to give (3S)-3-[(S)-biphenyl-4-yl(2H-tetrazol-2-yl)methyl]piperidine, 1H-NMR (CDCl₃, 200 MHz), δ8.5 (s, 1H), 7.5 (m, 11H), 5.9 (d, 1H), 3.0 (br, 4H), 2.6 (br, 2H), 1.7 (br, 2H), 1.3 (br, 2H)

EXAMPLE 54

(3S)-3-[(R)-biphenyl-4-yl(2H-tetrazol-2-yl)methyl]piperidine

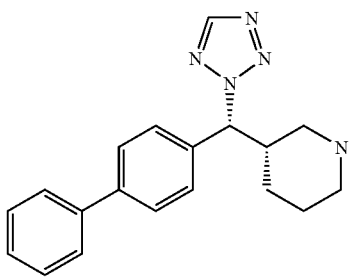 [SMILES: c1ccc(-c2ccc([C@@H]([C@H]3CCCNC3)n3ncnn3)cc2)cc1]

The procedure given in Example 4 was followed using 4-bromobiphenyl as a reactant, instead of 2-bromonaphthalene to give (3S)-3-[(R)-biphenyl-4-yl(2H-tetrazol-2-yl)methyl]piperidine.

1H-NMR (CDCl₃, 200 MHz), δ8.5 (s, 1H), 7.5 (m, 11H), 5.8 (d, 1H), 3.0 (br, 4H), 2.6 (br, 2H), 1.7 (br, 2H), 1.2 (br, 2H)

EXAMPLE 55

(3S)-3-{(S)-2H-tetrazol-2-yl[3-(trifluoromethyl)phenyl]methyl}piperidine

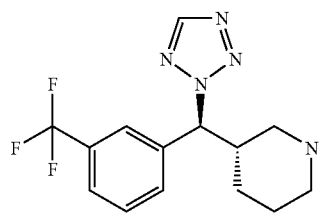 [SMILES: FC(F)(F)c1cccc([C@H]([C@H]2CCCNC2)n2ncnn2)c1]

The procedure given in Example 2 was followed using 1-bromo-3-(trifluoromethyl)benzene as a reactant, instead of 2-bromonaphthalene to give (3S)-3-{(S)-2H-tetrazol-2-yl[3-(trifluoromethyl)phenyl]methyl}piperidine.

1H-NMR (CDCl₃, 500 MHz), δ8.5 (s, 1H), 7.8 (d, 2H), 7.6 (m, 2H), 5.9 (d, 1H), 3.0 (br, 1H), 2.8 (m, 1H), 2.7 (m, 1H), 2.6 (m, 1H), 2.4 (m, 1H), 1.8 (br, 1H), 1.7 (br, 1H), 1.6 (br, 1H), 1.5 (m, 1H), 1.2 (m, 1H)

EXAMPLE 56

(3S)-3-{(R)-2H-tetrazol-2-yl[3-(trifluoromethyl)phenyl]methyl}piperidine

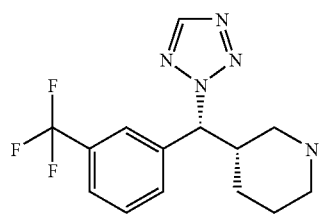 [SMILES: FC(F)(F)c1cccc([C@@H]([C@H]2CCCNC2)n2ncnn2)c1]

The procedure given in Example 4 was followed using 1-bromo-3-(trifluoromethyl)benzene as a reactant, instead of 2-bromonaphthalene to give (3S)-3-{(R)-2H-tetrazol-2-yl[3-(trifluoromethyl)phenyl]methyl}piperidine.

1H-NMR (CDCl₃, 500 MHz), δ8.5 (s, 1H), 7.8 (d, 2H), 7.6 (d, 1H), 7.5 (m, 1H), 5.9 (d, 1H), 3.0 (br, 1H), 2.8 (m, 2H), 2.7 (m, 1H), 2.4 (m, 1H), 1.7 (br, 2H), 1.5 (br, 1H), 1.3 (br, 1H), 1.1 (br, 1H)

EXAMPLE 57

(3S)-3-[(S)-(4-propylphenyl)(2H-tetrazol-2-yl)methyl]piperidine

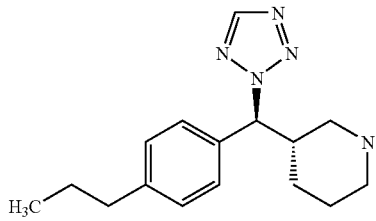 [SMILES: CCCc1ccc([C@H]([C@H]2CCCNC2)n2ncnn2)cc1]

The procedure given in Example 2 was followed using 1-bromo-4-propylbenzene as a reactant instead of 2-bromonaphthalene to give (3S)-3-[(S)-(4-propylphenyl)(2H-tetrazol-2-yl)methyl]piperidine.

1H-NMR (CDCl₃, 500 MHz), δ8.5 (s, 1H), 7.5 (br, 2H), 7.2 (br, 2H), 5.8 (d, 1H), 3.0 (br, 1H), 2.8 (br, 1H), 2.6 (br, 4H), 2.4 (br, 1H), 1.6 (br, 5H), 1.5 (br, 1H), 1.1 (br, 1H), 1.0 (t, 3H)

EXAMPLE 58

(3S)-3-[(R)-(4-propylphenyl)(2H-tetrazol-2-yl)methyl]piperidine

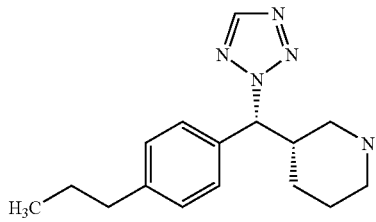 [SMILES: CCCc1ccc([C@@H]([C@H]2CCCNC2)n2ncnn2)cc1]

The procedure given in Example 4 was followed using 1-bromo-4-propylbenzene as a reactant, instead of 2-bromonaphthalene to give (3S)-3-[(R)-(4-propylphenyl)(2H-tetrazol-2-yl)methyl]piperidine.

1H-NMR (CDCl₃, 500 MHz), δ8.5 (s, 1H), 7.5 (d, 2H), 7.2 (d, 2H), 5.7 (d, 1H), 3.0 (br, 1H), 2.8 (br, 2H), 2.6 (br, 3H), 2.4 (br, 1H), 1.7 (br, 3H), 1.5 (br, 1H), 1.3 (br, 1H), 1.1 (br, 1H), 1.0 (t, 3H)

EXAMPLE 59

(3S)-3-[(S)-(4-methylnaphthalen-1-yl)(2H-tetrazol-2-yl)methyl]piperidine

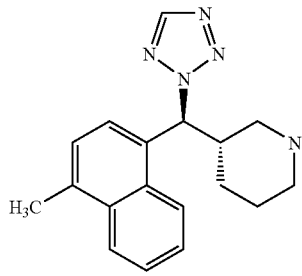 [SMILES: Cc1ccc([C@H]([C@H]2CCCNC2)n2ncnn2)c2ccccc12]

The procedure given in Example 2 was followed using 1-bromo-4-methylnaphthalene as a reactant, instead of 2-bromonaphthalene to give (3S)-3-[(S)-(4-methylnaphthalen-1-yl)(2H-tetrazol-2-yl)methyl]piperidine.

1H-NMR (CDCl₃, 500 MHz), δ8.5 (s, 1H), 8.4 (d, 1H), 8.1 (d, 1H), 7.9 (d, 1H), 7.6 (m, 2H), 7.4 (d, 1H), 6.8 (d, 1H), 3.1 (br, 2H), 2.7 (s, 3H), 2.6 (br, 3H), 2.5 (br, 1H), 1.7 (br, 2H), 1.5 (br, 1H), 1.2 (m, 1H)

EXAMPLE 60

(3S)-3-[(R)-(4-methylnaphthalen-1-yl)(2H-tetrazol-2-yl)methyl]piperidine

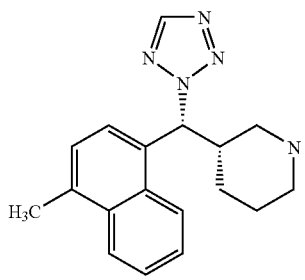 [SMILES: Cc1ccc([C@@H]([C@H]2CCCNC2)n2ncnn2)c2ccccc12]

The procedure given in Example 4 was followed using 1-bromo-4-methylnaphthalene as a reactant, instead of 2-bromonaphthalene to give (3S)-3-[(R)-(4-methylnaphthalen-1-yl)(2H-tetrazol-2-yl)methyl]piperidine.

1H-NMR (CDCl₃, 500 MHz), δ8.5 (s, 1H), 8.4 (d, 1H), 8.1 (d, 1H), 8.0 (d, 1H), 7.6 (m, 2H), 7.4 (d, 1H), 6.8 (d, 1H), 3.1 (br, 2H), 2.9 (br, 1H), 2.7 (s, 3H), 2.6 (br, 1H), 2.4 (br, 1H), 2.2 (br, 1H), 1.8 (br, 1H), 1.6 (br, 1H), 1.3 (m, 2H)

EXAMPLE 61

(3S)-3-[(S)-(3-methylphenyl)(2H-tetrazol-2-yl)methyl]piperidine

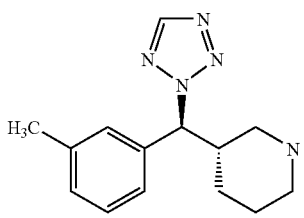 [SMILES: Cc1cccc([C@H]([C@H]2CCCNC2)n2ncnn2)c1]

The procedure given in Example 2 was followed using 1-bromo-3-methylbenzene as a reactant, instead of 2-bromonaphthalene to give (3S)-3-[(S)-(3-methylphenyl)(2H-tetrazol-2-yl)methyl]piperidine.

1H-NMR (CDCl₃, 500 MHz), δ8.5 (s, 1H), 7.4 (s, 2H), 7.3 (t, 1H), 7.1 (d, 1H), 5.7 (d, 1H), 3.0 (br, 1H), 2.8 (br, 1H), 2.6 (br, 1H), 2.4 (br, 1H), 2.3 (s, 3H), 1.7 (br, 1H), 1.6 (br, 1H), 1.4 (br, 1H), 1.1 (m, 1H)

EXAMPLE 62

(3S)-3-[(R)-(3-methylphenyl)(2H-tetrazol-2-yl)methyl]piperidine

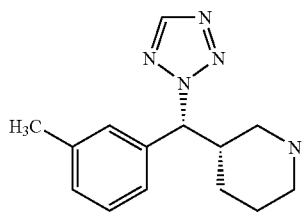 [SMILES: Cc1cccc([C@@H]([C@H]2CCCNC2)n2ncnn2)c1]

The procedure given in Example 4 was followed using 1-bromo-3-methylbenzene as a reactant, instead of 2-bromonaphthalene to give ((3S)-3-[(R)-(3-methylphenyl)(2H-tetrazol-2-yl)methyl]piperidine.

1H-NMR (CDCl$_3$, 500 MHz), δ8.5 (s, 1H), 7.4 (m, 2H), 7.3 (t, 1H), 7.1 (d, 1H), 5.7 (d, 1H), 3.0 (br, 1H), 2.8 (b, 1H), 2.6 (br, 1H), 2.4 (br, 1H), 2.3 (s, 3H), 1.7 (br, 2H), 1.5 (br, 1H), 1.3 (br, 1H), 1.1 (m, 1H)

EXAMPLE 63

(3S)-3-[(S)-(3-methoxyphenyl)(2H-tetrazol-2-yl)methyl]piperidine

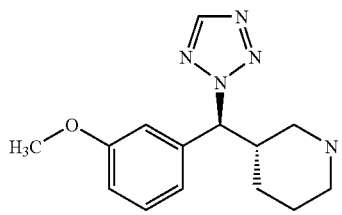 [SMILES: COc1cccc([C@H]([C@H]2CCCNC2)n2ncnn2)c1]

The procedure given in Example 2 was followed using 1-bromo-3-methoxybenzene as a reactant, instead of 2-bromonaphthalene to give (3)-3-[(S)-(3-methoxyphenyl)(2H-tetrazol-2-yl)methyl]piperidine.

1H-NMR (CDCl$_3$, 500 MHz), δ8.5 (s, 1H), 7.3 (t, 1H), 7.1 (d, 2H), 6.9 (d, 1H), 5.7 (d, 1H) 3H), 3.0 (br, 1H), 2.6 (br, 1H), 2.6 (br, 2H), 2.4 (br, 1H), 1.6 (br, 3H), 1.4 (br, 1H), 1.1 (m, 1H)

EXAMPLE 64

(3S)-3-[(R)-(3-methoxyphenyl)(2H-tetrazol-2-yl)methyl]piperidine

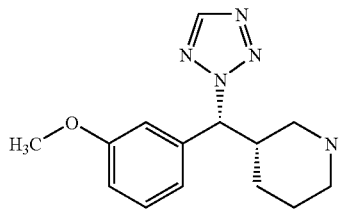 [SMILES: COc1cccc([C@@H]([C@H]2CCCNC2)n2ncnn2)c1]

The procedure given in Example 4 was followed using 1-bromo-3-methoxybenzene as a reactant, instead of 2-bromonaphthalene to give (3S)-3-[(R)-(3-methoxyphenyl)(2H-tetrazol-2-yl)methyl]piperidine.

1H-NMR (CDCl$_3$, 500 MHz), δ8.5 (s, 1H), 7.3 (t, 1H), 7.1 (d, 2H), 6.9 (d, 1H), 5.7 (d, 1H), 3.8 (br, 1H), 3H), 3.0 (br, 1H), 2.8 (br, 2H), 2.6 (br, 1H), 2.4 (br, 1H), 1.7 (br, 2H), 1.4 (br, 1H), 1.3 (br, 1H), 1.1 (m, 1H)

EXAMPLE 65

(3S)-3-[(S)-1-benzothiophen-5-yl(2H-tetrazol-2-yl)methyl]piperidine

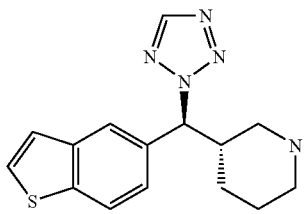 [SMILES: c1nnn([C@H](c2ccc3sccc3c2)[C@H]2CCCNC2)n1]

The procedure given in Example 2 was followed using 5-bromo-1-benzothiophene as a reactant, instead of 2-bromonaphthalene to give (3S)-3-[(S)-1-benzothiophen-5-yl(2H-tetrazol-2-yl)methyl]piperidine.

1H-NMR (CDCl$_3$, 200 MHz), δ8.5 (s, 1H), 8.0 (s, 1H), 7.9 (d, 1H), 7.5 (dd, 2H), 7.3 (d, 1H), 5.9 (d, 1H), 2.9 (br, 2H), 2.6 (br, 2H), 2.4 (br, 2H), 1.6 (br, 2H), 1.4 (br, 1H), 1.2 (br, 1H)

EXAMPLE 66

(3S)-3-[(R)-1-benzothiophen-5-yl(2H-tetrazol-2-yl)methyl]piperidine

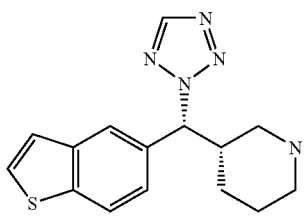 [SMILES: c1nnn([C@@H](c2ccc3sccc3c2)[C@H]2CCCNC2)n1]

The procedure given in Example 4 was followed using 5-bromo-1-benzothiophene as a reactant, instead of 2-bromonaphthalene to give (3S)-3-[(R)-1-benzothiophen-5-yl(2H-tetrazol-2-yl)methyl]piperidine.

1H-NMR (CDCl$_3$, 200 MHz), δ8.5 (s, 1H), 8.0 (s, 1H), 7.9 (d, 1H), 7.5 (dd, 2H), 7.3 (d, 1H), 5.9 (d, 1H), 2.9 (br, 3H), 2.6 (br, 1H), 2.4 (br, 1H), 2.0 (br, 1H), 1.7 (br, 1H), 1.4 (br, 2H), 1.2 (br, 1H)

EXAMPLE 67

(3R)-3-[(R)-(6-chloronaphthalen-2-yl)(2H-tetrazol-2-yl)methyl]piperidine

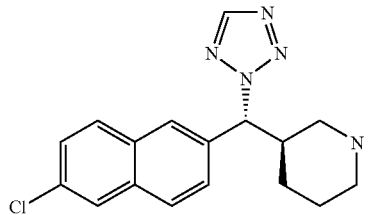 [SMILES: Clc1ccc2cc([C@@H]([C@@H]3CCCNC3)n3ncnn3)ccc2c1]

The procedure given in Example 1 was followed using 2-bromo-6-chloronaphthalene as a reactant, instead of 2-bromonaphthalene to give (3R)-3-[(R)-(6-chloronaphthalen-2-yl)(2H-tetrazol-2-yl)methyl]piperidine.

1H-NMR (CDCl$_3$, 500 MHz), δ8.5 (s, 1H), 8.0 (s, 1H), 7.8 (m, 4H), 7.5 (d, 1H), 6.0 (d, 1H), 3.0 (dd, 2H), 2.6 (m, 2H), 2.4 (t, 1H), 1.8 (br, 1H), 1.7 (br, 1H), 1.6 (br, 1H), 1.4 (m, 1H), 1.2 (m, 1H)

EXAMPLE 68

(3S)-3-[(S)-(6-chloronaphthalen-2-yl)(2H-tetrazol-2-yl)methyl]piperidine

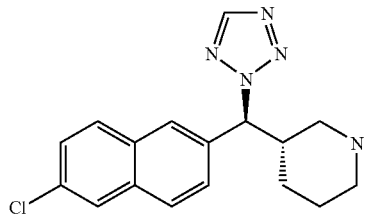 [SMILES: Clc1ccc2cc([C@H]([C@H]3CCCNC3)n3ncnn3)ccc2c1]

The procedure given in Example 2 was followed using 2-bromo-6-chloronaphthalene as a reactant, instead of 2-bromonaphthalene to give (3)-3-[(S)-(6-chloronaphthalen-2-yl)(2H-tetrazol-2-yl)methyl]piperidine.

1H-NMR (CDCl$_3$, 500 MHz), δ8.5 (s, 1H), 8.0 (s, 1H), 7.8 (m, 4H), 7.5 (d, 1H), 6.0 (d, 1H), 3.0 (dd, 2H), 2.6 (m, 2H), 2.4 (t, 1H), 1.8 (br, 1H), 1.7 (br, 1H), 1.6 (br, 1H), 1.4 (m, 1H), 1.2 (m, 1H)

EXAMPLE 69

(3R)-3-[(S)-(6-chloronaphthalen-2-yl)(2H-tetrazol-2-yl)methyl]piperidine

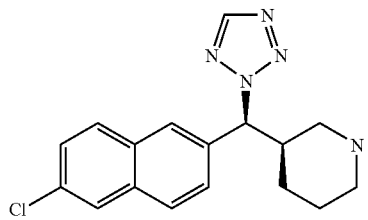 [SMILES: Clc1ccc2cc([C@H]([C@@H]3CCCNC3)n3ncnn3)ccc2c1]

The procedure given in Example 3 was followed using 2-bromo-6-chloronaphthalene as a reactant, instead of 2-bromonaphthalene to give (3R)-3-[(S)-(6-chloronaphthalen-2-yl)(2H-tetrazol-2-yl)methyl]piperidine.

1H-NMR (CDCl$_3$, 500 MHz), δ8.5 (s, 1H), 8.0 (s, 1H), 7.8 (m, 4H), 7.5 (d, 1H), 6.0 (d, 1H), 3.0 (dd, 2H), 2.8 (d, 1H), 2.7 (t, 1H), 2.4 (t, 1H), 1.7 (br, 2H), 1.5 (m, 1H), 1.4 (br, 1H), 1.2 (m, 1H)

EXAMPLE 70

(3S)-3-[(R)-(6-chloronaphthalen-2-yl)(2H-tetrazol-2-yl)methyl]piperidine

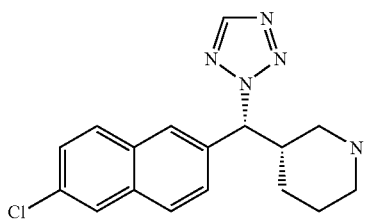 [SMILES: Clc1ccc2cc([C@@H]([C@H]3CCCNC3)n3ncnn3)ccc2c1]

The procedure given in Example 4 was followed using 2-bromo-6-chloronaphthalene as a reactant, instead of 2-bromonaphthalene to give (3S)-3-[(R)-(6-chloronaphthalen-2-yl)(2H-tetrazol-2-yl)methyl]piperidine.

1H-NMR (CDCl$_3$, 500 MHz), δ8.5 (s, 1H), 8.0 (s, 1H), 7.8 (m, 4H), 7.5 (d, 1H), 6.0 (d, 1H), 3.0 (dd, 2H), 2.8 (d, 1H), 2.7 (t, 1H), 2.4 (t, 1H), 1.7 (br, 2H), 1.5 (m, 1H), 1.4 (br, 1H), 1.2 (m, 1H)

EXAMPLE 71

(3S)-3-[(S)-(6-fluoronaphthalen-2-yl)(2H-tetrazol-2-yl)methyl]piperidine

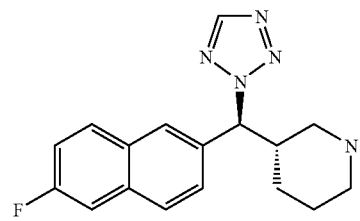 [SMILES: Fc1ccc2cc([C@H]([C@H]3CCCNC3)n3ncnn3)ccc2c1]

The procedure given in Example 2 was followed using 2-bromo-6-fluoronaphthalene as a reactant, instead of 2-bromonaphthalene to give (3S)-3-[(S)-(6-fluoronaphthalen-2-yl)(2H-tetrazol-2-yl)methyl]piperidine.

1H-NMR (CDCl$_3$, 200 MHz), δ8.5 (s, 1H), 8.0 (s, 1H), 7.8 (m, 3H), 7.4 (m, 2H), 6.0 (d, 1H), 3.0 (br, 2H), 2.7 (br, 2H), 2.5 (m, 1H), 1.6 (br, 3H), 1.2 (m, 2H)

EXAMPLE 72

(3S)-3-[(R)-(6-fluoronaphthalen-2-yl)(2H-tetrazol-2-yl)methyl]piperidine

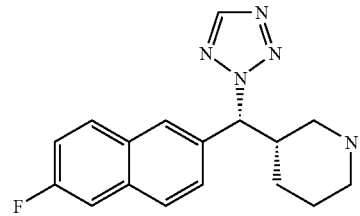 [SMILES: Fc1ccc2cc([C@@H]([C@H]3CCCNC3)n3ncnn3)ccc2c1]

The procedure given in Example 4 was followed using 2-bromo-6-fluoronaphthalene as a reactant, instead of 2-bromonaphthalene to give (3S)-3-[(R)-(6-fluoronaphthalen-2-yl)(2H-tetrazol-2-yl)methyl]piperidine.

1H-NMR (CDCl$_3$, 200 MHz), δ8.5 (s, 1H), 8.0 (s, 1H), 7.8 (m, 3H), 7.4 (m, 2H), 6.0 (d, 1H), 3.0 (br, 2H), 2.6 (br, 2H), 2.2 (br, 1H), 1.8 (br, 1H), 1.4 (br, 2H), 1.2 (br, 2H)

EXAMPLE 73

(3S)-1-ethyl-3-[(S)-naphthalen-2-yl(2H-tetrazol-2-yl)methyl]piperidine

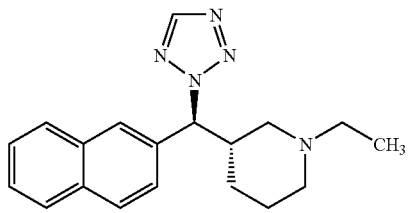 [SMILES: CCN1CCC[C@H]([C@@H](c2ccc3ccccc3c2)n2ncnn2)C1]

(3S)-3-[(S)-naphthalen-2-yl(2H-tetrazol-2-yl)methyl]piperidine (2.0 mmol) from Example 2 was dissolved in acetonitrile and the solution was treated with triethylamine (3.0 mmol) at room temperature. To this solution was added iodoethane in acetonitrile slowly and the solution was warmed up to 40° C. After the completion of the reaction, the reaction mixture was diluted with ethyl acetate, washed with 5% aq NaOH, water, brine, and dried over MgSO$_4$. After concentration, the crude product was purified by flash column chromatography with a 10% Methanol in dichloromethane to afford (3S)-1-ethyl-3-[(S)-naphthalen-2-yl(2H-tetrazol-2-yl)methyl]piperidine.

1H-NMR (CDCl$_3$, 200 MHz), δ8.6 (s, 1H), 8.0 (d, 1H), 7.9 (m, 3H), 7.7 (d, 1H), 7.5 (m, 2H), 6.1 (d, 1H), 3.2 (br, 1H), 2.8 (br, 1H), 2.4 (m, 3H), 2.2 (br, 1H), 2.0 (m, 1H), 1.7 (br, 3H), 1.4 (br, 1H), 1.0 (m, 4H)

EXAMPLE 74

(3R)-3-[(R)-naphthalen-2-yl-(5-phenyl-tetrazol-2-yl)methyl]piperidine

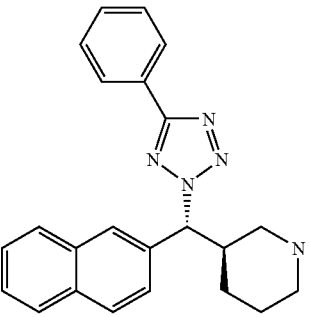

The procedure given in Example 1 was followed using 5-phenyl-1H-tetrazole as a reactant, instead of 1H-tetrazole to give (3R)-3-[(R)-naphthalen-2-yl-(5-phenyl-tetrazol-2-yl)methyl]piperidine.

1H-NMR (CDCl$_3$, 500 MHz), δ8.2 (d, 2H), 8.0 (s, 1H), 7.8 (m, 4H), 7.5 (m, 5H), 6.0 (d, 1H), 3.0 (br, 2H), 2.8 (br, 1H), 2.6 (br, 2H), 1.6 (br, 3H), 1.3 (br, 2H)

EXAMPLE 75

(3S)-3-[(S)-naphthalen-2-yl-(5-phenyl-tetrazol-2-yl)methyl]piperidine

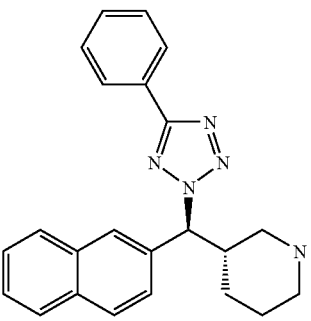

The procedure given in Example 2 was followed using 5-phenyl-1H-tetrazole as a reactant, instead of 1H-tetrazole to give (3S)-3-[(S)-naphthalen-2-yl-(5-phenyl-tetrazol-2-yl)methyl]piperidine.

1H-NMR (CDCl$_3$, 500 MHz), δ8.2 (d, 2H), 8.0 (s, 1H), 7.8 (m, 4H), 7.5 (m, 5H), 6.0 (d, 1H), 3.0 (br, 2H), 2.8 (br, 1H), 2.6 (br, 2H), 1.6 (br, 3H), 1.3 (br, 2H)

EXAMPLE 76

(3R)-3-[(S)-naphthalen-2-yl-(5-phenyl-tetrazol-2-yl)methyl]piperidine

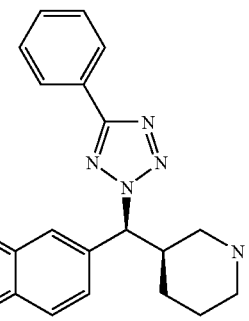

The procedure given in Example 3 was followed using 5-phenyl-1H-tetrazole as a reactant, instead of 1H-tetrazole to give (3R)-3-[(S)-naphthalen-2-yl-(5-phenyl-tetrazol-2-yl)methyl]piperidine.

1H-NMR (CDCl$_3$, 500 MHz), δ8.2 (d, 2H), 8.0 (s, 1H), 7.8 (m, 4H), 7.5 (m, 5H), 5.9 (d, 1H), 3.0 (br, 2H), 2.8 (br 1H), 2.6 (br, 2H), 1.8 (br 1H), 1.7 (br, 2H), 1.2 (br, 2H)

EXAMPLE 77

(3S)-3-[(R)-naphthalen-2-yl-(5-phenyl-tetrazol-2-yl)methyl]piperidine

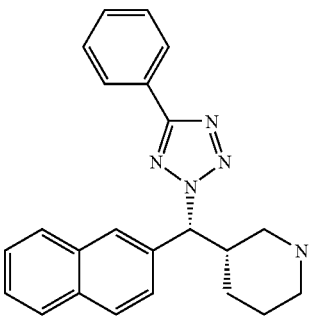 [SMILES: c1ccc(-c2nnn([C@@H](c3ccc4ccccc4c3)[C@H]3CCCNC3)n2)cc1]

The procedure given in Example 4 was followed using 5-phenyl-1H-tetrazole as a reactant, instead of 1H-tetrazole to give (3S)-3-[(R)-naphthalen-2-yl-(5-phenyl-tetrazol-2-yl)methyl]piperidine.

1H-NMR (CDCl$_3$, 500 MHz), δ8.2 (d, 2H), 8.0 (s, 1H), 7.8 (m, 4H), 7.5 (m, 5H), 5.9 (d, 1H), 3.0 (br, 2H), 2.8 (br, 1H), 2.6 (br, 2H), 1.8 (br, 1H), 1.7 (br, 2H), 1.2 (br, 2H)

EXAMPLE 78

1-{(S)-naphthalen-2-yl[(3S)-piperidin-3-yl]methyl}-1H-benzotriazole

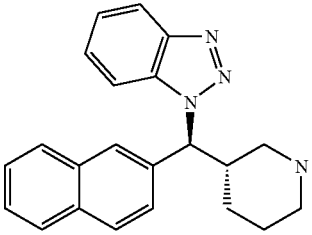 [SMILES: c1ccc2cc([C@H]([C@H]3CCCNC3)n3nnc4ccccc43)ccc2c1]

The procedure given in Example 2 was followed using benzotriazole as a reactant instead of 1H-tetrazole to give 1-{(S)-naphthalen-2-yl[(3S)-piperidin-3-yl]methyl}-1H-benzotriazole.

1H-NMR (CDCl$_3$, 500 MHz), δ8.0 (d, 1H), 7.9 (s, 1H), 7.8 (m, 3H), 7.6 (m, 2H), 7.5 (m, 2H), 7.4 (t, 1H), 7.3 (t, 1H), 5.9 (d, 1H), 3.4 (br, 1H), 3.1 (br, 2H), 2.8 (br, 2H), 1.8 (br, 3H), 1.6 (br, 1H), 1.4 (br, 1H)

EXAMPLE 79

1-{(R)-naphthalen-2-yl[(3S)-piperidin-3-yl]methyl}-1H-benzotriazole

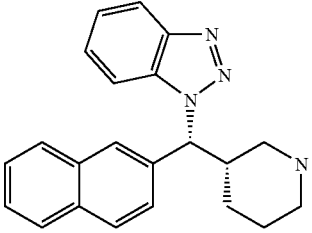 [SMILES: c1ccc2cc([C@@H]([C@H]3CCCNC3)n3nnc4ccccc43)ccc2c1]

The procedure given in Example 4 was followed using benzotriazole as a reactant, instead of 1H-tetrazole to give 1-{(R)-naphthalen-2-yl[(3S)-piperidin-3-yl]methyl}-1H-benzotriazole.

1H-NMR (CDCl$_3$, 500 MHz), δ8.0 (m, 2H), 7.8 (m, 3H), 7.7 (d, 1H), 7.6 (d, 1H), 7.5 (m, 3H), 7.4 (m, 1H), 5.8 (d, 1H), 3.4 (br, 1H), 3.0 (br, 2H), 2.8 (br, 1H), 2.6 (br, 1H), 1.6 (br, 3H), 1.3 (br, 2H)

EXAMPLE 80

2-{(S)-naphthalen-2-yl[(3S)-piperidin-3-yl]methyl}-2H-benzotriazole

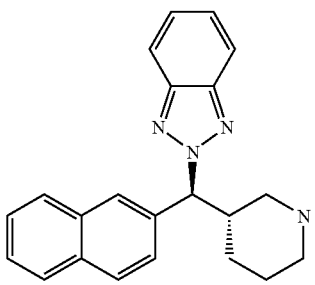 [SMILES: c1ccc2cc([C@H]([C@H]3CCCNC3)n3nc4ccccc4n3)ccc2c1]

The procedure given in Example 2 was followed using benzotriazole as a reactant, instead of 1H-tetrazole to give 2-{(S)-naphthalen-2-yl[(3S)-piperidin-3-yl]methyl}-2H-benzotriazole.

1H-NMR (CDCl$_3$, 500 MHz), δ8.0 (s, 1H), 7.8 (m, 7H), 7.5 (m, 2H), 7.4 (m, 2H), 5.9 (d, 1H), 3.2 (br, 1H), 3.1 (br, 1H), 2.8 (br, 1H), 2.6 (br, 2H), 1.7 (br, 2H), 1.6 (br, 1H), 1.2 (br, 1H)

EXAMPLE 81

2-{(R)-naphthalen-2-yl[(3S)-piperidin-3-yl]methyl}-2H-benzotriazole

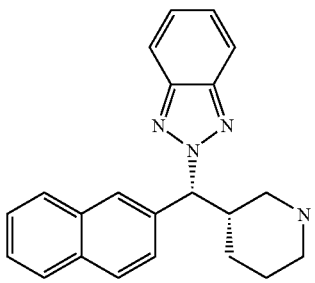 [SMILES: c1ccc2cc([C@@H]([C@H]3CCCNC3)n3nc4ccccc4n3)ccc2c1]

The procedure given in Example 4 was followed using benzotriazole as a reactant, instead of 1H-tetrazole to give 2-{(R)-naphthalen-2-yl[(3S)-piperidin-3-yl]methyl}-2H-benzotriazole.

1H-NMR (CDCl$_3$, 500 MHz), δ8.1 (s, 1H), 7.8 (m, 7H), 7.5 (m, 2H), 7.4 (m, 2H), 5.9 (d, 1H), 3.2 (br, 1H), 3.0 (br, 2H), 2.7 (br, 1H), 2.5 (br, 1H), 1.8 (br, 1H), 1.6 (br, 1H), 1.5 (br, 1H), 1.3 (br, 1H)

EXAMPLE 82

(3S)-3-[(R)-1-benzothiophen-3-yl(2H-tetrazol-2-yl)methyl]piperidine

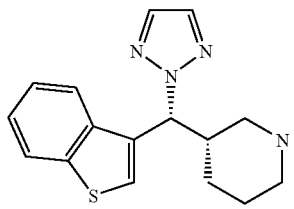 [SMILES: c1ccc2c([C@@H]([C@H]3CCCNC3)n3nccn3)csc2c1]

The procedure given in Example 4 was followed using 3-bromo-1-benzothiophene as a reactant, instead of 2-bromonaphthalene to give (3S)-3-[(R)-1-benzothiophen-3-yl(2H-tetrazol-2-yl)methyl]piperidine.

1H-NMR (CDCl$_3$, 500 MHz), δ8.5 (s, 1H), 7.9 (br, 2H), 7.4 (br, 2H), 7.3 (br, 1H), 6.4 (br, 1H), 3.7 (br, 1H), 3.5 (br, 2H), 3.2 (br, 2H), 2.0 (br, 3H), 1.6 (br, 1H), 1.2 (br, 1H)

EXAMPLE 83

(3R)-3-[(R)-(6-fluoronaphthalen-2-yl)(2H-tetrazol-2-yl)methyl]piperidine

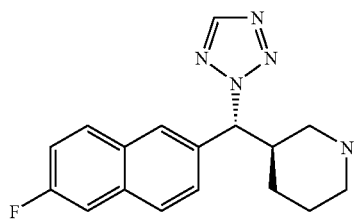 [SMILES: Fc1ccc2cc([C@@H]([C@@H]3CCCNC3)n3ncnn3)ccc2c1]

The procedure given in Example 1 was followed using 2-bromo-6-fluoronaphthalene as a reactant, instead of 2-bromonaphthalene to give (3R)-3-[(R)-(6-fluoronaphthalen-2-yl)(2H-tetrazol-2-yl)methyl]piperidine.

1H-NMR (CDCl$_3$, 500 MHz), δ8.5 (s, 1H), 8.0 (s, 1H), 7.8 (m, 3H), 7.4 (d, 1H), 7.3 (m, 1H), 6.0 (d, 1H), 3.0 (br, 2H), 2.7 (br, 2H), 2.5 (m, 1H), 1.8 (br, 2H), 1.6 (br, 1H), 1.4 (br, 1H), 1.2 (br, 1H)

EXAMPLE 84

(3R)-3-[(S)-(6-fluoronaphthalen-2-yl)(2H-tetrazol-2-yl)methyl]piperidine

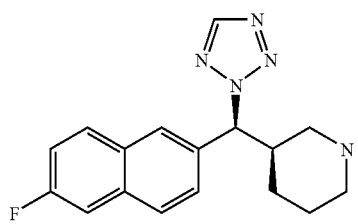 [SMILES: Fc1ccc2cc([C@H]([C@@H]3CCCNC3)n3ncnn3)ccc2c1]

The procedure given in Example 3 was followed using 2-bromo-6-fluoronaphthalene as a reactant, instead of 2-bromonaphthalene to give (3R)-3-[(S)-(6-fluoronaphthalen-2-yl)(2H-tetrazol-2-yl)methyl]piperidine 1H-NMR (CDCl$_3$, 500 MHz), δ8.5 (s, 1H), 8.0 (s, 1H), 7.8 (m, 3H), 7.4 (d, 1H), 7.3 (m, 1H), 6.0 (d, 1H), 3.0 (br, 2H), 2.8 (br, 1H), 2.6 (br, 1H), 2.4 (br, 1H), 1.8 (br, 2H), 1.5 (br, 1H), 1.4 (br, 1H), 1.2 (br, 1H)

EXAMPLE 85

(3S)-3-[(S)-(6-methylnaphthalen-2-yl)(2H-tetrazol-2-yl)methyl]piperidine

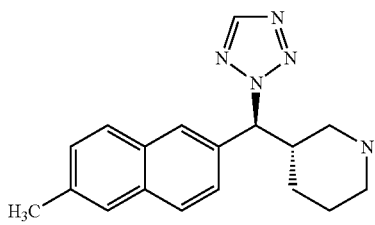 [SMILES: Cc1ccc2cc([C@H]([C@H]3CCCNC3)n3ncnn3)ccc2c1]

The procedure given in Example 2 was followed using 2-bromo-6-methylnaphthalene as a reactant, instead of 2-bromonaphthalene to give (3S)-3-[(S)-(6-methylnaphthalen-2-yl)(2H-tetrazol-2-yl)methyl]piperidine.

1H-NMR (CDCl$_3$, 500 MHz), δ8.5 (s, 1H), 8.0 (s, 1H), 7.8 (t, 2H), 7.7 (d, 1H), 7.6 (s, 1H), 7.4 (d, 1H), 6.0 (d, 1H), 3.0 (br, 2H), 2.7 (br, 2H), 2.5 (s, 3H), 2.4 (br, 1H), 1.7 (br, 1H), 1.6 (br, 1H), 1.4 (br, 1H), 1.2 (br, 1H)

EXAMPLE 86

(3S)-3-[(R)-(6-methylnaphthalen-2-yl)(2H-tetrazol-2-yl)methyl]piperidine

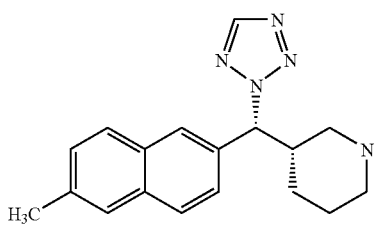 [SMILES: Cc1ccc2cc([C@@H]([C@H]3CCCNC3)n3ncnn3)ccc2c1]

The procedure given in Example 4 was followed using 2-bromo-6-methylnaphthalene as a reactant, instead of 2-bromonaphthalene to give (3S)-3-[(R)-(6-methylnaphthalen-2-yl)(2H-tetrazol-2-yl)methyl]piperidine.

1H-NMR (CDCl$_3$, 500 MHz), δ8.5 (s, 1H), 8.0 (s, 1H), 7.8 (t, 2H), 7.7 (d, 1H), 7.6 (s, 1H), 7.4 (d, 1H), 5.9 (d, 1H), 3.0 (br,

2H), 2.8 (br, 1H), 2.6 (br, 1H), 2.5 (s, 3H), 2.4 (br, 1H), 1.7 (br, 1H), 1.5 (br, 1H), 1.4 (br, 1H), 1.2 (br, 1H)

EXAMPLE 87

(3S)-3-[(S)-(4-fluoronaphthalen-1-yl)(2H-tetrazol-2-yl)methyl]piperidine

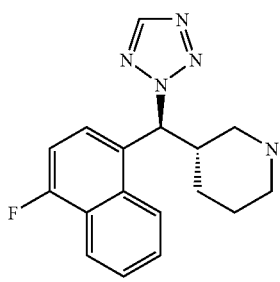 [SMILES: Fc1ccc([C@H]([C@H]2CCCNC2)n2ncnn2)c2ccccc12]

The procedure given in Example 2 was followed using 1-bromo-4-fluoronaphthalene as a reactant, instead of 2-bromonaphthalene to give (3S)-3-[(S)-(4-fluoronaphthalen-1-yl)(2H-tetrazol-2-yl)methyl]piperidine.

1H-NMR (CDCl$_3$, 500 MHz), δ8.5 (s, 1H) 8.4 (d, 1H), 8.2 (d, 1H), 8.0 (m, 1H), 7.7 (t, 1H), 7.6 (t, 1), 7.2 (t, 1H), 6.7 (d, 1H), 3.1 (br, 2H), 2.9 (br, 1H), 2.7 (br, 2H), 2.5 (br, 1H), 1.6 (br, 2H), 1.5 (br, 1H), 1.2 (br, 1H)

EXAMPLE 88

(3S)-3-[(R)-(4-fluoronaphthalen-1-yl)(2H-tetrazol-2-yl)methyl]piperidine

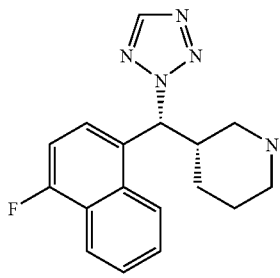 [SMILES: Fc1ccc([C@@H]([C@H]2CCCNC2)n2ncnn2)c2ccccc12]

The procedure given in Example 4 was followed using 1-bromo-4-fluoronaphthalene as a reactant, instead of 2-bromonaphthalene to give (3S)-3-[(R)-(4-fluoronaphthalen-1-yl)(2H-tetrazol-2-yl)methyl]piperidine.

1H-NMR (CDCl$_3$, 500 MHz), δ8.5 (s, 1H), 8.4 (d, 1H), 8.2 (d, 1H), 7.9 (m, 1H), 7.7 (t, 1H), 7.6 (t, 1H), 7.2 (t, 1H), 6.7 (d, 1H), 3.0 (br, 2H), 2.9 (br, 1H), 2.7 (br, 1H), 2.4 (br, 1H), 1.8 (br, 2H), 1.5 (br, 1H), 1.4 (br, 1H), 1.3 (br, 1H)

EXAMPLE 89

(3S)-3-[(R)-naphthalen-2-yl(4H-1,2,4-triazol-4-yl)methyl]piperidine

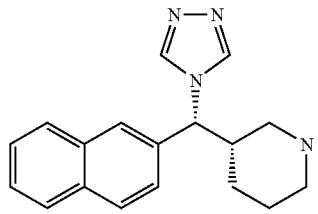 [SMILES: c1ccc2cc([C@@H]([C@H]3CCCNC3)n3cnnc3)ccc2c1]

The procedure given in Example 4 was followed using 1,2,4-triazole as a reactant, instead of 1H-tetrazole to give (3S)-3-[(R)-naphthalen-2-yl(4H-1,2,4-triazol-4-yl)methyl]piperidine.

1H-NMR (CDCl$_3$, 500 MHz), δ8.2 (s, 1H), 8.0 (s, 1H), 7.9 (s, 1H), 7.8 (m, 4), 7.7 (d, 1H), 7.5 (m, 2H), 5.3 (d, 1H), 3.0 (br, 3H), 2.7 (br, 1H), 2.5 (br, 1H), 1.8 (br, 1H), 1.6 (br, 2H), 1.3 (br, 2H)

EXAMPLE 90

(3S)-3-[(S)-naphthalen-2-yl(1H-1,2,4-triazol-1-yl)methyl]piperidine

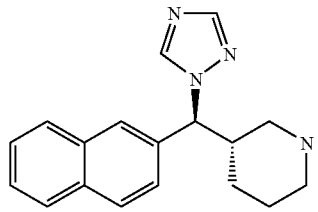 [SMILES: c1ccc2cc([C@H]([C@H]3CCCNC3)n3cncn3)ccc2c1]

The procedure given in Example 2 was followed using 1,2,4-triazole as a reactant instead of 1H-tetrazole to give (3S)-3-[(S)-naphthalen-2-yl(1H-1,2,4-triazol-1-yl)methyl]piperidine.

1H-NMR (CDCl$_3$, 500 MHz), δ8.3 (s, 1H), 8.0 (s, 1H), 7.8 (m, 4H), 7.7 (d, 1), 7.5 (m, 2H), 5.4 (d, 1H), 3.0 (br, 1H), 2.8 (br, 2H), 2.4 (br, 2H), 1.6 (br, 4H), 1.2 (br, 1H)

EXAMPLE 91

(3S)-3-[(R)-naphthalen-2-yl(1H-1,2,4-triazol-1-yl)methyl]piperidine

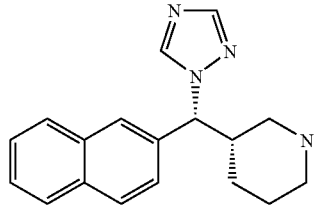

The procedure given in Example 4 was followed using 1,2,4-triazole as a reactant, instead of 1H-tetrazole to give (3S)-3-[(R)-naphthalen-2-yl(1H-1,2,4-triazol-1-yl)methyl]piperidine.

1H-NMR (CDCl$_3$, 500 MHz), δ8.3 (s, 1H), 8.0 (s, 1H), 7.8 (m, 4H), 7.7 (d, 1H), 7.5 (m, 2H), 5.4 (d, 1H), 3.0 (br, 1H), 2.8 (br, 2H), 2.7 (br, 1H), 2.5 (br, 1H), 1.7 (br, 1H), 1.6 (br, 1H), 1.5 (br, 1H), 1.2 (br, 1H)

EXAMPLE 92

(3S)-3-[(R)-naphthalen-2-yl(1H-pyrazol-1-yl)methyl]piperidine

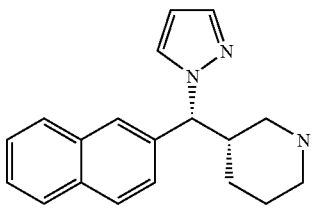

The procedure given in Example 4 was followed using pyrazole as a reactant, instead of 1H-tetrazole to give (3S)-3-[(R)-naphthalen-2-yl(1H-pyrazol-1-yl)methyl]piperidine.

1H-NMR (CDCl$_3$, 500 MHz), δ8.0 (s, 1H), 7.8 (m, 3H), 7.5 (m, 5H), 6.2 (s, 1H), 5.2 (d, 1H), 3.2 (br, 1H), 3.1 (br, 2H), 2.7 (br, 1H), 2.5 (br, 1H), 1.8 (br, 2H), 1.6 (br, 1H), 1.3 (br, 2H)

EXAMPLE 93

(3S)-3-[(S)-1-benzothiophen-2-yl(2H-tetrazol-2-yl)methyl]piperidine

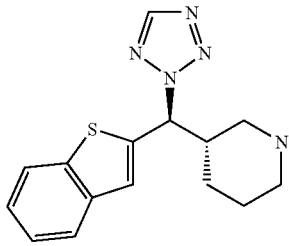 [SMILES: c1ccc2sc([C@H]([C@H]3CCCNC3)n3ncnn3)cc2c1]

The procedure given in Example 2 was followed using 2-bromo-1-benzothiophene as a reactant, instead of 2-bromonaphthalene to give (3S)-3-[(S)-1-benzothiophen-2-yl (2H-tetrazol-2-yl)methyl]piperidine.

1H-NMR (CDCl$_3$, 500 MHz), δ8.6 (s, 1H), 7.8 (m, 2H), 7.5 (s, 1H), 7.4 (br, 2H), 6.3 (d, 1H), 3.0 (br, 1H), 2.8 (br, 2H), 2.6 (br, 1H), 2.4 (br, 1H), 1.8 (br, 3H), 1.5 (br, 1.3 (br, 1H)

EXAMPLE 94

(3S)-3-[(R)-1-benzothiophen-2-yl(2H-tetrazol-2-yl)methyl]piperidine

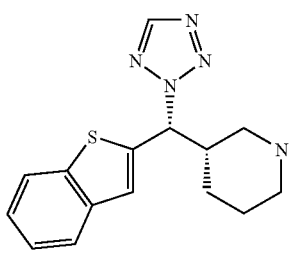 [SMILES: c1ccc2sc([C@@H]([C@H]3CCCNC3)n3ncnn3)cc2c1]

The procedure given in Example 4 was followed using 2-bromo-1-benzothiophene as a reactant, instead of 2-bromonaphthalene to give (3S)-3-[(R)-1-benzothiophen-2-yl (2H-tetrazol-2-yl)methyl]piperidine.

1H-NMR (CDCl$_3$, 500 MHz), δ6.6 (s, 1H), 7.8 (m, 2H), 7.5 (s, 1H), 7.4 (br, 2H), 6.3 (d, 1H), 3.0 (br, 2H), 2.8 (br, 1H), 2.7 (br, 1H), 2.6 (br, 1H), 1.8 (br, 2H), 1.5 (br, 1H), 1.3 (br, 1H), 1.1 (br, 1H)

EXAMPLE 95

(3S)-3-[(S)-(3,4-difluorophenyl)(2H-tetrazol-2-yl) methyl]piperidine

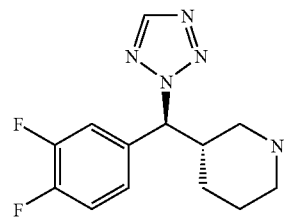 [SMILES: Fc1ccc([C@H]([C@H]2CCCNC2)n2ncnn2)cc1F]

The procedure given in Example 2 was followed using 4-bromo-1,2-difluorobenzene as a reactant, instead of 2-bromonaphthalene to give (3S)-3-[(S)-(3,4-difluorophenyl)(2H-tetrazol-2-yl)methyl]piperidine.

1H-NMR (CDCl$_3$, 500 MHz), δ8.5 (s, 1H), 7.5 (m, 1H), 7.3 (m, 1H), 7.2 (m, 1H), 5.8 (d, 1H), 2.8 (br, 5H), 1.8 (br, 1H), 1.6 (br, 1H), 1.5 (br, 1H), 1.2 (br, 1H)

EXAMPLE 96

(3S)-3-[(R)-(3,4-difluorophenyl)(2H-tetrazol-2-yl) methyl]piperidine

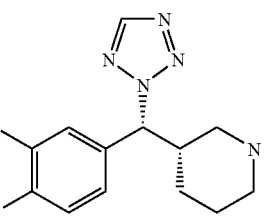

The procedure given in Example 4 was followed using 4-bromo-1,2-difluorobenzene as a reactant, instead of 2-bromonaphthalene to give (3S)-3-[(R)-(3,4-difluorophenyl)(2H-tetrazol-2-yl)methyl]piperidine.

1N-NMR(CDCl₃, 500 MHz), δ8.5 (s, 1H), 7.5 (m, 1H), 7.3 (m, 1H), 7.2 (m, 1H), 5.8 (d, 1H), 2.8 (br, 5H), 1.8 (br, 2H), 1.4 (br, 2H), 1.1 (br, 1H)

EXAMPLE 97

(3S)-3-[(S)-(2,3-dichlorophenyl)(2H-tetrazol-2-yl)methyl]piperidine

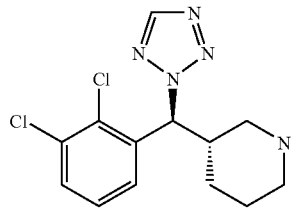 [SMILES: Clc1cccc([C@H]([C@H]2CCCNC2)n2ncnn2)c1Cl]

The procedure given in Example 2 was followed using 1-bromo-2,3-dichlorobenzene as a reactant, instead of 2-bromonaphthalene to give (3S)-3-[(S)-(2,3-dichlorophenyl)(2H-tetrazol-2-yl)methyl]piperidine.

1H-NMR (CDCl₃, 500 MHz), δ8.5 (s, 1H), 7.8 (d, 1H), 7.5 (d, 1H), 7.3 (t, 1H), 6.6 (d, 1H), 3.0 (br, 1H), 2.8 (br, 1H), 2.6 (br, 2H), 2.4 (br, 2H), 1.8 (br, 1H), 1.6 (br, 1H), 1.5 (br, 1H), 1.3 (br, 1H)

EXAMPLE 98

(3S)-3-[(R)-(2,3-dichlorophenyl)(2H-tetrazol-2-yl)methyl]piperidine

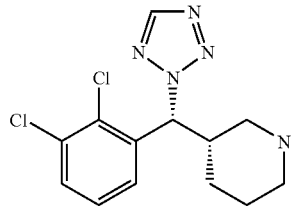 [SMILES: Clc1cccc([C@@H]([C@H]2CCCNC2)n2ncnn2)c1Cl]

The procedure given in Example 4 was followed using 1-bromo-2,3-dichlorobenzene as a reactant, instead of 2-bromonaphthalene to give (3S)-3-[(R)-(2,3-dichlorophenyl)(2H-tetrazol-2-yl)methyl]piperidine.

1H-NMR (CDCl₃, 500 MHz), δ8.5 (s, 1H), 7.8 (d, 1H), 7.5 (d, 1H), 7.3 (t, 1H), 6.5 (d, 1H), 2.8 (br, 5H), 1.8 (br, 1H), 1.5 (br, 1H), 1.4 (br, 1H), 1.3 (br, 1H)

EXAMPLE 99

(3R)-3-[(R)-(1-fluoronaphthalen-2-yl)(2H-tetrazol-2-yl)methyl]piperidine

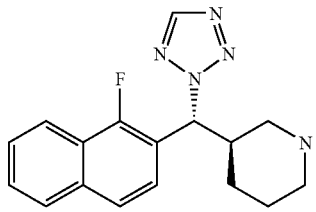 [SMILES: Fc1c([C@@H]([C@@H]2CCCNC2)n2ncnn2)ccc2ccccc12]

The procedure given in Example 1 was followed using 2-bromo-1-fluoronaphthalene as a reactant, instead of 2-bromonaphthalene to give (3R)-3-[(R)-(1-fluoronaphthalen-2-yl)(2H-tetrazol-2-yl)methyl]piperidine.

1H-NMR (CDCl₃, 500 MHz), δ8.5 (s, 1H), 8.2 (m, 1H), 7.8 (m, 2H), 7.7 (d, 1H), 7.6 (m, 2H), 6.5 (d, 1H), 3.0 (br, 1H), 2.9 (br, 1H), 2.6 (br, 2H), 2.5 (br, 1H), 2.3 (br, 1H), 1.7 (br, 1H), 1.6 (br, 1H), 1.5 (br, 1H), 1.3 (br, 1H)

EXAMPLE 100

(3S)-3-[(S)-(1-fluoronaphthalen-2-yl)(2H-tetrazol-2-yl)methyl]piperidine

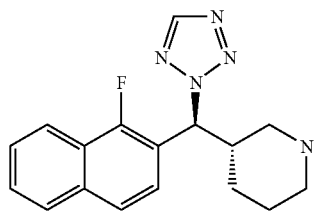 [SMILES: Fc1c([C@H]([C@H]2CCCNC2)n2ncnn2)ccc2ccccc12]

The procedure given in Example 2 was followed using 2-bromo-1-fluoronaphthalene as a reactant, instead of 2-bromonaphthalene to give (3S)-3-[(S)-(1-fluoronaphthalen-2-yl)(2H-tetrazol-2-yl)methyl]piperidine.

1H-NMR (CDCl₃, 500 MHz), δ8.5 (s, 1H), 8.2 (m, 1H), 7.8 (m, 2H), 7.7 (d, 1H), 7.6 (m, 2H), 6.5 (d, 1H), 3.0 (br, 1H), 2.9 (br, 1H), 2.6 (br, 2H), 2.5 (br, 1H), 2.3 (br, 1H), 1.7 (br, 1H), 1.6 (br, 1H), 1.5 (br, 1H), 1.3 (br, 1H)

EXAMPLE 101

(3R)-3-[(S)-(1-fluoronaphthalen-2-yl)(2H-tetrazol-2-yl)methyl]piperidine

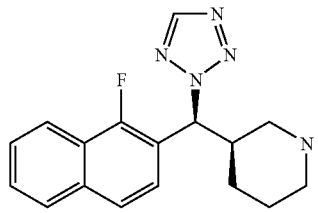 [SMILES: Fc1c([C@H]([C@@H]2CCCNC2)n2ncnn2)ccc2ccccc12]

The procedure given in Example 3 was followed using 2-bromo-1-fluoronaphthalene as a reactant, instead of 2-bromonaphthalene to give (3R)-3-[(S)-(1-fluoronaphthalen-2-yl)(2H-tetrazol-2-yl)methyl]piperidine.

1H-NMR (CDCl₃, 500 MHz), δ8.5 (s, 1H), 8.1 (m, 1H), 7.8 (m, 2H), 7.7 (d, 1H), 7.6 (m, 2H), 6.5 (d, 1H), 3.0 (br, 1H), 2.9 (br, 2H), 2.6 (br, 1H), 2.5 (br, 1H), 1.7 (br, 1H), 1.5 (br, 1H), 1.4 (br, 1H), 1.2 (br, 1H)

EXAMPLE 102

(3S)-3-[(R)-(1-fluoronaphthalen-2-yl)(2H-tetrazol-2-yl)methyl]piperidine

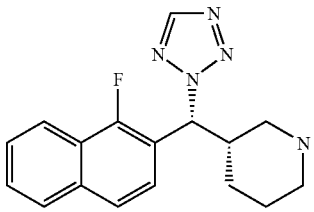 [SMILES: Fc1c([C@@H]([C@H]2CCCNC2)n2ncnn2)ccc2ccccc12]

The procedure given in Example 4 was followed using 2-bromo-1-fluoronaphthalene as a reactant, instead of 2-bromonaphthalene to give (3S)-3-[(R)-(1-fluoronaphthalen-2-yl)(2H-tetrazol-2-yl)methyl]piperidine.

1H-NMR (CDCl$_3$, 500 MHz), δ8.5 (s, 1H), 8.1 (m, 1H), 7.8 (m, 2H), 7.7 (d, 1H), 7.6 (m, 2H), 6.5 (d, 1H), 3.0 (br, 1H), 2.9 (br, 2H), 2.6 (br, 1H), 2.5 (br, 1H), 1.7 (br, 1H), 1.5 (br, 1H), 1.4 (br, 1H), 1.2 (br, 1H)

EXAMPLE 103

(3R)-3-[(R)-(1-fluoronaphthalen-2-yl)(5-methyl-2H-tetrazol-2-yl)methyl]piperidine

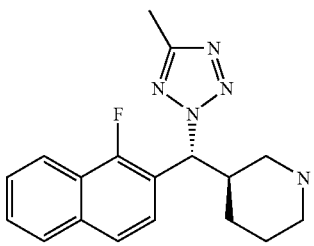 [SMILES: Cc1nnn([C@@H](c2ccc3ccccc3c2F)[C@@H]2CCCNC2)n1]

The procedure given in Example 99 was followed using 5-methyl-1H-tetrazole as a reactant, instead of 1H-tetrazole to give (3R)-3-[(R)-(1-fluoronaphthalen-2-yl)(5-methyl-2H-tetrazol-2-yl)methyl]piperidine.

1H-NMR (CDCl$_3$, 500 MHz), δ8.1 (d, 1H), 7.8 (m, 2H), 7.7 (d, 1H), 7.6 (m, 2H), 6.4 (d, 1H), 3.0 (br, 1H), 2.8 (br, 1H), 2.6 (br, 2H), 2.5 (s, 3H), 2.5 (br, 1H), 2.4 (br, 1H), 1.7 (br, 1H), 1.6 (br, 1H), 1.4 (br, 1H), 1.2 (br, 1H)

EXAMPLE 104

(3S)-3-[(S)-(1-fluoronaphthalen-2-yl)(5-methyl-2H-1-tetrazol-2-yl)methyl]piperidine

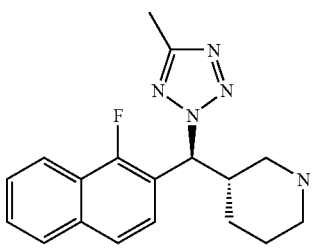 [SMILES: Cc1nnn([C@H](c2ccc3ccccc3c2F)[C@H]2CCCNC2)n1]

The procedure given in Example 100 was followed using 5-methyl-1H-tetrazole as a reactant, instead of 1H-tetrazole to give (3S)-3-[(S)-(1-fluoronaphthalen-2-yl)(5-methyl-2H-tetrazol-2-yl)methyl]piperidine.

1H-NMR (CDCl$_3$, 500 MHz), δ8.1 (d, 1H), 7.8 (m, 2H), 7.7 (d, 1H), 7.6 (m, 2H), 6.4 (d, 1H), 3.0 (br, 1H), 2.8 (br, 1H), 2.6 (br, 2H), 2.5 (s, 3H), 2.5 (br, 1H), 2.4 (br, 1H), 1.7 (br, 1H), 1.6 (br, 1H), 1.4 (br, 1H), 1.2 (br, 1H)

EXAMPLE 105

(3R)-3-[(S)-(1-fluoronaphthalen-2-yl)(5-methyl-2H-tetrazol-2-yl)methyl]piperidine

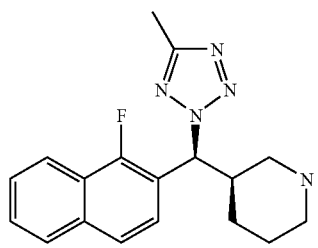 [SMILES: Cc1nnn([C@H](c2ccc3ccccc3c2F)[C@@H]2CCCNC2)n1]

The procedure given in Example 101 was followed using 5-methyl-1H-tetrazole as a reactant, instead of 1H-tetrazole to give (3R)-3-[(S)-(1-fluoronaphthalen-2-yl)(5-methyl-2H-tetrazol-2-yl)methyl]piperidine.

1H-NMR (CDCl$_3$, 500 MHz), δ8.1 (m, 1H), 7.8 (m, 2H), 7.7 (d, 1H), 7.6 (m, 2H), 6.3 (d, 1H), 3.0 (br, 1H), 2.8 (br, 2H), 2.6 (br, 1H), 2.5 (s, 3H), 2.4 (br, 1H), 2.2 (br, 1H), 1.7 (br, 1H), 1.5 (br, 2H), 1.2 (br, 1H)

EXAMPLE 106

(3S)-3-[(R)-(1-fluoronaphthalen-2-yl)(5-methyl-2H-tetrazol-2-yl)methyl]piperidine

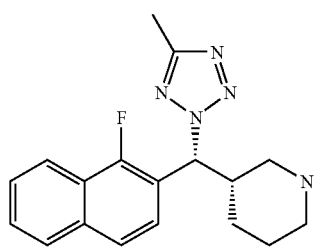 [SMILES: Cc1nnn([C@@H](c2ccc3ccccc3c2F)[C@H]2CCCNC2)n1]

The procedure given in Example 102 was followed using 5-methyl-1H-tetrazole as a reactant, instead of 1H-tetrazole to give (3S)-3-[(R)-(1-fluoronaphthalen-2-yl)(5-methyl-2H-tetrazol-2-yl)methyl]piperidine.

1H-NMR (CDCl$_3$, 500 MHz), δ8.1 (m, 1H), 7.8 (m, 2H), 7.7 (d, 1H), 7.6 (m, 2H), 6.3 (d, 1H), 3.0 (br, 1H), 2.8 (br, 2H), 2.6 (br, 1N), 2.5 (s, 3H), 2.4 (br, 1H), 2.2 (br, 1H), 1.7 (br, 1H), 1.5 (br, 2H), 1.2 (br, 1H)

EXAMPLE 107

(3R)-3-[(R)-(1-fluoronaphthalen-2-yl)(5-phenyl-2H-tetrazol-2-yl)methyl]piperidine

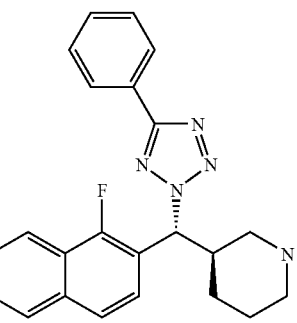

The procedure given in Example 99 was followed using 5-phenyl-1H-tetrazole as a reactant, instead of 1H-tetrazole to give (3R)-3-[(R)-(1-fluoronaphthalen-2-yl)(5-phenyl-2H-tetrazol-2-yl)methyl]piperidine.

1H-NMR (CDCl$_3$, 500 MHz), δ8.2 (m, 3H), 7.8 (m, 2H), 7.7 (d, 1H), 7.6 (m, 2H), 7.5 (m, 3H), 6.5 (d, 1H), 3.0 (br, 2H), 2.7 (br, 3H), 2.2 (br, 1H), 1.7 (br, 2H), 1.5 (br, 1H), 1.3 (br, 1H)

EXAMPLE 108

(3S)-3-[(S)-(1-fluoronaphthalen-2-yl)(5-phenyl-2H-tetrazol-2-yl)methyl]piperidine

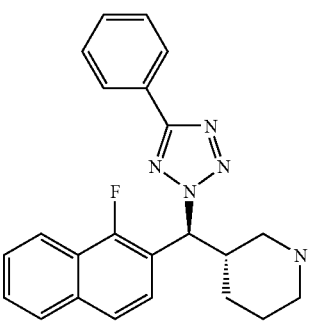 [SMILES: Fc1c([C@H]([C@H]2CCCNC2)n2nnc(-c3ccccc3)n2)ccc2ccccc12]

The procedure given in Example 100 was followed using 5-phenyl-1H-tetrazole as a reactant, instead of 1H-tetrazole to give (3S)-3-[(S)-(1-fluoronaphthalen-2-yl)(5-phenyl-2H-tetrazol-2-yl)methyl]piperidine.

1H-NMR (CDCl$_3$, 500 MHz), δ8.2 (m, 3H), 7.8 (m, 2H), 7.7 (d, 1H), 7.6 (m, 2H), 7.5 (m, 3H), 6.5 (d, 1H), 3.0 (br, 2H), 2.7 (br, 3H), 2.2 (br, 1H), 1.7 (br 2H), 1.5 (br, 1H), 1.3 (br, 1H)

EXAMPLE 109

(3R)-3-[(S)-(1-fluoronaphthalen-2-yl)(5-phenyl-2H-tetrazol-2-yl)methyl]piperidine

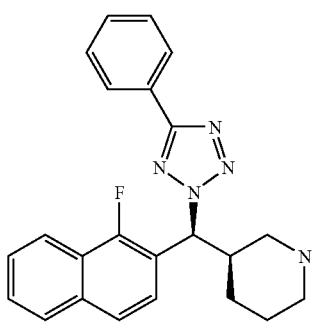 [SMILES: Fc1c([C@H]([C@@H]2CCCNC2)n2nnc(-c3ccccc3)n2)ccc2ccccc12]

The procedure given in Example 101 was followed using 5-phenyl-1H-tetrazole as a reactant, instead of 1H-tetrazole to give (3R)-3-[(S)-(1-fluoronaphthalen-2-yl)(5-phenyl-2H-tetrazol-2-yl)methyl]piperidine.

1H-NMR (CDCl$_3$, 500 MHz), δ8.2 (m, 3H), 7.9 (t, 1H), 7.8 (d, 1H), 7.7 (d, 1H), 7.6 (m, 2H), 7.5 (m, 3H), 6.5 (d, 1H), 3.0 (br, 1H), 2.9 (br, 2H), 2.6 (br, 1H), 2.5 (br, 1H), 2.0 (br, 1H), 1.8 (br, 1H), 1.5 (br, 2H), 1.3 (br, 1H)

EXAMPLE 110

(3S)-3-[(R)-(1-fluoronaphthalen-2-yl)(5-phenyl-2H-tetrazol-2-yl)methyl]piperidine

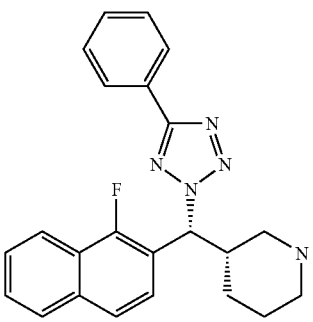 [SMILES: Fc1c([C@@H]([C@H]2CCCNC2)n2nnc(-c3ccccc3)n2)ccc2ccccc12]

The procedure given in Example 102 was followed using 5-phenyl-1H-tetrazole as a reactant, instead of 1H-tetrazole to give (3S)-3-[(R)-(1-fluoronaphthalen-2-yl)(5-phenyl-2H-tetrazol-2-yl)methyl]piperidine.

1H-NMR (CDCl$_3$, 500 MHz), δ8.2 (m, 3H), 7.9 (t, 1H), 7.8 (d, 1H), 7.7 (d, 1H), 7.6 (m, 2H), 7.5 (m, 3H), 6.5 (d, 1H), 3.0 (br, 1H), 2.9 (br, 2H), 2.6 (br, 1H), 2.5 (br, 1H), 2.0 (br, 1H), 1.8 (br, 1H), 1.5 (br, 2H), 1.3 (br, 1H)

EXAMPLE 111

(3R)-3-[(R)-(6-fluoronaphthalen-2-yl)(5-methyl-2H-tetrazol-2-yl)methyl]piperidine

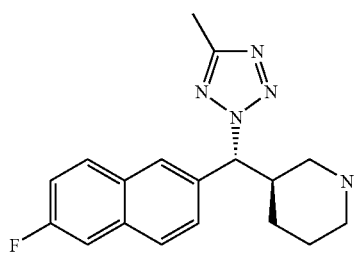 [SMILES: Cc1nnn([C@@H](c2ccc3cc(F)ccc3c2)[C@@H]2CCCNC2)n1]

The procedure given in Example 83 was followed using 5-methyl-1H-tetrazole as a reactant, instead of 1H-tetrazole to give (3R)-3-[(R)-(6-fluoronaphthalen-2-yl)(5-methyl-2H-tetrazol-2-yl)methyl]piperidine.

1H-NMR (CDCl$_3$, 500 MHz), δ8.0 (s, 1H), 7.8 (m, 3H), 7.4 (d, 1H), 7.3 (m, 1H), 5.8 (d, 1H), 3.0 (br, 1H), 2.9 (br, 1H), 2.6 (br, 2H), 2.5 (s, 3H), 2.4 (br, 1H), 2.2 (br, 1H), 1.7 (br, 1H), 1.6 (br, 1H), 1.5 (br, 1H), 1.2 (br, 1H)

EXAMPLE 112

(3)-1-butyl-3-[(S)-naphthalen-2-yl(2H-tetrazol-2-yl)methyl]piperidine

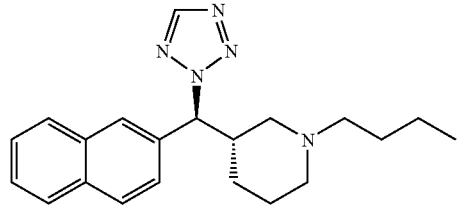 [SMILES: CCCCN1CCC[C@H]([C@@H](c2ccc3ccccc3c2)n2ncnn2)C1]

The procedure given in Example 73 was followed using 1-Iodobutane as a reactant instead of iodoethane to give (3S)-1-butyl-3-[(S)-naphthalen-2-yl(2H-tetrazol-2-yl)methyl]piperidine.

d8.5 (s, 1H), 8.0 (d, 1H), 7.7 (m, 4H), 7.4 (d, 2H), 6.1 (d, 1H), 2.2 (m, 4H), 2.0 (m, 4H), 1.9 (m, 1H), 1.5 (m, 4H), 1.4 (m, 2H), 1.2 (m, 3H)

EXAMPLE 113

4-[(S)-naphthalen-2-yl(2H-tetrazol-2-yl)methyl]piperidine

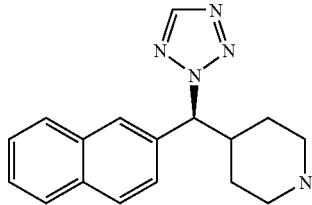

A mixture of 2-bromonaphthalene (4.59 mmol) and magnesium (5.508 mmol) was stirred vigorously in anhydrous THF (10 ml) under nitrogen atmosphere for 1 h to prepare naphthalen-2-ylmagnesium bromide solution. To this resulting solution was added tert-butyl-4-[methoxy(methyl)carbamoyl]piperidine-1-carboxylate (1.836 mmol) slowly at 0° C. After 10 min, the reaction mixture was warmed up to room temperature slowly and stirred for 2 hours. This solution was then quenched with aqueous NH$_4$Cl (10 ml) and ethyl acetate (1 ml) was added. Organic layer was separated from aqueous layer, washed with brine. The combined organic layer was dried over anhydrous MgSO$_4$ and concentrated in vacuo.

The crude product was dissolved in anhydrous THF. To this solution was slowly added (R)-2-methyl-CBS-oxazaborolidine (1.0M in toluene, 0.5 equiv) at −78° C. After 5 min, borane-THF complex (3 equiv) was added slowly. The reaction mixture was then transferred into the freezer and left overnight. The mixture was cooled to 0° C. and water was added dropwise to quench the reaction. The reaction mixture was diluted with ethyl acetate, washed with 5% aq NaOH, water, brine, and dried over MgSO$_4$. After concentration, the crude product was purified by flash column chromatography with a 4-35% ethyl acetate in hexanes gradient to afford enantiomeric mixture of tert-butyl 4-((R)-hydroxy(naphthyl)methyl)piperidine-1-carboxylate.

To a stirred solution of triphenylphosphine (2.754 mmol) and 1H-tetrazole (2.754 mmol) in THF (6 ml) was added previously prepared product (1.836 mmol) in THF (2 ml) at room temperature. The reaction mixture was stirred for 15 minutes, followed by the dropwise addition of diisopropyl azodicarboxylate (3.672 mmol) at 0° C. The solution was further stirred for 1 hour at room temperature. When the reaction was complete, the crude mixture was purified with silica gel chromatography (ethyl acetate:hexane=1:6).

The resulting product was dissolved in 6% HCl-MeOH solution and allowed to stir for 6 h. The solvent was removed under reduced pressure and basified with 1N NaOH to afford enantiomeric mixture of 4-[(S)-naphthalen-2-yl(2H-tetrazol-2-yl)methyl]piperidine. Enantiomeric pure compound of 4-[(S)-naphthalen-2-yl(2H-tetrazol-2-yl)methyl]piperidine was obtained from the enantiomeric mixture using a CHIRALPACK OD-H column (manufactured by Daicel Chemical Industries, Ltd.) as the Prep-LC column, at a column temperature of 25° C., with n-hexane/isopropylalcohol including 0.1% triethylamine (90:10) as the eluent.

1H-NMR (CDCl$_3$, 200 MHz), d 8.5 (s, 1H), 8.0 (s, 1H), 7.8 (m, 3H), 7.7 (m, 1H) 7.5 (m, 2H), 5.8 (d, 1H), 3.0 (br, 2H), 2.7 (m, 3H), 1.3 (m, 4H)

EXAMPLE 114

4-[(R)-naphthalen-2-yl(2H-tetrazol-2-yl)methyl]piperidine

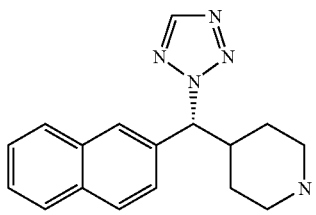

The procedure given in Example 113 was followed using (S)-2-methyl-CBS-oxazaborolidine as a reactant, instead of (R)-2-methyl-CBS-oxazaborolidine to give 4-[(R)-naphthalen-2-yl(2H-tetrazol-2-yl)methyl]piperidine.

1H-NMR (CDCl₃, 200 MHz), d 8.5 (s, 1), 8.0 (s, 1H), 7.8 (m, 3H), 7.7 (m, 1H) 7.5 (m, 2H), 5.8 (d, 1H), 3.0 (br, 2H), 2.7 (m, 3H), 1.3 (m, 4H)

EXAMPLE 115

4-[(S)-naphthalen-2-yl(1H-tetrazol-2-yl)methyl]piperidine

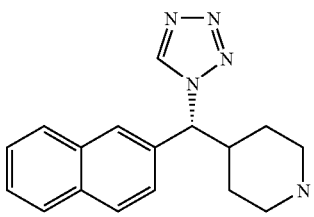

The procedure was given in Example 113 to give 4-[(S)-naphthalen-2-yl(1H-tetrazol-2-yl)methyl]piperidine.
1H-NMR (CDCl₃, 200 MHz), d 8.4 (s, 1H), 7.4 (d, 2H), 7.1 (d, 2H), 5.5 (d, 1H), 3.0 (br, 2H), 2.6 (m, 3H), 2.2 (s, 3H), 1.4 (br, 1H), 1.0 (m, 3H)

EXAMPLE 116

4-[(R)-naphthalen-2-yl(1H-tetrazol-2-yl)methyl]piperidine

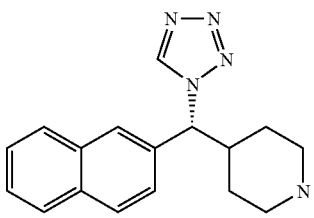 [SMILES: c1ccc2cc([C@@H](C3CCNCC3)n3cnnn3)ccc2c1]

The procedure was given in Example 114 to give 4-[(R)-naphthalen-2-yl(1H-tetrazol-2-yl)methyl]piperidine.
1H-NMR (CDCl₃, 200 MHz), d 8.4 (s, 1H), 7.4 (d, 2H), 7.1 (d, 2H), 5.5 (d, 1H), 3.0 (br, 2H), 2.6 (m, 3H), 2.2 (s, 3H), 1.4 (br, 1H), 1.1 (m, 3H.)

EXAMPLE 117

4-[(S)-(4-methylphenyl)(2H-tetrazol-2-yl)methyl]piperidine

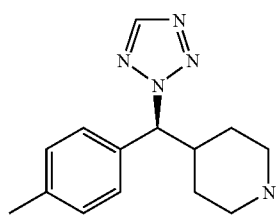 [SMILES: Cc1ccc([C@H](C2CCNCC2)n2ncnn2)cc1]

The procedure given in Example 113 was followed using 2-bromo-4-methylbenzene as a reactant, instead of 2-bromonaphthalene to give 4-[(S)-(4-methylphenyl)(2H-tetrazol-2-yl)methyl]piperidine.
1H-NMR (CDCl₃, 200 MHz), d 8.4 (s, 1H), 7.4 (d, 2H), 7.1 (d, 2H), 5.5 (d, 1H), 3.0 (br, 2H), 2.6 (m, 3H), 2.2 (s, 3H), 1.4 (br, 1H), 1.1 (m, 3H)

EXAMPLE 118

4-[(R)-(4-methylphenyl)(2H-tetrazol-2-yl)methyl]piperidine

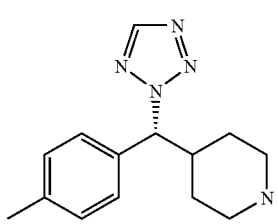 [SMILES: Cc1ccc([C@@H](C2CCNCC2)n2ncnn2)cc1]

The procedure given in Example 117 was followed using (S)-2-methyl-CBS-oxazaborolidine as a reactant, instead of (R)-2-methyl-CBS-oxazaborolidine to give 4-[(R)-(4-methylphenyl)(2H-tetrazol-2-yl)methyl]piperidine.
1H-NMR (CDCl₃, 200 MHz), d 8.4 (s, 1H), 7.4 (d, 2H), 7.1 (d, 2H), 5.5 (d, 1H), 3.0 (br, 2H), 2.6 (m, 3H), 2.2 (s, 3H), 1.4 (br, 1H), 1.1 (m, 3H)

EXAMPLE 119

4-[(S)-(4-methylphenyl)(1H-tetrazol-2-yl)methyl]piperidine

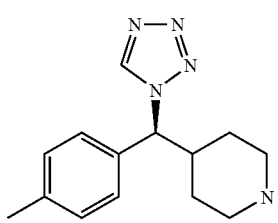 [SMILES: Cc1ccc([C@H](C2CCNCC2)n2cnnn2)cc1]

The procedure was given in Example 117 to give 4-[(S)-(4-methylphenyl)(1H-tetrazol-2-yl)methyl]piperidine.
1H-NMR (CDCl₃, 200 MHz), d 8.7 (s, 1H), 7.3 (d, 2H), 7.1 (d, 2H), 5.2 (d, 1H), 3.0 (br, 2H), 2.5 (m, 3H), 2.3 (s, 3H), 1.4 (br, 1H), 1.2 (m, 3H)

EXAMPLE 120

4-[(R)-(4-methylphenyl)(1H-tetrazol-2-yl)methyl]piperidine

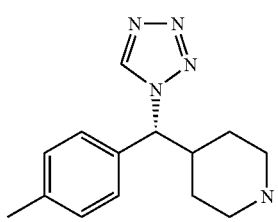 [SMILES: Cc1ccc([C@@H](C2CCNCC2)n2cnnn2)cc1]

The procedure was given in Example 118 to give 4-[(R)-(4-methylphenyl)(1H-tetrazol-2-yl)methyl]piperidine.

1H-NMR (CDCl₃, 200 MHz), d 8.7 (s, 114), 7.3 (d, 2H), 7.1 (d, 2H), 5.2 (d, 1H), 3.0 (br, 2H), 2.5 (m, 3H), 2.3 (s, 3H), 1.4 (br, 1H), 1.2 (m, 3H)

EXAMPLE 121

4-[(S)-naphthalen-2-yl(2H-1,2,3-triazol-2-yl)methyl]piperidine

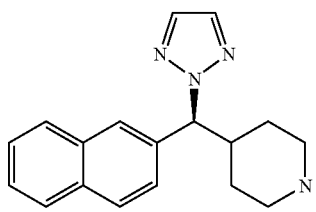 [SMILES: c1ccc2cc([C@H](C3CCNCC3)n3nccn3)ccc2c1]

The procedure given in Example 113 was followed using 1H-[1,2,3]-triazole as a reactant, instead of 1H-tetrazole to give 4-[(S)-naphthalen-2-yl(2H-1,2,3-triazol-2-yl)methyl]piperidine.

1H-NMR (CDCl₃, 200 MHz), d 7.9 (s, 1H), 7.8 (m, 3H), 7.7 (m, 1H), 7.6 (m, 2H), 7.5 (m, 2H), 5.5 (d, 1H), 3.1 (br, 2H), 2.7 (m, 3H), 1.3 (m, 4H)

EXAMPLE 122

4-[(R)-naphthalen-2-yl(2H-1,2,3-triazol-2-yl)methyl]piperidine

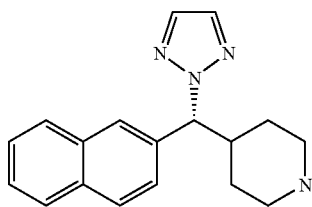 [SMILES: c1ccc2cc([C@@H](C3CCNCC3)n3nccn3)ccc2c1]

The procedure given in Example 121 was followed using (S)-2-methyl-CBS-oxazaborolidine as a reactant, instead of (R)-2-methyl-CBS-oxazaborolidine to give 4-[(R)-naphthalen-2-yl(2H-1,2,3-triazol-2-yl)methyl]piperidine.

1H-NMR (CDCl₅, 200 MHz), d 7.9 (s, 1H), 7.8 (m, 3H), 7.7 (m, 1H), 7.6 (m, 2H), 7.5 (m, 2H), 5.5 (d, 1H), 3.1 (br, 2H), 2.7 ((m, 3H), 1.3 (m, 4H)

EXAMPLE 123

4-[(S)-naphthalen-2-yl(1H-1,2,3-triazol-2-yl)methyl]piperidine

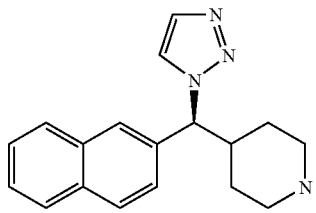 [SMILES: c1ccc2cc([C@H](C3CCNCC3)n3ccnn3)ccc2c1]

The procedure was given in Example 121 to give 4-[(S)-naphthalen-2-yl(1H-1,2,3-triazol-2-yl)methyl]piperidine.

1H-NMR (CDCl₃, 200 MHz), d 7.8 (m, 4H), 7.6 (m, 3H), 7.5 (m, 2H), 5.3 (d, 1H), 3.0 (br, 2H), 2.6 (m, 3H), 1.3 (m, 4H)

EXAMPLE 124

4-[(R)-naphthalen-2-yl(1H-1,2,3-triazol-2-yl)methyl]piperidine

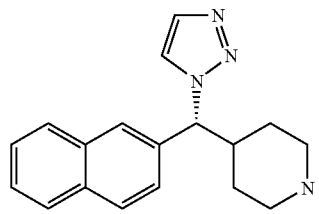

The procedure was given in Example 122 to give 4-[(R)-naphthalen-2-yl(1H-1,2,3-triazol-2-yl)methyl]piperidine.

1H-NMR (CDCl₃, 200 MHz), d 7.8 (m, 4H), 7.6 (m, 3H), 7.5 (m, 2H), 5.3 (d, 1H), 3.0 (br, 2H), 2.6 (m, 3H), 1.3 (m, 4H)

EXAMPLE 125

4-[(S)-(3,4-dichlorophenyl)(2H-tetrazol-2-yl)methyl]piperidine

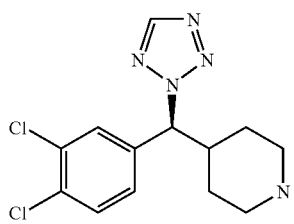 [SMILES: Clc1ccc([C@H](C2CCNCC2)n2ncnn2)cc1Cl]

The procedure given in Example 113 was followed using 2-bromo-3,4-dichlorobenzene as a reactant, instead of 2-bromonaphthalene to give 4-[(S)-(3,4-dichlorophenyl)(2H-tetrazol-2-yl)methyl]piperidine.

1H-NMR (CDCl₃, 200 MHz), d 8.5 (s, 1H), 7.6 (s, 1H) 7.4 (d 2H), 5.5 (d, 1H), 3.0 (br, 2H), 2.6 (m, 3H), 2.4 (br, 1H), 1.4 (br, 1H), 1.2 (m, 3H)

EXAMPLE 126

4-[(R)-(3,4-dichlorophenyl)(2H-tetrazol-2-yl)methyl]piperidine

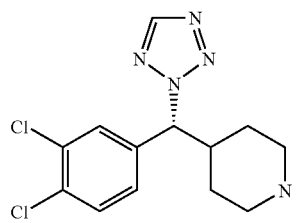 [SMILES: Clc1ccc([C@@H](C2CCNCC2)n2ncnn2)cc1Cl]

The procedure given in Example 125 was followed using (S)-2-methyl-CBS-oxazaborolidine as a reactant, instead of (R)-2-methyl-CBS-oxazaborolidine to give 4-[(R)-(3,4-dichlorophenyl)(2H-tetrazol-2-yl)methyl]piperidine.

1H-NMR (CDCl$_3$, 200 MHz), d 8.5 (s, 1H), 7.6 (s, 1H) 7.4 (d, 2H), 5.5 (d, 1H), 3.0 (br, 2H), 2.6 (m, 3H), 2.4 (br, 1H), 1.4 (br, 1H), 1.2 (m, 3H)

The therapeutic use of the racemic or enantiomerically enriched compounds of general structural formula (I), (III) and (IV) and their pharmaceutically useful salts have been established by the following tests.

Serotonin Transporter Reuptake Inhibition Assay

The method to test the ability of compounds to inhibit transporters from reuptake of serotonin followed Gu H. et al., J Biol Chem., 1994, 269, p 7214~7130.

The recombinant HEK-293 cells with human serotonin transporter were plated. Test compounds were pre-incubated with cells (2×10$^5$/ml) in modified Tris-HEPES buffer pH 7.1 for 20 minutes at 25° C. and then they were incubated for additional 10 minutes after 65 nM of [$^3$H]Serotonin was added. Bound cells were filtered and counted to determine [$^3$H]Serotonin uptake. Reduction of [$^3$H]Serotonin uptake by 50 percent or more (≥50%) relative to 10 µM fluoxetine indicates significant inhibitory activity. Compounds were screened at 10, 1, 0.1, 0.01 and 0.001 µM for IC50s.

Norepinephrine Transporter Reuptake Inhibition Assay

Norepinephrine transporter reuptake inhibition assay used the method described by Galli A. et al., J Exp Biol., 1995, 198, p 2197~2212.

MDCK cells with stably expressed human recombinant norepinephrine transporter were plated one day. Test compounds were pre-incubated with cells (2×10$^5$/ml) in modified Tris-HEPES buffer pH 7.1 for 20 minutes at 25° C. and then they were incubated for additional 10 minutes after 25 nM of [$^3$H]Norepinephrine was added. A lysate was obtained from solubilized cells and the filtered lysate was counted to determine [$^3$H]Norepinephrine uptake. Reduction of [$^3$H]Norepinephrine uptake by 50 percent or more (≥50%) relative to 10 µM desipramine indicates significant inhibitory activity. Compounds were screened at 10, 1, 0.1, 0.01 and 0.001 µM to determine their IC50s.

Dopamine Transporter Reuptake Inhibition Assay

The assay followed the method modified from Pristupa Z. B. et al., Mol Pharmacol., 1994, p 125~135.

CHO-K1 cells with human recombinant dopamine transporter were plated. Test compounds were pre-incubated with cells (4×10$^5$/ml) in modified Tris-HEPES buffer pH 7.1 for 20 minutes at 25° C. and then they were incubated for additional 10 minutes after 50 nm of [$^3$H]Dopamine was added. A lysate is obtained from solubilized cells and counted to determine [$^3$H]Dopamine uptake. Reduction of [$^3$H]Dopamine uptake by 50 percent or more (≥50%) relative to 10 µM nomifensine indicates significant inhibitory activity. Compounds were tested at 10, 1, 0.1, 0.01 and 0.001 µM for IC50s.

The results obtained by testing compounds of the invention are given in the following table 1.

TABLE 1

| Test Compound | Inhibition % at 100 nM | | |
|---|---|---|---|
| | 5-HT reuptake | NE reuptake | DA reuptake |
| Example 1 | 81% | 94% | 88% |
| Example 2 | 98% | 85% | 85% |
| Example 10 | 93% | 87% | 93% |
| Example 12 | 83% | 90% | 92% |
| Example 13 | 84% | 87% | 63% |
| Example 14 | 76% | 70% | 52% |
| Example 15 | 75% | 98% | 99% |
| Example 35 | 76% | 72% | 78% |
| Example 67 | 97% | 90% | 81% |
| Example 68 | 96% | 57% | 63% |
| Example 70 | 95% | 14% | 3% |
| Example 71 | 92% | 46% | 54% |
| Example 72 | 86% | 6% | 2% |
| Example 75 | 86% | -1% | 41% |
| Example 80 | 59% | 55% | 84% |
| Example 83 | 96% | 78% | 66% |
| Example 84 | 44% | 5% | -4% |
| Example 85 | 94% | 74% | 81% |
| Example 86 | 93% | -1% | 35% |
| Example 90 | 87% | 39% | 44% |

The data in Table 1 show that racemic or enantiomerically enriched novel 3 or 4-substituted piperidine derivatives, the compounds of the invention have a significantly high inhibition potency of the serotonin, norepinephrine, dopamine transporter reuptake. This inhibition of serotonin, norepinephrine, dopamine transporter reuptake has been associated with the treatment of one or more of the CNS disorders such as depression, anxiety and pain disorder.

Forced Swimming Test in Mice (FST)

The Forced swimming test is an animal model based on the rodent's behavioral repertoire for screening drugs with potential antidepressant activity. As in several other models used for this goal, an uncontrollable stress stimulus produces behavioral changes that are sensitive to antidepressant treatment.

The mice were intraperitoneally treated with the test compound with an injection volume of 10 mg/kg. The group treated with 30% PEG400 served as a control group. Thirty minutes following administration, mice were individually forced to swim in a transparent glass vessel (14 cm high, 11.5 cm in diameter) filled with 10 cm of water at 25° C. The total duration of immobility (second) was measured during the last 4 minutes of a single 6-min test session. Mice were considered immobile when they made no further attempts to escape other than the movements necessary to keep their heads above the water. The potent ability of the compounds was determined as percent value of reduction in the duration of immobility comparing to the control group.

The results obtained by testing compounds of the invention are given in the following table 2:

TABLE 2

| Test Compound | Reduction % at 30ip |
|---|---|
| Example 1 | 56.3% |
| Example 2 | 37.5% |
| Example 12 | 9.7% |
| Example 13 | 9.4% |
| Example 14 | 6.4% |
| Example 15 | 96.5% |
| Example 35 | 32.7% |
| Example 67 | 2.4% |
| Example 68 | 7.1% |
| Example 71 | 54.0% |
| Example 72 | 46.7% |
| Example 83 | 51.8% |
| Example 85 | 11.3% |
| Example 86 | 13.4% |

Specially the results of forced swimming test (FST) in mice as noted in Table 2 show the compounds of the invention are related to the treatment of depression.

Marble Burying Test

The Marble burying test is a screening tool for putative anxiolytics. In this test, control mice naturally bury glass marbles in the cage bedding and the administration of anxiolytic compounds, including Diazepam, reduces the number of buried marbles. Positive compounds in the marble burying test including selective serotonin reuptake inhibitor may be especially beneficial to obsessive-compulsive disorder.

A group of mice was intraperitoneally treated with test compound dissolved in 30% PEG400 with an injection volume of 10 ml/kg. The group treated with only 30% PEG400 served as a control group. Thirty minutes after the treatment the animals were individually placed in a polycarbonate cage which was same as used for animal housing with an open top located within a quiet room. Each cage consisted of ⅛ inch corn bedding 5 cm deep. Twenty four clean glass marbles (15 mm diameter) were evenly spaced in four rows of six on top of the bedding. Each mouse was left in the cage for 30 minutes and the number of marbles buried (buried more than ½ or ⅔) was counted. The potent ability of the compounds was determined as percent value of reduction in the number of marbles buried comparing to the control group.

The results obtained by testing compounds of the invention are given in the following table 3:

TABLE 3

| Test Compound | Reduction % at 30ip |
|---|---|
| Example 1 | 57.5% (at 10ip) |
| Example 2 | 67.5% (at 20ip) |
| Example 12 | 91.8% |
| Example 15 | 75.3% |
| Example 71 | 86.0% |
| Example 83 | 83.7% |

Specially the results of Marble burying test (MB) in mice as noted in Table 3 show the compounds of the invention are related to the treatment of anxiety.

Acetic Acid Induced Writhing Test (Writhing Test)

The Acetic acid-induced writhing test is a well-established nociceptive test using a chemical stimulus. Although several animal models of nociceptive tests have been developed to examine and compare the anti-nociceptive effects of different drugs, the anti-nociceptive effects of antidepressants appear to be test-dependent. Indeed, the acetic acid-induced writhing test is more sensitive to antidepressants than other tests using thermal, mechanical or electrical stimuli.

The animals were subcutaneously treated with the test compound with an injection volume of 10 ml/kg. The group treated with 30% PEG400 or saline served as a control group. Thirty minutes later, the mice were intraperitoneally treated with 0.8% (v/v) acetic acid. Each mouse was then placed in a cage for individual observation. The writhing numbers for 10 minutes were counted. The writhe is operationally defined as a contraction of the abdomen followed by stretching of the hind limbs. The potent ability of the compounds was determined as percent value of reduction in the number of writhing comparing to the control group.

The results obtained by testing compounds of the invention are given in the following table 4:

TABLE 4

| Test Compound | Reduction % at 30sc |
|---|---|
| Example 1 | 70.8% |
| Example 2 | 60.6% (at 10sc) |
| Example 12 | 50.5% |
| Example 13 | 71.8% |
| Example 15 | 55.3% |
| Example 68 | 48.1% (at 10sc) |
| Example 71 | 48.7% |
| Example 83 | 84.1% |
| Example 85 | 46.4% (at 10sc) |

Specially the results of Acetic acid induced writhing test (AA writhing test) in mice as noted in Table 4 show the compounds of the invention are related to the treatment of pain.

In therapeutic use as agents for various CNS disorders such as depression, anxiety and pain disorder, the compounds of the present invention, alone or in combination with pharmaceutically acceptable carrier, are administered to patients at a dosage of from 0.7 to 7,000 mg per day. For a normal human adult with a body weight of approximately 70 kg, the administration amount is translated into a daily dose of 0.01 to 100 mg per kg of body weight. The specific dosage employed, however, may vary depending upon the requirements of the patient, the severity of patient's condition and the activity of the compound. The determination of optimum dosages for a particular situation must clinically be done and is within the skill of the art.

In utilizing the compounds of the present invention for the central nervous system such as depression, anxiety and pain disorder, the compounds represented by general structural formula (I), (III) and (IV) can be administered in any form or mode which makes the compound bioavailable in effective amounts, including the oral, rectal, transdermal, subcutaneous, intravenous, intramuscular or intranasal routs. However it is preferred to administer the compounds orally. Since the compounds absorb well orally, it usually will not be necessary to resort to parenteral administration. For oral administration, the compounds having the general formula (I), (III) and (IV) are preferably combined with a pharmaceutical carrier The ratio of the carrier to the compound of structural formula (I), (III) and (IV) is not critical to express the effects of the medicine on the central nervous system, and they can vary considerably depending on whether the composition is to be filled into capsules or formed into tablets. In tableting, various edible pharmaceutical carriers or the mixture thereof can be used. Suitable carriers, for example, are a mixture of lactose,

What is claimed is:

1. A compound of Formula (I):

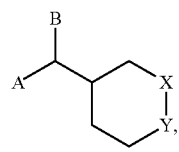
(I)

or a pharmaceutically acceptable salt thereof, wherein

A is selected from the group consisting of phenyl, naphthyl, benzothiophenyl, pyridyl, quinolyl and isoquinolyl, wherein A is optionally substituted by one or more substituents selected from the group consisting of H-, halo, straight- or branched-chain $C_1$-$C_4$ alkyl, straight- or branched-chain $C_1$-$C_3$ alkoxy, nitro, cyano, trifluoromethyl, trifluoromethoxy, methanesulfonyl, phenyloxy, phenyl and thienyl;

B is a substitution group selected from Formulae (II);

Formulae (II)

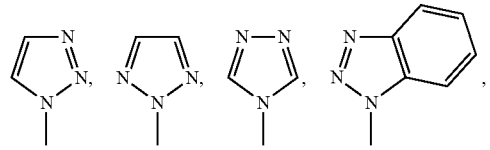

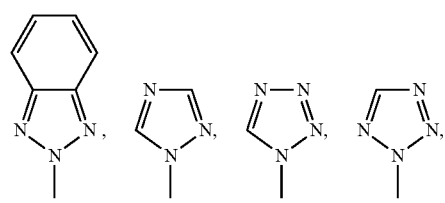

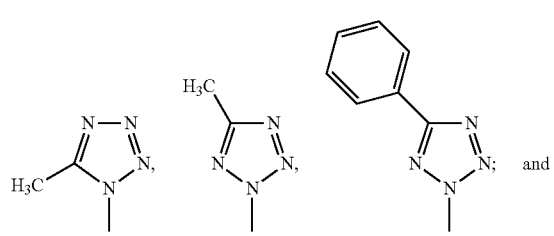

one of X and Y is -$CH_2$- and the other is -NR-, wherein R is H- or straight- or branched-chain $C_1$-$C_4$ alkyl.

2. The compound of claim 1, which is a compound selected from Formulae (III):

Formulae (III)

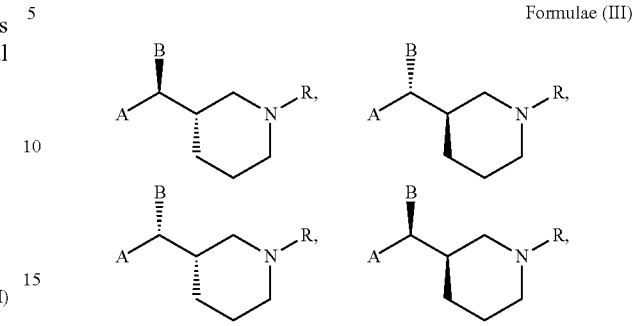

or a pharmaceutically acceptable salt thereof,
wherein each of A, B and R is as defined in claim 1.

3. The compound of claim 1, which is a compound selected from Formulae (IV):

Formulae (IV)

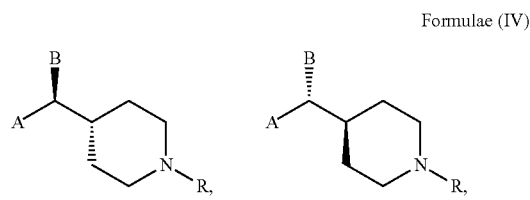

or a pharmaceutically acceptable salt thereof,
wherein each of A, B and R is as defined in claim 1.

4. The compound of claim 2, which is a compound selected from Formulae (XXII):

Formulae (XXII)

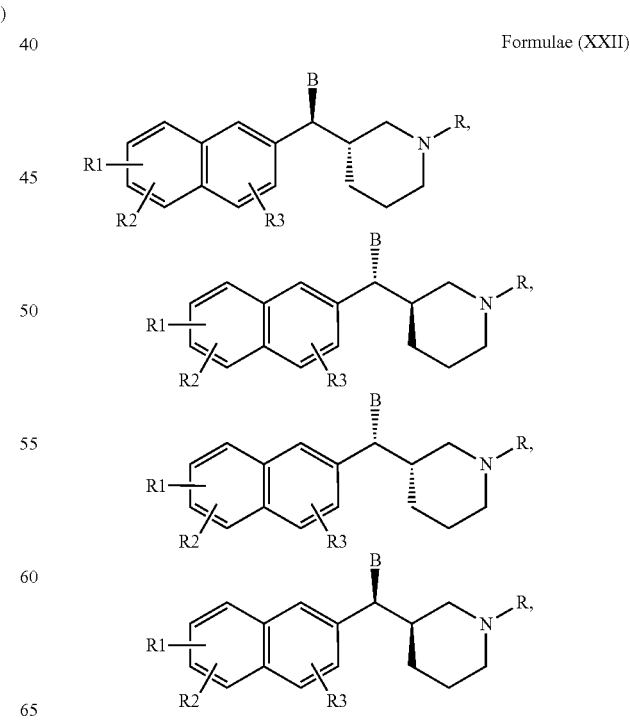

or a pharmaceutically acceptable salt thereof, wherein
each of $R_1$, $R_2$ and $R_3$ is independently selected from the group consisting of H-, halo, straight- or branched-chain $C_1$-$C_4$ alkyl, straight- or branched-chain $C_1$-$C_3$ alkoxy, nitro, cyano, trifluoromethyl, trifluoromethoxy, methanesulfonyl, phenyloxy, phenyl and thienyl; and
each of B and R is as defined in claim 1.

5. The compound of claim 4, wherein B is

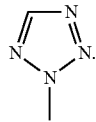

6. The compound of claim 4, wherein each of $R_1$, $R_2$ and $R_3$ is independently selected from the group consisting of H-, halo, methyl and methoxy.

7. The compound of claim 4, which is selected from the group consisting of:
3-[naphthalen-2-yl(2H-tetrazol-2-yl)methyl]piperidine,
(3R)-3-[(R)-naphthalen-2-yl(2H-tetrazol-2-yl)methyl]piperidine,
(3S)-3-[(S)-naphthalen-2-yl(2H-tetrazol-2-yl)methyl]piperidine,
(3R)-3-[(S)-naphthalen-2-yl(2H-tetrazol-2-yl)methyl]piperidine,
(3S)-3-[(R)-naphthalen-2-yl(2H-tetrazol-2-yl)methyl]piperidine,
3-[(6-chloronaphthalen-2-yl)(2H-tetrazol-2-yl)methyl]piperidine,
(3R)-3-[(R)-(6-chloronaphthalen-2-yl)(2H-tetrazol-2-yl)methyl]piperidine,
(3S)-3-[(S)-(6-chloronaphthalen-2-yl)(2H-tetrazol-2-yl)methyl]piperidine,
(3R)-3-[(S)-(6-chloronaphthalen-2-yl)(2H-tetrazol-2-yl)methyl]piperidine,
(3S)-3-[(R)-(6-chloronaphthalen-2-yl)(2H-tetrazol-2-yl)methyl]piperidine,
3-[(6-fluoronaphthalen-2-yl)(2H-tetrazol-2-yl)methyl]piperidine,
(3R)-3-[(R)-(6-fluoronaphthalen-2-yl)(2H-tetrazol-2-yl)methyl]piperidine,
(3S)-3-[(S)-(6-fluoronaphthalen-2-yl)(2H-tetrazol-2-yl)methyl]piperidine,
(3R)-3-[(S)-(6-fluoronaphthalen-2-yl)(2H-tetrazol-2-yl)methyl]piperidine, and
(3S)-3-[(R)-(6-fluoronaphthalen-2-yl)(2H-tetrazol-2-yl)methyl]piperidine.

8. The compound of claim 1, which is selected from the group consisting of:
(3R)-3-[(R)-naphthalen-2-yl(2H-tetrazol-2-yl)methyl]piperidine,
(3S)-3-[(S)-naphthalen-2-yl(2H-tetrazol-2-yl)methyl]piperidine,
(3R)-3-[(S)-naphthalen-2-yl(2H-tetrazol-2-yl)methyl]piperidine,
(3S)-3-[(R)-naphthalen-2-yl(2H-tetrazol-2-yl)methyl]piperidine,
(3R)-3-[(R)-naphthalen-2-yl(1 H-tetrazol-1-yl)methyl]piperidine,
(3S)-3-[(S)-naphthalen-2-yl(1 H-tetrazol-1-yl)methyl]piperidine,
(3R)-3-[(S)-naphthalen-2-yl(1 H-tetrazol-1-yl)methyl]piperidine,
(3S)-3-[(R)-naphthalen-2-yl(1 H-tetrazol-1-yl)methyl]piperidine,
(3S)-3-[(R)-(5-methyl-2H-tetrazol-2-yl)(naphthalen-2-yl)methyl]piperidine,
(3S)-3-[(S)-(5-methyl-2H-tetrazol-2-yl)(naphthalen-2-yl)methyl]piperidine,
(3R)-3-[(S)-(5-methyl-2H-tetrazol-2-yl)(naphthalen-2-yl)methyl]piperidine,
(3R)-3-[(R)-(5-methyl-2H-tetrazol-2-yl)(naphthalen-2-yl)methyl]piperidine,
(3R)-3-[(R)-naphthalen-2-yl(2H-1,2,3-triazol-2-yl)methyl]piperidine,
(3S)-3-[(S)-naphthalen-2-yl(2H-1,2,3-triazol-2-yl)methyl]piperidine,
(3R)-3-[(R)-naphthalen-1-yl(2H-tetrazol-2-yl)methyl]piperidine,
(3S)-3-[(S)-naphthalen-1-yl(2H-tetrazol-2-yl)methyl]piperidine,
(3S)-3-[(S)-(6-methoxynaphthalen-2-yl)(2H-tetrazol-2-yl)methyl]piperidine,
(3S)-3-[(R)-(6-methoxynaphthalen-2-yl)(2H-tetrazol-2-yl)methyl]piperidine,
(3S)-3-[(S)-(4-methyl-naphthalen-1-yl)(2H-tetrazol-2-yl)methyl]piperidine,
(3S)-3-[(R)-(4-methyl-naphthalen-1-yl)(2H-tetrazol-2-yl)methyl]piperidine,
(3R)-3-[(R)-(6-chloronaphthalen-2-yl)(2H-tetrazol-2-yl)methyl]piperidine,
(3S)-3-[(S)-(6-chloronaphthalen-2-yl)(2H-tetrazol-2-yl)methyl]piperidine,
(3R)-3-[(S)-(6-chloronaphthalen-2-yl)(2H-tetrazol-2-yl)methyl]piperidine,
(3S)-3-[(R)-(6-chloronaphthalen-2-yl)(2H-tetrazol-2-yl)methyl]piperidine,
(3S)-3-[(S)-(6-fluoronaphthalen-2-yl)(2H-tetrazol-2-yl)methyl]piperidine,
(3S)-3-[(R)-(6-fluoronaphthalen-2-yl)(2H-tetrazol-2-yl)methyl]piperidine,
(3S)-1-ethyl-3-[(S)-naphthalen-2-yl(2H-tetrazol-2-yl)methyl]piperidine, (3R)-3-[(R)-naphthalen-2-yl-(5-phenyl-tetrazol-2-yl)methyl]piperidine, (3S)-3-[(S)-naphthalen-2-yl-(5-phenyl-tetrazol-2-yl)methyl]piperidine, (3R)-3-[(S)-naphthalen-2-yl-(5-phenyl-tetrazol-2-yl)methyl]piperidine, (3S)-3-[(R)-naphthalen-2-yl-(5-phenyl-tetrazol-2-yl)methyl]pipendine,
1-{(S)-naphthalen-2-yl[(3S)-pipericlin-3-yl]methyl}-1 H-benzotriazole,
1-{(R)-naphthalen-2-yl[(3S)-pipericlin-3-yl]methyl}-1 H-benzotriazole,
2-{(S)-naphthalen-2-yl[(3S)-pipenclin-3-yl]methyl}-2H-benzotriazole,
2-{(R)-naphthalen-2-yl[(3S)-pipericlin-3-yl]methyl}-2H-benzotriazole,
(3R)-3-[(R)-(6-fluoronaphthalen-2-yl)(2H-tetrazol-2-yl)methyl]pipendine,
(3R)-3-[(S)-(6-fluoronaphthalen-2-yl)(2H-tetrazol-2-yl)methyl]pipendine,
(3S)-3-[(S)-(6-methylnaphthalen-2-yl)(2H-tetrazol-2-yl)methyl]pipendine,
(3S)-3-[(R)-(6-methylnaphthalen-2-yl)(2H-tetrazol-2-yl)methyl]pipendine,
(3S)-3-[(S)-(4-fluoronaphthalen-1 -yl)(2H-tetrazol-2-yl)methyl]piperidine,
(3S)-3-[(R)-(4-fluoronaphthalen-1 -yl)(2H-tetrazol-2-yl)methyl]piperidine,
(3S)-3-[(R)-naphthalen-2-yl(4H-1 ,2,4-triazol-4-yl)methyl]piperidine, (3S)-3-[(S)-naphthalen-2-yl(1H-1,2,4-triazol-1-yl)methyl]piperidine,
(3S)-3-[(R)-naphthalen-2-yl(1H-1,2,4-triazol-1-yl)methyl]piperidine,
(3R)-3-[(R)-(1-fluoronaphthalen-2-yl)(2H-tetrazol-2-yl)methyl]piperidine,
(3S)-3-[(S)-(1-fluoronaphthalen-2-yl)(2H-tetrazol-2-yl)methyl]piperidine,
(3R)-3-[(S)-(1-fluoronaphthalen-2-yl)(2H-tetrazol-2-yl)methyl]piperidine,
(3S)-3-[(R)-(1-fluoronaphthalen-2-yl)(2H-tetrazol-2-yl)methyl]piperidine,
(3R)-3-[(R)-(1-fluoronaphthalen-2-yl)(5-methyl-2H-tetrazol-2-yl)methyl]piperidine,
(3S)-3-[(S)-(1-fluoronaphthalen-2-yl)(5-methyl-2H-tetrazol-2-yl)methyl]piperidine,
(3R)-3-[(S)-(1-fluoronaphthalen-2-yl)(5-methyl-2H-tetrazol-2-yl)methyl]piperidine,
(3S)-3-[(R)-(1-fluoronaphthalen-2-yl)(5-methyl-2H-tetrazol-2-yl)methyl]piperidine,
(3R)-3-[(R)-(1-fluoronaphthalen-2-yl)(5-phenyl-2H-tetrazol-2-yl)methyl]pipendine,
(3S)-3-[(S)-(1-fluoronaphthalen-2-yl)(5-phenyl-2H-tetrazol-2-yl)methyl]piperidine,
(3R)-3-[(S)-(1-fluoronaphthalen-2-yl)(5-phenyl-2H-tetrazol-2-yl)methyl]piperidine,
(3S)-3-[(R)-(1-fluoronaphthalen-2-yl)(5-phenyl-2H-tetrazol-2-yl)methyl]piperidine,
(3R)-3-[(R)-(6-fluoronaphthalen-2-yl)(5-methyl-2H-tetrazol-2-yl)methyl]piperidine
(3S)-1-butyl-3-[(S)-naphthalen-2-yl(2H-tetrazol-2-yl)methyl]piperidine,
4-[(S)-naphthalen-2-yl(2H-tetrazol-2-yl)methyl]piperidine,
4-[(R)-naphthalen-2-yl(2H-tetrazol-2-yl)methyl]piperidine,
4-[(S)-naphthylene-2-yl(1H-tetrazol-2-yl)methyl]piperidine,
4-[(R)-naphthalen-2-yl(1H-tetrazol-2-yl)methyl]piperidine,
4-[(S)-naphthalen-2-yl(2H-1,2,3-triazol-2-yl)methyl]piperidine,
4-[(R)-naphthalen-2-yl(2H-1,2,3-triazol-2-yl)methyl]piperidine,
4-[(S)-naphthalen-2-yl(1H-1,2,3-triazol-2-yl)methyl]piperidine, and
4-[(R)-naphthalen-2-yl(1H-1,2,3-triazol-2-yl)methyl]piperidine.

9. The compound of claim 1, which is selected from the group consisting of:
(3R)-3-[(R)-(3,4-dichlorophenyl)(2H-tetrazol-2-yl)methyl]piperidine,
(3S)-3-[(S)-(3,4-dichlorophenyl)(2H-tetrazol-2-yl)methyl]piperidine,
(3R)-3-[(R)-(4-chlorophenyl)(2H-tetrazol-2-yl)methyl]piperidine,
(3S)-3-[(S)-(4-chlorophenyl)(2H-tetrazol-2-yl)methyl]piperidine,
(3R)-3-[(S)-(4-chlorophenyl)(2H-tetrazol-2-yl)methyl]piperidine,
(3S)-3-[(R)-(4-chlorophenyl)(2H-tetrazol-2-yl)methyl]piperidine,
(3R)-3-[(R)-(4-isopropylphenyl)(2H-tetrazol-2-yl)methyl]piperidine,
(3S)-3-[(S)-(4-isopropylphenyl)(2H-tetrazol-2-yl)methyl]piperidine,
(3R)-3-[(S)-(4-isopropylphenyl)(2H-tetrazol-2-yl)methyl]piperidine,
(3R)-3-[(R)-(4-isopropylphenyl)(2H-tetrazol-2-yl)methyl]piperidine,
(3S)-3-[(S)-(3,4-dimethoxyphenyl)(2H-tetrazol-2-yl)methyl]piperidine,
(3S)-3-[(R)-(3,4-dimethoxyphenyl)(2H-tetrazol-2-yl)methyl]piperidine,
(3S)-3-[(S)-(3,4-dimethoxyphenyl)(1H-tetrazol-1-yl)methyl]piperidine,
(3S)-3-[(R)-(3,4-dimethoxyphenyl)(1H-tetrazol-1-yl)methyl]piperidine,
(3S)-3-[(S)-phenyl(2H-tetrazol-2-yl)methyl]piperidine,
(3S)-3-[(R)-phenyl(2H-tetrazol-2-yl)methyl]piperidine,
(3S)-3-{(S)-2H-tetrazol-2-yl[4-trifluoromethyl)phenyl]methyl}piperidine,
(3S)-3-{(R)-2H-tetrazol-2-yl[4-(trifluoromethyl)phenyl]methyl}piperidine,
(3S)-3-[(S)-(4-methylphenyl)(2H-tetrazol-2-yl)methyl]piperidine,
(3S)-3-[(R)-(4-methylphenyl)(2H-tetrazol-2-yl)methyl]piperidine,
(3S)-3-[(S)-(3-chlorophenyl)(2H-tetrazol-2-yl)methyl]piperidine,
(3S)-3-[(R)-(3-chlorophenyl)(2H-tetrazol-2-yl)methyl]piperidine,
(3S)-3-[(S)-(2,4-difluorophenyl)(2H-tetrazol-2-yl)methyl]piperidine,
(3S)-3-[(R)-(2,4-difluorophenyl)(2H-tetrazol-2-yl)methyl]piperidine,
(3S)-3-[(S)-(4-methoxyphenyl)(2H-tetrazol-2-yl)methyl]piperidine,
(3S)-3-[(R)-(4-methoxyphenyl)(2H-tetrazol-2-yl)methyl]piperidine,
(3S)-3-[(S)-(4-methoxyphenyl)(1H-tetrazol-1-yl)methyl]piperidine,
(3S)-3-[(R)-(4-methoxyphenyl)(1H-tetrazol-1-yl)methyl]piperidine,
(3S)-3-[(S)-(4-phenoxyphenyl)(2H-tetrazol-2-yl)methyl]piperidine,
(3S)-3-[(R)-(4-phenoxyphenyl)(2H-tetrazol-2-yl)methyl]piperidine,
(3S)-3-[(S)-(4-phenoxyphenyl)(1H-tetrazol-1-yl)methyl]piperidine,
(3S)-3-[(R)-(4-phenoxyphenyl)(1H-tetrazol-1-yl)methyl]piperidine,
(3S)-3-[(S)-(4-fluorophenyl)(2H-tetrazol-2-yl)methyl]piperidine,
(3S)-3-[(R)-(4-fluorophenyl)(2H-tetrazol-2-yl)methyl]piperidine,
(3S)-3-[(S)-biphenyl-4-yl(2H-tetrazol-2-yl)methyl]piperidine,
(3S)-3-[(R)-biphenyl-4-yl(2H-tetrazol-2-yl)methyl]piperidine,
(3S)-3-{(S)-2H-tetrazol-2-yl[3-(trifluoromethyl)phenyl]methyl}piperidine,
(3S)-3-{(R)-2H-tetrazol-2-yl[3-(trifluoromethyl)phenyl]methyl}piperidine,
(3S)-3-[(S)-(4-propylphenyl)(2H-tetrazol-2-yl)methyl]piperidine,
(3S)-3-[(R)-(4-propylphenyl)(2H-tetrazol-2-yl)methyl]piperidine,
(3S)-3-[(S)-(3-methylphenyl)(2H-tetrazol-2-yl)methyl]piperidine,
(3S)-3-[(R)-(3-methylphenyl)(2H-tetrazol-2-yl)methyl]piperidine, (3S)-3-[(S)-(3-methoxyphenyl)(2H-tetrazol-2-yl)methyl]piperidine,
(3S)-3-[(R)-(3-methoxyphenyl)(2H-tetrazol-2-yl)methyl]piperidine,
(3S)-3-[(S)-(3,4-difluorophenyl)(2H-tetrazol-2-yl)methyl]piperidine,
(3S)-3-[(R)-(3,4-difluorophenyl)(2H-tetrazol-2-yl)methyl]piperidine,
(3S)-3-[(S)-(2,3-dichlorophenyl)(2H-tetrazol-2-yl)methyl]piperidine,
(3S)-3-[(R)-(2,3-dichlorophenyl)(2H-tetrazol-2-yl)methyl]piperidine,
4-[(S)-(4-methylphenyl)(2H-tetrazol-2-yl)methyl]piperidine,
4-[(R)-(4-methylphenyl)(2H-tetrazol-2-yl)methyl]piperidine,
4-[(S)-(4-methylphenyl)(1 H-tetrazol-2-yl)methyl]piperidine,
4-[(R)-(4-methylphenyl)(1 H-tetrazol-2-yl)methyl]piperidine,
4-[(S)-(3,4-dichlorophenyl)(2H-tetrazol-2-yl)methyl]piperidine, and
4-[(R)-(3,4-dichlorophenyl)(2H-tetrazol-2-yl)methyl]piperidine.

10. The compound of claim 1, which is selected from the group consisting of:
(3S)-3-[(S)-1-benzothiophen-5-yl(2H-tetrazol-2-yl)methyl]piperidine,
(3S)-3-[(R)-1-benzothiophen-5-yl(2H-tetrazol-2-yl)methyl]piperidine,
(3S)-3-[(R)-1-benzothiophen-3-yl(2H-tetrazol-2-yl)methyl]piperidine,
(3S)-3-[(S)-1-benzothiophen-2-yl(2H-tetrazol-2-yl)methyl]piperidine, and
(3S)-3-[(R)-1-benzothiophen-2-yl(2H-tetrazol-2-yl)methyl]piperidine.

11. The compound of claim 1, which is selected from the group consisting of:
(3R)-3-[(R)-naphthalen-2-yl(2H-tetrazol-2-yl)methyl]piperidine,
(3S)-3-[(S)-naphthalen-2-yl(2H-tetrazol-2-yl)methyl]piperidine,
(3R)-3-[(R)-(5-methyl-2H-tetrazol-2-yl)(naphthalen-2-yl)methyl]piperidine,
(3R)-3-[(R)-naphthalen-2-yl(2H-1,2,3-triazol-2-yl)methyl]piperidine,
(3)-3-[(S)-naphthalen-2-yl(2H-1,2,3-triazol-2-yl)methyl]piperidine,
(3R)-3-[(R)-(3,4-dichlorophenyl)(2H-tetrazol-2-yl)methyl]piperidine,
(3S)-3-[(S)-(6-methoxynaphthalen-2-yl)(2H-tetrazol-2-yl)methyl]piperidine,
(3R)-3-[(R)-(6-chloronaphthalen-2-yl)(2H-tetrazol-2-yl)methyl]piperidine,
(3S)-3-[(S)-(6-chloronaphthalen-2-yl)(2H-tetrazol-2-yl)methyl]piperidine,
(3S)-3-[(S)-(6-fluoronaphthalen-2-yl)(2H-tetrazol-2-yl)methyl]piperidine,
(3S)-3-[(R)-(6-fluoronaphthalen-2-yl)(2H-tetrazol-2-yl)methyl]piperidine,
(3R)-3-[(R)-(6-fluoronaphthalen-2-yl)(2H-tetrazol-2-yl)methyl]piperidine,
(3S)-3-[(S)-(6-methylnaphthalen-2-yl)(2H-tetrazol-2-yl)methyl]piperidine, and
(3S)-3-[(R)-(6-methylnaphthalen-2-yl)(2H-tetrazol-2-yl)methyl]piperidine.

12. The compound of claim 1, which is
(3R)-3-[(R)-naphthalen-2-yl(2H-tetrazol-2-yl)methyl]piperidine or
(3S)-3-[(S)-naphthalen-2-yl(2H-tetrazol-2-yl)methyl]piperidine.

13. The compound of claim 1, which is (3S)-3-[(S)-naphthalen-2-yl(2H-tetrazol-2-yl)methyl]piperidine.

14. A pharmaceutical composition comprising a therapeutically effective amount of a compound of claim 1 and a pharmaceutically acceptable carrier.

15. A pharmaceutical composition comprising a therapeutically effective amount of a compound of claim 2 and a pharmaceutically acceptable carrier.

16. A pharmaceutical composition comprising a therapeutically effective amount of a compound of claim 3 and a pharmaceutically acceptable carrier.

17. A pharmaceutical composition comprising a therapeutically effective amount of a compound of claim 4 and a pharmaceutically acceptable carrier.

18. The pharmaceutical composition of claim 14, wherein the compound is selected from the group consisting of:
(3R)-3-[(R)-naphthalen-2-yl(2H-tetrazol-2-yl)methyl]piperidine,
(3S)-3-[(S)-naphthalen-2-yl(2H-tetrazol-2-yl)methyl]piperidine,
(3R)-3-[(R)-(5-methyl-2H-tetrazol-2-yl)(naphthalen-2-yl)methyl]piperidine,
(3R)-3-[(R)-naphthalen-2-yl(2H-1,2,3-triazol-2-yl)methyl]piperidine,
(3)-3-[(S)-naphthalen-2-yl(2H-1,2,3-triazol-2-yl)methyl]piperidine,
(3R)-3-[(R)-(3,4-dichlorophenyl)(2H-tetrazol-2-yl)methyl]piperidine,
(3S)-3-[(S)-(6-methoxynaphthalen-2-yl)(2H-tetrazol-2-yl)methyl]piperidine,
(3R)-3-[(R)-(6-chloronaphthalen-2-yl)(2H-tetrazol-2-yl)methyl]piperidine,
(3S)-3-[(S)-(6-chloronaphthalen-2-yl)(2H-tetrazol-2-yl)methyl]piperidine,
(3S)-3-[(S)-(6-fluoronaphthalen-2-yl)(2H-tetrazol-2-yl)methyl]piperidine,
(3S)-3-[(R)-(6-fluoronaphthalen-2-yl)(2H-tetrazol-2-yl)methyl]piperidine,
(3R)-3-[(R)-(6-fluoronaphthalen-2-yl)(2H-tetrazol-2-yl)methyl]piperidine,
(3S)-3-[(S)-(6-methylnaphthalen-2-yl)(2H-tetrazol-2-yl)methyl]piperidine, and
(3S)-3-[(R)-(6-methylnaphthalen-2-yl)(2H-tetrazol-2-yl)methyl]piperidine.

19. The pharmaceutical composition of claim 14, wherein the compound is:
(3R)-3-[(R)-naphthalen-2-yl(2H-tetrazol-2-yl)methyl]piperidine or
(3S)-3-[(S)-naphthalen-2-yl(2H-tetrazol-2-yl)methyl]piperidine.

20. The pharmaceutical composition of claim 14, wherein the compound is
(3S)-3-[(S)-naphthalen-2-yl(2H-tetrazol-2-yl)methyl]piperidine.

* * * * *